(12) United States Patent
Maezono et al.

(10) Patent No.: US 7,956,041 B2
(45) Date of Patent: Jun. 7, 2011

(54) PROPHYLACTIC AND THERAPEUTIC AGENT OF DIABETES MELLITUS

(75) Inventors: Katsumi Maezono, Kawasaki (JP); Nozomu Ishida, Kawasaki (JP); Koji Ohsumi, Kawasaki (JP); Hiroyuki Matsueda, Kawasaki (JP); Toshihiro Hatanaka, Kawasaki (JP); Ryusuke Hirama, Kawasaki (JP); Yoko Kageyama, Kawasaki (JP); Nobuo Kondo, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1492 days.

(21) Appl. No.: 10/972,743

(22) Filed: Oct. 26, 2004

(65) Prior Publication Data

US 2005/0143424 A1 Jun. 30, 2005

Related U.S. Application Data

(63) Continuation of application No. PCT/JP03/05318, filed on Apr. 25, 2003.

(30) Foreign Application Priority Data

Apr. 26, 2002 (JP) ................................. 2002-127691

(51) Int. Cl.
*A01N 43/04* (2006.01)
*A01N 47/34* (2006.01)
*A01N 37/52* (2006.01)
*A01N 33/02* (2006.01)
*A61K 31/70* (2006.01)

(52) U.S. Cl. ............ 514/27; 514/25; 514/592; 514/635; 514/649

(58) Field of Classification Search .................. None
See application file for complete search history.

(56) References Cited

U.S. PATENT DOCUMENTS

| | | | |
|---|---|---|---|
| 6,683,056 B2 * | 1/2004 | Washburn et al. | 514/25 |
| 6,815,428 B2 | 11/2004 | Ohsumi et al. | |
| 6,908,905 B2 | 6/2005 | Ohsumi et al. | |
| 7,015,201 B2 | 3/2006 | Ohsumi et al. | |
| 7,045,665 B2 | 5/2006 | Fujikura et al. | |
| 7,084,123 B2 | 8/2006 | Fujikura et al. | |
| 7,087,579 B2 | 8/2006 | Nishimura et al. | |
| 7,189,702 B2 | 3/2007 | Nishimura et al. | |
| 7,217,697 B2 | 5/2007 | Shiohara et al. | |
| 7,247,616 B2 | 7/2007 | Ohsumi et al. | |
| 7,256,209 B2 | 8/2007 | Ohsumi et al. | |
| 7,294,618 B2 | 11/2007 | Fushimi et al. | |
| 7,393,838 B2 | 7/2008 | Fujikura et al. | |
| 7,429,568 B2 | 9/2008 | Fujikura et al. | |
| 7,465,712 B2 | 12/2008 | Fujikura et al. | |
| 7,465,713 B2 | 12/2008 | Fujikura et al. | |
| 2003/0087843 A1 | 5/2003 | Washburn | |
| 2004/0053855 A1 | 3/2004 | Fujikura et al. | |
| 2005/0075294 A1 | 4/2005 | Fujikura et al. | |
| 2005/0080022 A1 | 4/2005 | Fujikura et al. | |
| 2009/0093419 A1 | 4/2009 | Fujikura et al. | |

FOREIGN PATENT DOCUMENTS

| | | | |
|---|---|---|---|
| EP | 850948 | * | 1/1998 |
| EP | 0 850 948 A1 | | 7/1998 |
| JP | 2000/80041 | | 3/2000 |
| JP | 2003-12686 A | | 1/2003 |
| WO | WO 98/56378 | | 12/1998 |
| WO | WO 01/16147 | | 3/2001 |
| WO | WO 01/27128 | | 4/2001 |
| WO | WO 01/62295 | | 8/2001 |
| WO | WO 01/68660 A1 | | 9/2001 |
| WO | WO 02/36602 A1 | | 5/2002 |
| WO | WO 02/053573 A1 | | 7/2002 |
| WO | WO02/088157 | * | 7/2002 |
| WO | WO 02/068439 A1 | | 9/2002 |
| WO | WO 02/068440 A1 | | 9/2002 |
| WO | WO02/036602 | * | 10/2002 |
| WO | WO 02/088157 | | 11/2002 |
| WO | WO 02/098893 A1 | | 12/2002 |
| WO | WO 03/020737 A1 | | 3/2003 |

OTHER PUBLICATIONS

U.S. Appl. No. 11/774,102, filed Jul. 6, 2007, Ohsumi, et al.
A.J. Scheen, "Non-insulin-dependent diabetes mellitus in the elderly", Bailliere's Clinical Endocrinology and Metabolism, vol. 11, No. 2, Jul. 1997, 18 Pages.
Jay M. Sengewald, "Update on diabetes medications", Journal of Emergency Nursing, vol. 25, No. 1, 1999, pp. 28-30.
U.S. Appl. No. 12/621,626, filed Nov. 19, 2009, Ohsumi, et al.
Canadian Office Action issued Jan. 5, 2011 in Canadian Application No. 2,484,306 published Nov. 6, 2003.

\* cited by examiner

*Primary Examiner* — Traviss C McIntosh, III
(74) *Attorney, Agent, or Firm* — Oblon, Spivak, McClelland, Maier & Neustadt, L.L.P.

(57) ABSTRACT

The invention provides a prophylactic and therapeutic agent of diabetes mellitus, including a combination of an inhibitor of renal glucose reabsorption and a hypoglycemic agent. In accordance with the invention, hyperglycemia after meals, between meals and during fasting can be ameliorated. More specifically, in accordance with the invention, a therapeutic effect of diabetes mellitus as never been obtained by the hypoglycemic agents of the related art can be achieved.

27 Claims, 5 Drawing Sheets

PROPHYLACTIC AND THERAPEUTIC AGENT OF DIABETES MELLITUS

CROSS-REFERENCE TO A RELATED APPLICATION

The present application is a continuation of International Application PCT/JP03/05318, filed on Apr. 25, 2003, which claims priority to Japanese Patent Application No. JP 2002-127691, filed on Apr. 26, 2002.

TECHNICAL FIELD

The present invention relates to a novel prophylactic and therapeutic agent of diabetes mellitus, specifically a prophylactic and therapeutic agent of diabetes mellitus, including a combination of an inhibitor of renal glucose reabsorption and a hypoglycemic agent as well as a prophylactic or therapeutic method of diabetes mellitus, using a combination of an inhibitor of renal glucose reabsorption and a hypoglycemic agent.

BACKGROUND OF THE INVENTION

Diabetes mellitus is a metabolic disease involving the increase of the level of blood glucose above the range of normal subjects due to the quantitative insufficiency or functional insufficiency of insulin in bodies, so that healthy life is markedly deteriorated because of microangiopathy in kidney, retina, nerve and the like and great vessel disorders such as arteriosclerosis. Hypoglycemic agents including insulin, insulin secretion-promoting agents, insulin resistance-ameliorating agents and α-glucosidase inhibitors have been widely applied so far for clinical therapeutic methods. However, these individual hypoglycemic agents have their unique problems although their usefulness is noted. For example, the effectiveness of insulin secretion-promoting agents and insulin resistance-ameliorating agents is greatly reduced in diabetic patients with severely deteriorated insulin secretion potencies of their pancreas. In diabetic patients with prominent insulin resistance, the effectiveness of insulin and insulin secretion-promoting agents is lowered. Hyperglycemic state exists in diabetic patients after meals, between meals and during fasting, namely throughout a day, compared with normal subjects. The hyperglycemic state throughout a day should be corrected as much as possible as a whole.

However, existing hypoglycemic agents have unique characteristic features of their hypoglycemic actions and cannot suppress abnormal increase in blood glucose throughout a day. For example, large-scale trial reports tell that insulin or insulin secretion-promoting agents cannot completely normalize the pattern of blood glucose variation throughout a day during the life cycles of diabetic patients, so that insulin or insulin secretion-promoting agents cannot absolutely prevent the onset of diabetic complications.

α-Glucosidase inhibitors and nateglinide and repaglinide are now used as agents for ameliorating hyperglycemia after meals. However, the hypoglycemic actions thereof are hardly sustainable in several hours after meals. As to other hypoglycemic agents, any action to immediately lower the increase in blood glucose due to meals cannot be counted thereon. As described above, the existing hypoglycemic agents cannot completely normalize the pattern of blood glucose variation throughout a day during the life cycles of diabetic patients. At a current state, therefore, expectations exist for the development of a prophylactic and therapeutic agent of diabetes mellitus, which can overcome these problems, particularly which can normalize the pattern of blood glucose variation throughout a day, as well as a prophylactic and therapeutic agent of diabetes mellitus, which is applicable to diabetic patients for whom the existing anti-diabetic agents have only poor effects.

DISCLOSURE OF THE INVENTION

It is an object of the invention to develop a great prophylactic and therapeutic agent of diabetes mellitus. Specifically, it is an object of the invention to provide a prophylactic and therapeutic agent of diabetes mellitus, with a therapeutic effect on diabetes mellitus as has never been obtained by hypoglycemic agents of the related art, particularly with an ability to normalize the pattern of blood glucose variation throughout a day.

The present inventors have made investigations so as to overcome the problems described above. Consequently, the inventors have found that the use of a combination of a hypoglycemic agent and an inhibitor of renal glucose reabsorption can produce a marked therapeutic effect, particularly a hypoglycemic action, from the standpoint of anti-diabetic action compared with no use thereof and that the use thereof can satisfy the demands due to the problems. Thus, the invention has been achieved.

The invention is described in more detail herein below.

Hypoglycemic agents can be divided into agents suppressing hyperglycemia after meals or agents never suppressing hyperglycemia after meals. It has been shown that the suppression of not only fasting blood glucose but also postprandial hyperglycemia is important for the therapeutic treatment of diabetes mellitus. The inventors have examined whether or not individual combinations of an agent with a strong suppressive action of hyperglycemia after meals or an agent without such action among the existing hypoglycemic agents with an inhibitor of renal glucose reabsorption can more strictly control blood glucose in model animals. Consequently, the inventors have found that a combined use of any hypoglycemic agent with an inhibitor of renal glucose reabsorption can produce a therapeutic effect never obtained by the elevation of the dose of a single one agent, i.e. that such combined use can ameliorate the pattern of blood glucose variation throughout a day.

Namely, the combined use can lower both the high blood glucose level immediately after glucose loading as a model of hyperglycemia after meals and the blood glucose level after a time passes after glucose loading. In that case, pharmaceutical agents highly effectively used in combination with an inhibitor of renal glucose reabsorption were not limited to a single one category. For the purpose of examining whether or not the prophylactic and therapeutic agent of the inventors would be essentially effective as the therapeutic treatment of diabetes mellitus, further, the inventors gave the combination agent to a type 2 diabetic model animals for a long period of time. By the therapeutic method with combinations of inhibitors of renal glucose reabsorption and the existing hypoglycemic agents, the diseased conditions of the diabetic model animal were greatly ameliorated, compared with therapeutic methods with no use of such combination.

Based on the results described above, the inventors have shown that the invention is more effective than therapeutic remedies using only existing hypoglycemic agents. Thus, the invention has been achieved.

The invention is described as follows.

[1] A prophylactic and therapeutic agent of diabetes mellitus, including a combination of an inhibitor of renal glucose reabsorption and a hypoglycemic agent.

[2] A prophylactic and therapeutic agent of diabetes mellitus in [1], where the hypoglycemic agent is at least one selected from insulin preparations, insulin derivatives, insulin secretion-promoting agents, insulin resistance-ameliorating agents, insulin mimetics, α-glucosidase inhibitors and glucogenesis inhibitors.

[3] A prophylactic and therapeutic agent of diabetes mellitus in [1], where the hypoglycemic agent is at least one selected from sulfonylureas, meglitinide analogues and biguanides.

[4] A prophylactic and therapeutic agent of diabetes mellitus in [1], where the hypoglycemic agent is at least one selected from sulfonylureas and biguanides.

[5] A prophylactic and therapeutic agent of diabetes mellitus in [4], where the sulfonylureas are at least one selected from tolbutamide, chlorpropamide, glibenclamide, glipizide, glimeperide and gliclazide and where the biguanides are at least one selected from metformin, phenformin and buformin.

[6] A prophylactic and therapeutic agent of diabetes mellitus in [1], where the hypoglycemic agent is meglitinide analogues.

[7] A prophylactic and therapeutic agent of diabetes mellitus in [6], where the meglitinide analogues are at least one selected from repaglinide, nateglinide, meglitinide and mitiglinide.

[8] A prophylactic and therapeutic agent of diabetes mellitus in [1], where the hypoglycemic agent is glibenclamide.

[9] A prophylactic and therapeutic agent of diabetes mellitus in [1], where the hypoglycemic agent is metformin.

[10] A prophylactic and therapeutic agent of diabetes mellitus in [1], where the hypoglycemic agent is repaglinide.

[11] A prophylactic and therapeutic agent of diabetes mellitus in [1], where the hypoglycemic agent is nateglinide.

[12] A prophylactic and therapeutic agent of diabetes mellitus in [1], where the hypoglycemic agent is mitiglinide.

[13] A prophylactic and therapeutic agent of diabetes mellitus in any of [1] through [12], where the inhibitor of renal glucose reabsorption is at least one selected from pyrazole derivatives represented by the following general formulas (1) and (2) and pharmaceutically acceptable salts thereof:

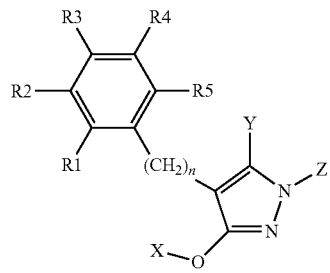

(1)

[in the formula, X represents β-D-glucopyranosyl group (where one or plural hydroxyl groups may be acylated);

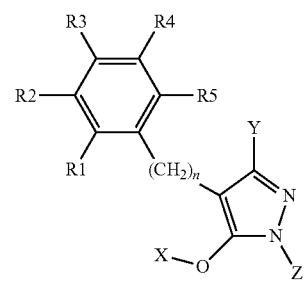

(2)

Y represents a lower alkyl group, a fluoro-lower alkyl group or a perfluoro-lower alkyl group;

Z represents an optionally substituted cyclic alkyl group, an optionally substituted cyclic unsaturated alkyl group, a lower alkyl group with unsaturated bond, a lower alkyl group with an optionally substituted cyclic alkyl group or a lower alkyl group with an optionally substituted cyclic unsaturated alkyl group;

R1 through R5 may be the same or different and represent hydrogen atom, a lower alkyl group, a fluoro-lower alkyl group, a perfluoro-lower alkyl group, a lower alkoxy group, a fluoro-lower alkoxy group, a perfluoro-lower alkoxy group, a lower alkylthio group, a fluoro-lower alkylthio group, a perfluoro-lower alkylthio group, a lower alkylamino group, a halogeno group, a lower alkanoyl group, an alkenyl group, a cyclic alkenyl group, an alkynyl group, an optionally substituted aralkyl group, optionally substituted phenyl group or a lower alkoxy-carbonyl group; and n represents an integer of 0 to 3.]

[14] A prophylactic and therapeutic agent of diabetes mellitus in [13], where the inhibitor of renal glucose reabsorption is at least one selected from pyrazole derivatives where Z is an optionally substituted cyclic alkyl group in the general formulas (1) and (2) and pharmaceutically acceptable salts thereof.

[15] A prophylactic and therapeutic agent of diabetes mellitus in [13], where the inhibitor of renal glucose reabsorption is at least one selected from pyrazole derivatives where Y is trifluoromethyl group in the general formulas (1) and (2) and pharmaceutically acceptable salts thereof.

[16] A prophylactic and therapeutic agent of diabetes mellitus in [13], where the inhibitor of renal glucose reabsorption is at least one selected from pyrazole derivatives where Y is trifluoromethyl group and n is 1 in the general formulas (1) and (2) and pharmaceutically acceptable salts thereof.

[17] A prophylactic and therapeutic agent of diabetes mellitus in [13], where the inhibitor of renal glucose reabsorption is at least one selected from pyrazole derivatives where Y is trifluoromethyl group; n is 1; and X is β-D-glucopyranosyl group (where one or plural hydroxyl groups may be acylated with a group or groups selected from alkanoyl groups with 2 to 20 carbon atoms, lower alkoxy-carbonyl groups and benzoyl group) in the general formulas (1) and (2) and pharmaceutically acceptable salts thereof.

[18] A prophylactic and therapeutic agent of diabetes mellitus in [13], where the inhibitor of renal glucose reabsorption is at least one selected from pyrazole derivatives represented by the following formulas (3), (3a), (4) and (4a) and pharmaceutically acceptable salts thereof:

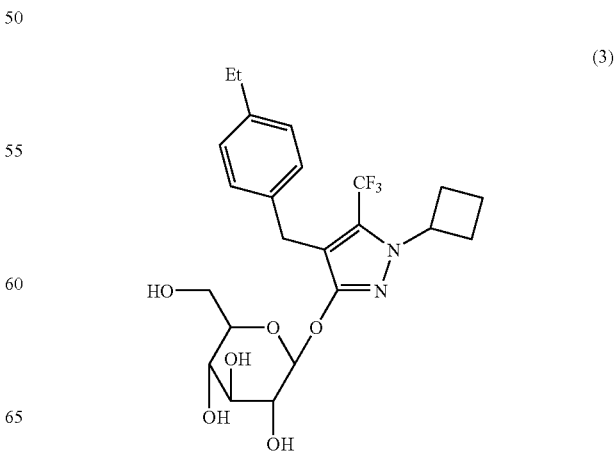

(3)

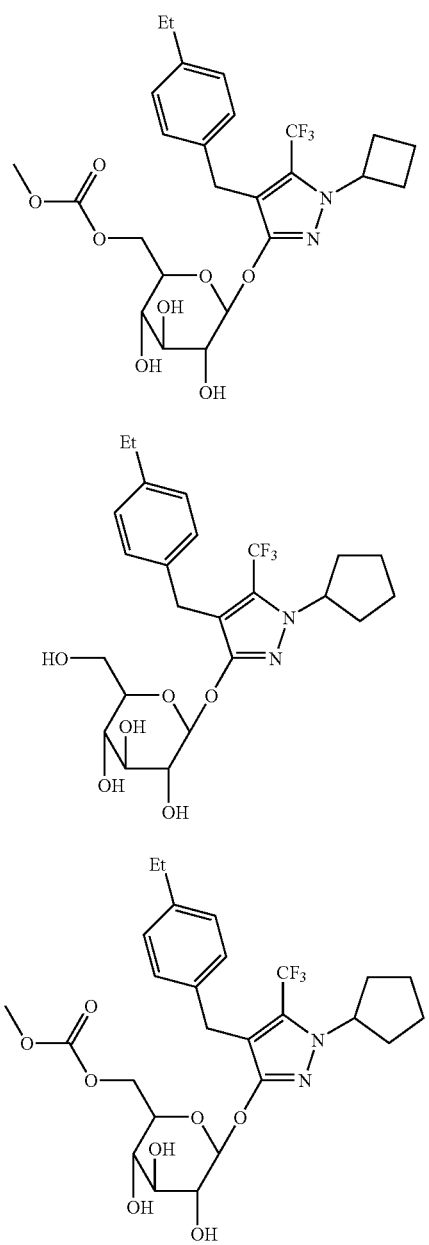

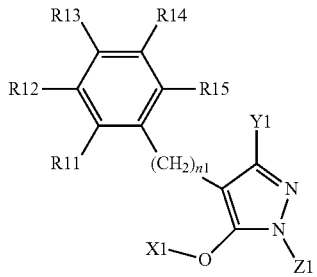

[in the formulas, X1 represents β-D-glucopyranosyl group (where one or plural hydroxyl groups may be acylated) or β-D-glucuronyl group (where one or plural hydroxyl groups may be acylated and carboxyl group may be esterified);

Y1 represents a lower alkyl group or a perfluoro-lower alkyl group;

Z1 represents hydrogen atom, a lower alkyl group, a perfluoro-lower alkyl group, an optionally substituted aralkyl group or optionally substituted phenyl group;

R11 through R15 may be the same or different and represent hydrogen atom, a lower alkyl group, a perfluoro-lower alkyl group, a lower alkoxy group, a perfluoro-lower alkoxy group, a lower alkylthio group, a perfluoro-lower alkylthio group, a lower alkylamino group, a halogeno group, a lower alkanoyl group, a lower alkenyl group or a lower alkynyl group; and n1 represents an integer of 0 to 3.]

[20] A prophylactic and therapeutic agent of diabetes mellitus in [19], where the inhibitor of renal glucose reabsorption is at least one selected from pyrazole derivatives where at least one of R11 through R15 is a lower alkyl group, a perfluoro-lower alkyl group, a lower alkoxy group, a perfluoro-lower alkoxy group, a lower alkylthio group, a perfluoro-lower alkylthio group, a lower alkylamino group, a halogeno group, a lower alkanoyl group, a lower alkenyl group or a lower alkynyl group in the general formulas (1A) and (2A) and pharmaceutically acceptable salts thereof.

[21] A prophylactic and therapeutic agent of diabetes mellitus in [19], where the inhibitor of renal glucose reabsorption is at least one selected from pyrazole derivatives where at least one of R11, R12, R14 and R15 is a halogeno group in the general formulas (1A) and (2A) and pharmaceutically acceptable salts thereof.

[22] A prophylactic and therapeutic agent of diabetes mellitus in [19], where the inhibitor of renal glucose reabsorption is at least one selected from pyrazole derivatives where Y1 is trifluoromethyl group in the general formulas (1A) and (2A) and pharmaceutically acceptable salts thereof.

[23] A prophylactic and therapeutic agent of diabetes mellitus in [19], where the inhibitor of renal glucose reabsorption is at least one selected from pyrazole derivatives where Y1 is trifluoromethyl group and n1 is 1 in the general formulas (1A) and (2A) and pharmaceutically acceptable salts thereof.

[24] A prophylactic and therapeutic agent of diabetes mellitus in [19], where the inhibitor of renal glucose reabsorption is at least one selected from pyrazole derivatives where Y1 is trifluoromethyl group; n1 is 1; and X1 is β-D-glucopyranosyl group (where one or plural hydroxyl groups may be acylated with a group or groups selected from alkanoyl groups with 2 to 20 carbon atoms, lower alkoxy-carbonyl groups and benzoyl group) in the general formulas (1A) and (2A) and pharmaceutically acceptable salts thereof.

[19] A prophylactic and therapeutic agent of diabetes mellitus in any of [1] through [12], where the inhibitor of renal glucose reabsorption is at least one selected from pyrazole derivatives represented by the following formulas (1A) and (2A) and pharmaceutically acceptable salts thereof:

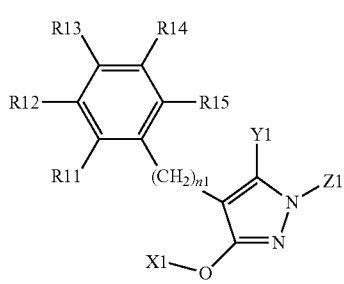

[25] A prophylactic and therapeutic agent of diabetes mellitus in [19], where the inhibitor of renal glucose reabsorption is at least one selected from pyrazole derivatives where Y1 is trifluoromethyl group; n1 is 1; and X1 is β-D-glucuronyl group (where one or plural hydroxyl groups may be acylated with a group or groups selected from alkanoyl groups with 2 to 20 carbon atoms, lower alkoxy-carbonyl groups and benzoyl group and where carboxyl group may be esterified with a lower alkyl group) in the general formulas (1A) and (2A) and pharmaceutically acceptable salts thereof.

[26] A prophylactic and therapeutic agent of diabetes mellitus in [19], where the inhibitor of renal glucose reabsorption is at least one selected from pyrazole derivatives represented by the following formulas (3A), (4A), (10-A), (12-A), (14-A) and (16-A) and pharmaceutically acceptable salts thereof:

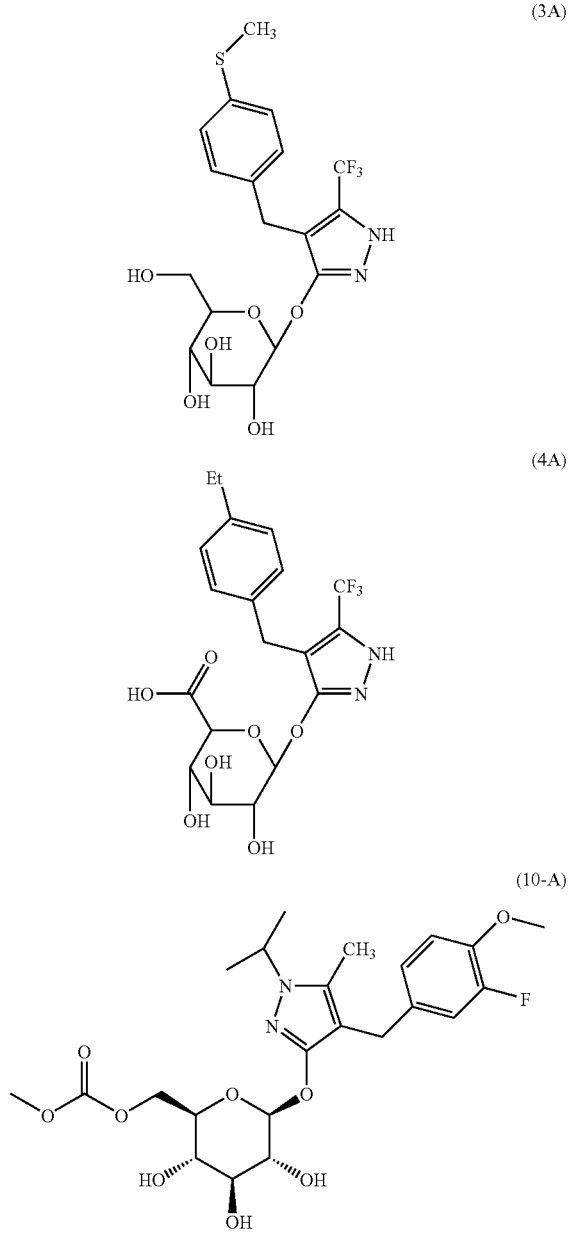

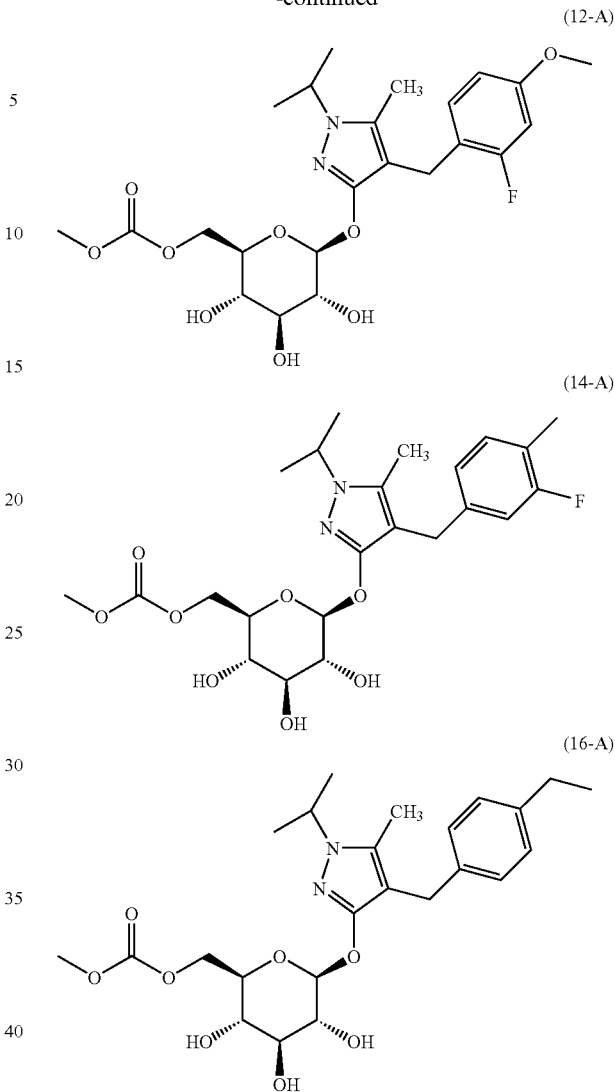

[27] A prophylactic and therapeutic agent of diabetes mellitus in any of [1] through [12], where the inhibitor of renal glucose reabsorption is at least one selected from pyrazole-o-glycoside derivatives represented by the following general formula (5) and pharmaceutically acceptable salts thereof:

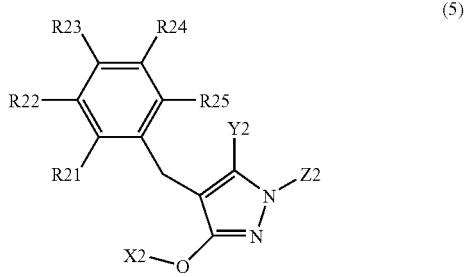

[in the formula, X2 represents β-D-glucopyranosyl group (where one or plural hydroxyl groups may be acylated);
Y2 represents hydrogen, a lower alkyl group, a fluoro-lower alkyl group or a perfluoro-lower alkyl group;
Z2 represents a halo-lower alkyl group;
R21 through R25 may be the same or different and represent hydrogen atom, a halogeno group, a lower alkyl group, a halo-lower alkyl group, a perfluoro-lower alkyl group, a lower alkoxy group, a perfluoro-lower alkoxy group, a lower alkylthio group, a perfluoro-lower alkylthio group, a lower alkylamino group, a lower alkanoyl group, a lower alkenyl group, a lower alkynyl group or an optionally substituted aralkyl group.]

[28] A prophylactic and therapeutic agent of diabetes mellitus in [27], where the inhibitor of renal glucose reabsorption is at least one selected from pyrazole-o-glycoside derivatives where Z2 is a halo-lower alkyl group; Y2 is trifluoromethyl group; and X2 is β-D-glucopyranosyl group (where one or plural hydroxyl groups may be acylated with a group or groups selected from alkanoyl groups with 2 to 20 carbon atoms, lower alkoxy-carbonyl groups and benzoyl group) in the general formula (5) and pharmaceutically acceptable salts thereof.

[29] A prophylactic and therapeutic agent of diabetes mellitus in [27], where the inhibitor of renal glucose reabsorption is at least one selected from pyrazole-o-glycoside derivatives where Z2 is a fluoro-lower alkyl group; Y2 is trifluoromethyl group; and X2 is β-D-glucopyranosyl group (where one or plural hydroxyl groups may be acylated with a group or groups selected from alkanoyl groups with 2 to 20 carbon atoms, lower alkoxy-carbonyl groups and benzoyl group) in the general formula (5) and pharmaceutically acceptable salts thereof.

[30] A prophylactic and therapeutic agent of diabetes mellitus in [27], where the inhibitor of renal glucose reabsorption is at least one selected from pyrazole-o-glycoside derivatives where Z2 is a halo-lower alkyl group;

Y2 is methyl group; and X2 is β-D-glucopyranosyl group (where one or plural hydroxyl groups may be acylated with a group or groups selected from alkanoyl groups with 2 to 20 carbon atoms, lower alkoxy-carbonyl groups and benzoyl group) in the general formula (5) and pharmaceutically acceptable salts thereof.

[31] A prophylactic and therapeutic agent of diabetes mellitus in [27], where the inhibitor of renal glucose reabsorption is at least one selected from pyrazole-o-glycoside derivatives where Z2 is a fluoro-lower alkyl group;

Y2 is methyl group; and X2 is β-D-glucopyranosyl group (where one or plural hydroxyl groups may be acylated with a group or groups selected from alkanoyl groups with 2 to 20 carbon atoms, lower alkoxy-carbonyl groups and benzoyl group) in the general formula (5) and pharmaceutically acceptable salts thereof.

[32] A prophylactic and therapeutic agent of diabetes mellitus in [27], where the inhibitor of renal glucose reabsorption is at least one selected from compounds represented by the following formulas (6) and (7) and pharmaceutically acceptable salts thereof:

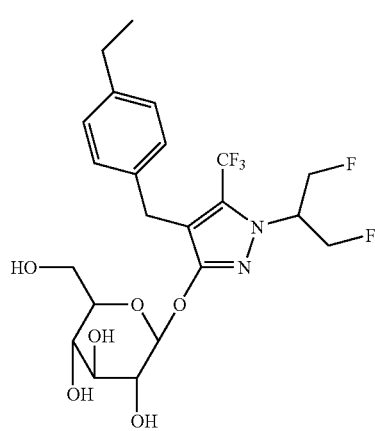

(6)

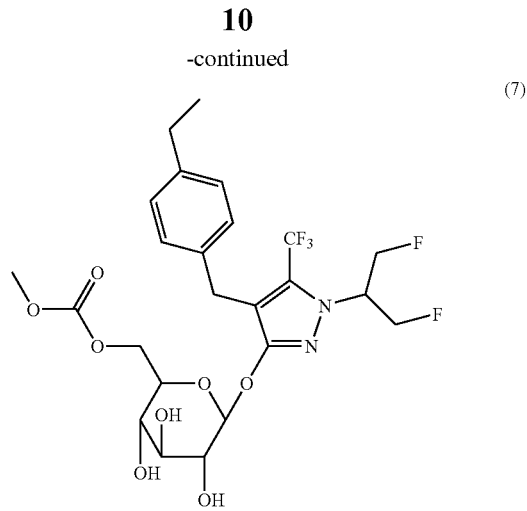

(7)

[33] A prophylactic and therapeutic agent of diabetes mellitus in any of [1] through [12], where the inhibitor of renal glucose reabsorption is at least one selected from glucopyranosyloxypyrazole derivatives represented by the following general formula (8) and pharmaceutically acceptable salts thereof:

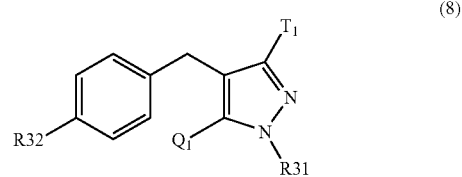

(8)

[in the formula, R31 is hydrogen atom or a lower alkyl group; either one of $Q_1$ and $T_1$ is a group represented by the formula (9):

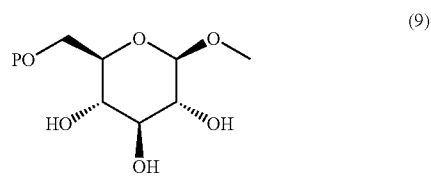

(9)

(where P represents hydrogen atom, a lower acyl group, a lower alkoxy-lower acyl group, a lower alkoxy-carbonyl-lower acyl group, a lower alkoxy-carbonyl group or a lower alkoxy-lower alkoxy-carbonyl group) and the other is a lower alkyl group or a halo-lower alkyl group;

R32 is hydrogen atom, a lower alkyl group, a lower alkoxy group, a lower alkylthio group, a halo-lower alkyl group or a halogen atom.]

[34] A prophylactic and therapeutic agent of diabetes mellitus in any of [1] through [12], where the inhibitor of renal glucose reabsorption is at least one selected from glucopyranosyloxybenzylbenzene derivatives represented by the following general formula (10) and pharmaceutically acceptable salts thereof:

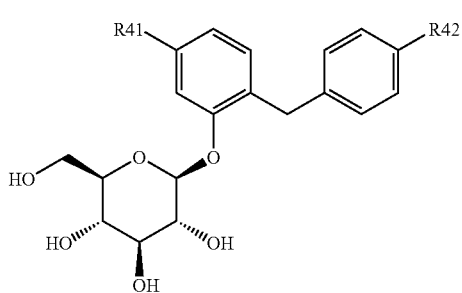
(10)

[where R41 is hydrogen atom or a hydroxy-lower alkyl group; R42 is a lower alkyl group, a lower alkoxy group, a lower alkylthio group, a hydroxy-lower alkyl group, a hydroxy-lower alkoxy group, a hydroxy-lower alkylthio group, a lower alkoxy-lower alkyl group, a lower alkoxy-lower alkoxy group or a lower alkoxy-lower alkylthio group.]

[35] A prophylactic and therapeutic agent of diabetes mellitus in any of [1] through [12], where the inhibitor of renal glucose reabsorption is at least one selected from compounds represented by the following general formula (11) and pharmaceutically acceptable salts thereof:

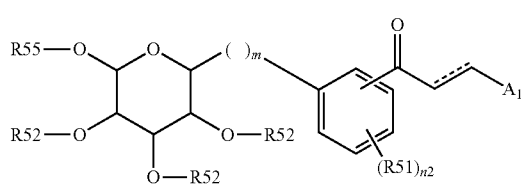
(11)

[where R51 represents hydrogen, hydroxyl group, a lower alkyl, lower alkoxy or

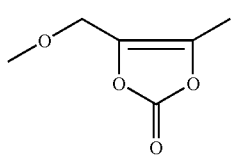
(12)

R52 represents hydrogen, —COO— lower alkyl,

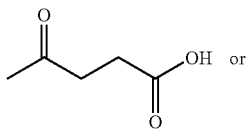
(13)

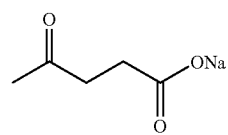
(14)

R55 represents hydroxymethyl, —CH$_2$OCOO— lower alkyl,

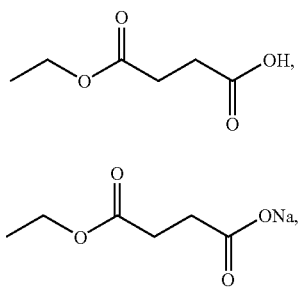
(15)

(16)

—CH$_2$OSO$_3$H, —COOH, —COONa;

m represents 0 or 1;

n2 represents 0, 1, 2 or 3;

A$_1$ represents the following cyclic structure:

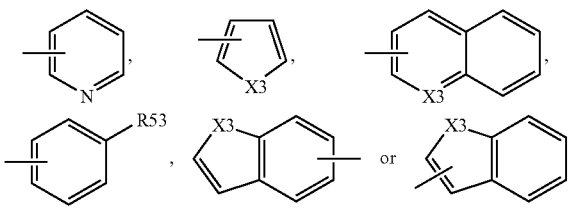

(where X3 represents oxygen, nitrogen or sulfur; when m is 0, R53 is a lower alkyl; when m is 1, R53 is a lower alkyl, hydroxyl group or a lower alkoxy group);

- - - - - represents single bond or double bond.]

[36] A prophylactic and therapeutic agent of diabetes mellitus in any of [1] through [12], where the inhibitor of renal glucose reabsorption is at least one selected from propiophenone derivatives represented by the following general formula (22) and pharmaceutically acceptable salts thereof:

(22)

[in the formula, OX4 represents hydroxyl group optionally protected;

Y4 represents a lower alkyl group;

Z4 represents β-D-glucopyranosyl group where one or plural hydroxyl groups may be protected.]

[37] A prophylactic and therapeutic agent of diabetes mellitus in [1], where the inhibitor of renal glucose reabsorption is at least one selected from (i) pyrazole derivatives represented by the following general formulas (1) and (2) and pharmaceutically acceptable salts thereof:

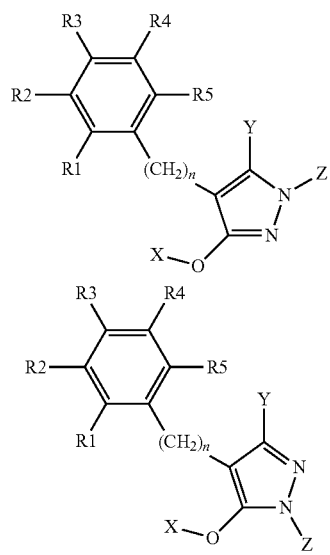

[in the formula, the individual symbols are as described in [13]];

(ii) pyrazole derivatives represented by the following general formulas (1A) and (2A) and pharmaceutically acceptable salts thereof:

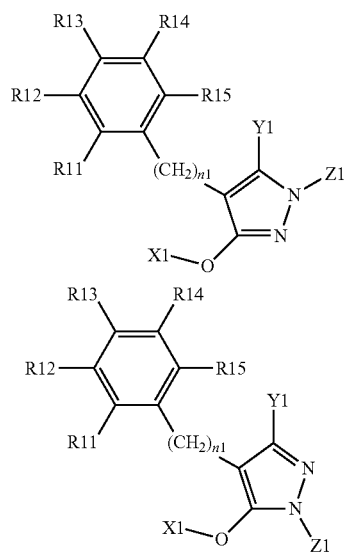

[in the formula, the individual symbols are as described in [19]];

(iii) pyrazole-o-glycoside derivatives represented by the following general formula (5) and pharmaceutically acceptable salts thereof:

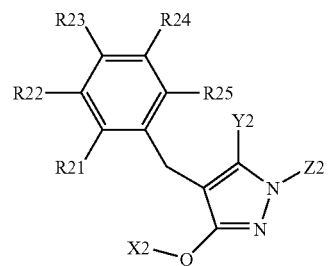

[in the formula, the individual symbols are as described in [27]]; and (iv) glucopyranosyloxypyrazole derivatives represented by the following general formula (8) and pharmaceutically acceptable salts thereof:

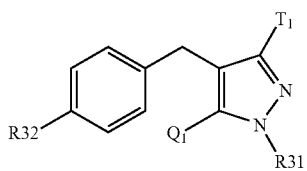

[in the formula, the individual symbols are as described in [33]]; and where the hypoglycemic agent is at least one selected from sulfonylureas and biguanides.

[38] A prophylactic and therapeutic agent of diabetes mellitus in [37], where the inhibitor of renal glucose reabsorption is at least one selected from pyrazole derivatives represented by the following formulas (3), (3a), (4a), (7), (10-A), (12-A), (14-A) and (16-A) and pharmaceutically acceptable salts thereof:

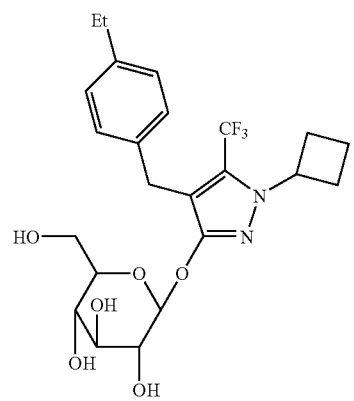

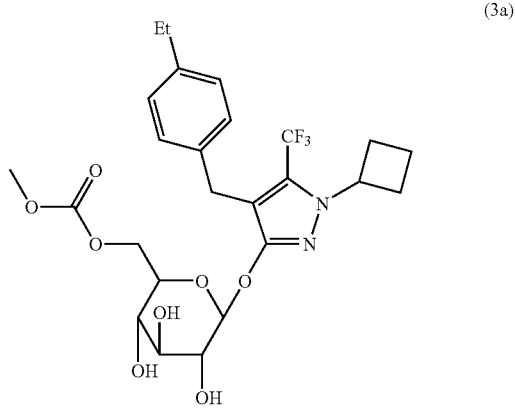

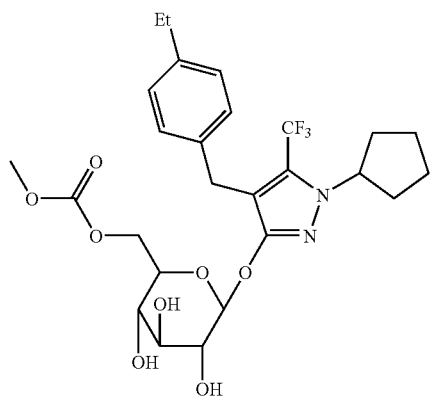

(4a)

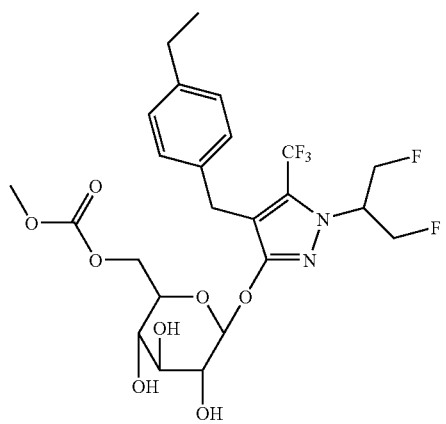

(7)

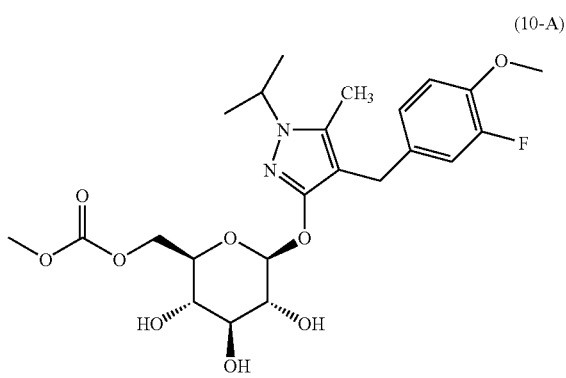

(10-A)

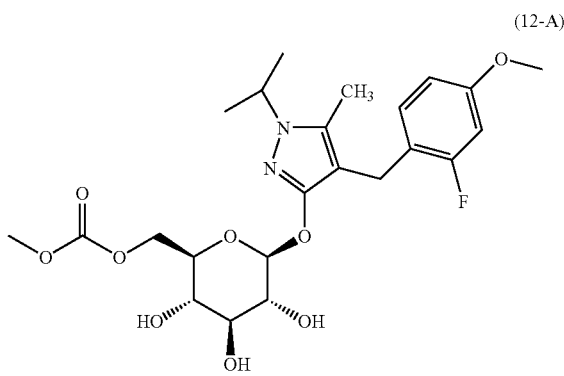

(12-A)

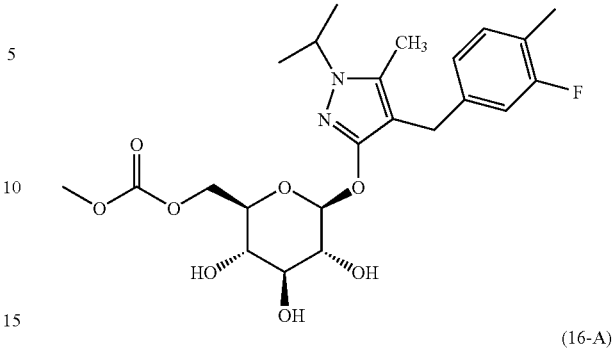

(14-A)

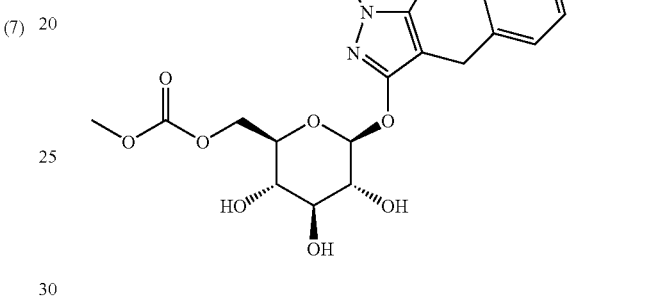

(16-A)

[39] A prophylactic and therapeutic agent of diabetes mellitus in [37] or [38], where the sulfonylureas are at least one selected from tolbutamide, chlorpropamide, glibenclamide, glipizide, glimeperide and gliclazide and the biguanides are at least one selected from metformin, phenformin and buformin.

[40] A prophylactic and therapeutic agent of diabetes mellitus in [1], where the inhibitor of renal glucose reabsorption is at least one selected from propiophenone derivatives represented by the following general formula (22) and pharmaceutically acceptable salts thereof and where the hypoglycemic agent is meglitinide analogues:

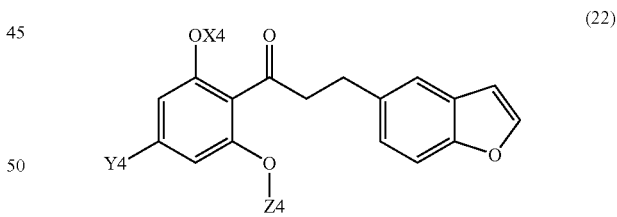

(22)

[in the formula, the individual symbols are as described in [36].]

[41] A prophylactic and therapeutic agent of diabetes mellitus in [40], where the inhibitor of renal glucose reabsorption is at least one selected from 3-(5-benzo[b]furanyl)-2'-(6-o-methoxycarbonyl-β-D-glucopyranosyloxy)-6'-hydroxy-4'-methylpropiophenone and pharmaceutically acceptable salts thereof.

[42] A prophylactic and therapeutic agent of diabetes mellitus in [40] or [41], where the meglitinide analogues are at least one selected from repaglinide, nateglinide, meglitinide and mitiglinide.

[43] A prophylactic and therapeutic method of diabetes mellitus, including administering a combination of an effective dose of an inhibitor of renal glucose reabsorption and an effective dose of a hypoglycemic agent to mammals.

[44] A use of an inhibitor of renal glucose reabsorption and a hypoglycemic agent for producing a prophylactic and therapeutic agent of diabetes mellitus.

[45] A commercial package including a combination agent including a combination of an inhibitor of renal glucose reabsorption and a hypoglycemic agent and an instruction insert about the combination agent, telling that the combination agent can be or should be used for prophylactic and therapeutic treatment of diabetes mellitus.

DETAILED DESCRIPTION OF THE INVENTION

Figure 1:
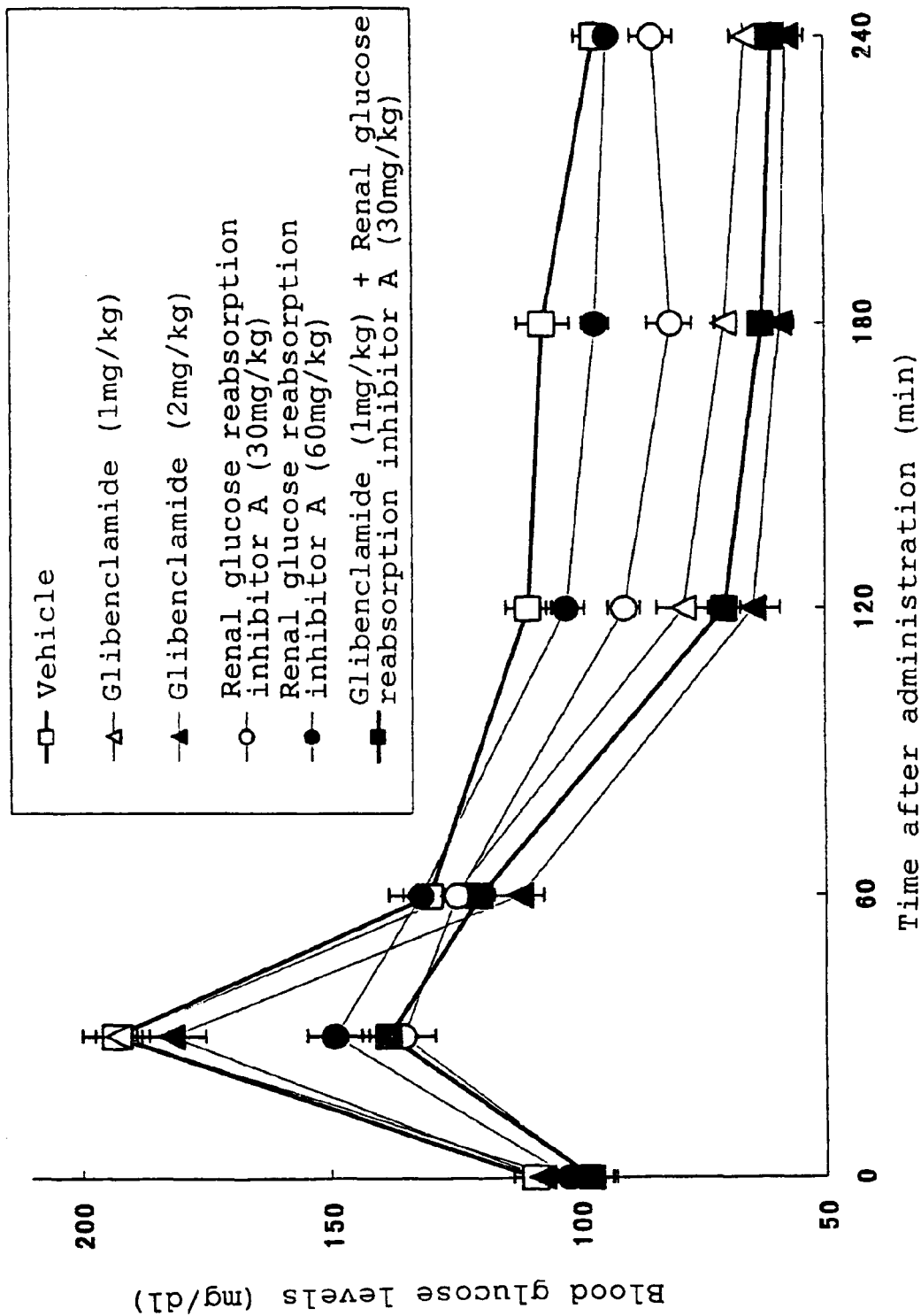
FIG. 1 shows graphs depicting the effect of a combined use of glibenclamide and an inhibitor A of renal glucose reabsorption in Example I (mean±standard deviation; N=6 in each group)

The prophylactic and therapeutic agent of diabetes mellitus of the invention includes a combination of an inhibitor of renal glucose reabsorption and a hypoglycemic agent (namely, a combination agent). As the prophylactic and therapeutic agent in accordance with the invention, therefore, any inhibitor of renal glucose reabsorption and any hypoglycemic agent are satisfactory, if these agents can be used in combination at the time of administration. Thus, the prophylactic and therapeutic agent of diabetes mellitus in accordance with the invention may be a single one preparation obtained by formulating together an inhibitor of renal glucose reabsorption and a hypoglycemic agent or may be a combination of at least two types of preparations obtained by separately formulating an inhibitor of renal glucose reabsorption and a hypoglycemic agent, as long as the inhibitor of renal glucose reabsorption and the hypoglycemic agent can be used in combination at the time of administration. For the prophylactic and therapeutic agent of diabetes mellitus in accordance with the invention, additionally, at least one inhibitor of renal glucose reabsorption and at least one hypoglycemic agent may satisfactorily be used in combination. Therefore, satisfactorily, two or more inhibitors of renal glucose reabsorption may be used, while two or more hypoglycemic agents may be used as well.

In accordance with the invention, the hypoglycemic agent means a pharmaceutical agent with a major physiological action of promotion of glucose uptake into target tissue cells or suppression of glucose absorption from intestinal tube or suppression of glucose synthesis in tissues to lower the glucose concentration in blood to ameliorate hyperglycemia, for use in the prophylaxis and therapeutic treatment of various diseased conditions because of hyperglycemia. The hypoglycemic agent includes for example insulin preparations, insulin derivatives, insulin mimetics, insulin secretion-promoting agents, insulin resistance-ameliorating agents, α-glucosidase inhibitors and glucogenesis inhibitors.

More specifically, the insulin preparations include for example NPH, Lente, Utralente and insulin which can be absorbed transpulmonarily.

The insulin derivatives mean insulin-derived proteins and peptides with insulin actions, and include for example lispro, B10Asp and HOE-901.

The insulin secretion-promoting agents exert their hypoglycemic action, by mainly influencing pancreatic β-cell to promote insulin secretion into blood, and include for example sulfonylureas (for example, tolbutamide, chlorpropamide, glibenclamide (glyburide), glipizide, glimeperide and gliclazide, preferably glibenclamide); and meglitinide analogues (for example, repaglinide, nateglinide, meglitinide and mitiglinide (KAD-1229), preferably nateglinide); other than sulfonylureas and meglitinide analogues, the insulin secretion-promoting agents additionally include for example $K^+$-ATP channel inhibitors (for example, BTS-67-582), glucagon-like peptide-1 receptor agonists (for example, glucagon-like peptide-1, exendin-4 and NN-2211) and dipeptidyl peptidase-IV inhibitors with an effect of enhancing the action of glucagon-like peptide-1. In accordance with the invention, sulfonylureas and meglitinide analogues are preferable.

The insulin resistance-ameliorating agents mean agents exerting the hypoglycemic action by enhancing the action of insulin in target tissues, and include for example peroxisome proliferator activator receptor (PPAR)-γ agonists (for example, thiazolidine-based compounds such as pioglitazone, rosiglitazone, ciglitazone and troglitazone; or non-thiazolidine-based compounds such as GI-262570, JTT-501, YM-440, NN-622 and KRP-297), PPAR-γ antagonists and protein tyrosine phosphatase inhibitors. In a broad sense, the insulin resistance-ameliorating agents include for example pharmaceutical agents with a function ameliorating insulin resistance, for example biguanides (for example, metformin, phenformin and buformin, preferably metformin), PPAR-α agonists (fibrate-series compounds such as simfibrate, clofibrate, bezafibrate and clinofibrate and non-fibrate-series compounds), anti-obesity agents (for example, 5-hydroxytryptamine reuptake inhibitors such as sibutramine, lipase inhibitors such as orlistat and adrenalin β-receptor agonists such as AJ-9677). In accordance with the invention, biguanides are preferable.

Insulin mimetics mean those expressing the hypoglycemic action through the physiological insulin action, namely the action promoting glucose uptake into cells, in a manner more or less independent to insulin, except for insulin derivatives, and include for example insulin receptor-activating agents (for example, CLX-0901 and L-783281) and vanadium.

α-Glucosidase inhibitors mean those expressing the hypoglycemic action through the suppression of glucose absorption into bodies, mainly via the inhibition of α-glucosidase in intestinal tube, and include for example acarbose, voglibose and miglitol.

Glucogenesis inhibitors mean those expressing the hypoglycemic action mainly through the inhibition of glucogenesis, and include for example glucagon secretion suppressors (for example, M&B-39890A and octreotide), fatty acid decomposition inhibitors (for example, nicotinic acid derivatives and carnitine palmitoyltransferase-1 inhibitor) and glucose-6-phosphatase inhibitors.

Additionally, hypoglycemic agents other than those listed above, anti-hyperlipemia agents (for example, HMG-CoA reductase inhibitors and LDL receptor inducers), hypotensive agents (for example, angiotensin converting enzyme inhibitors, angiotensin II receptor antagonists, β receptor antagonists, α1 antagonists and calcium antagonists) and the like are also encompassed within the scope of the invention, as long as they can be used in combination with inhibitors of renal glucose reabsorption as a prophylactic and therapeutic agent of diabetes mellitus for the purpose of lowering blood glucose level.

In accordance with the invention, preferably, the hypoglycemic agent is at least one selected from sulfonylureas, meglitinide analogues and biguanides. In an embodiment of the invention, additionally, the hypoglycemic agent is preferably at least one selected from sulfonylureas and biguanides.

In another embodiment of the invention, still additionally, the hypoglycemic agent is preferably meglitinide analogues.

In accordance with the invention, the inhibitor of renal glucose reabsorption has an action inhibiting glucose reabsorption in uriniferous tubules. Therefore, the primary action of the inhibitor of renal glucose reabsorption is not involved in the promotion of the uptake into target tissue cells, the suppression of the absorption from intestinal tube, or the hypoglycemic action via the suppression of the synthesis in tissues. The inhibitor of renal glucose reabsorption differs from the hypoglycemic agents described above in terms of this point.

As the inhibitor of renal glucose reabsorption, any inhibitor thereof is satisfactory when the inhibitor has the action, but preferably includes those described below:

(i) pyrazole derivatives represented by the general formulas (1) and (2) [sometimes referred to as Compounds (1) and (2) hereinbelow] and pharmaceutically acceptable salts thereof;

(ii) pyrazole derivatives represented by the general formulas (1A) and (2A) [sometimes referred to as Compounds (1A) and (2A) hereinbelow] and pharmaceutically acceptable salts thereof;

(iii) pyrazole-o-glycoside derivatives represented by the general formula (5) [sometimes referred to as Compound (5) hereinbelow] and pharmaceutically acceptable salts thereof;

(iv) glucopyranosyloxypyrazole derivatives represented by the general formula (8) [sometimes referred to as Compound (8)] and pharmaceutically acceptable salts thereof;

(v) glucopyranosyloxybenzylbenzene derivatives represented by the general formula (10) [sometimes referred to as Compound (10) hereinbelow] and pharmaceutically acceptable salts thereof;

(vi) compounds represented by the general formula (11) [sometimes referred to as Compound (11) hereinbelow] and pharmaceutically acceptable salts thereof; and (vii) propiophenone derivatives represented by the general formula (22) [sometimes referred to as Compound (22) hereinbelow] and pharmaceutically acceptable salts thereof.

More preferably, the Compounds (1) and (2), the Compounds (1A) and (2A), the Compound (5), the Compound (8) and the Compound (22) and pharmaceutically acceptable salts of these Compounds are listed, because these compounds and salts thereof are very useful for glycemic control when used in combination with hypoglycemic agents, compared with the single use of any of inhibitors of renal glucose reabsorption or hypoglycemic agents.

The preferable inhibitors of renal glucose reabsorption are now individually described below.

(i) Compounds (1) and (2) and pharmaceutically acceptable salts thereof

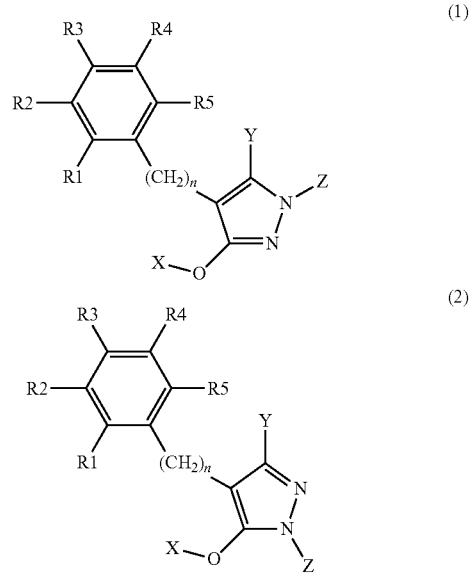

[in the formula, X represents β-D-glucopyranosyl group (where one or plural hydroxyl groups may be acylated);

Y represents a lower alkyl group, a fluoro-lower alkyl group or a perfluoro-lower alkyl group;

Z represents an optionally substituted cyclic alkyl group, an optionally substituted cyclic unsaturated alkyl group, a lower alkyl group with unsaturated bond, a lower alkyl group with an optionally substituted cyclic alkyl group or a lower alkyl group with an optionally substituted cyclic unsaturated alkyl group;

R1 through R5 may be the same or different and represent hydrogen atom, a lower alkyl group, a fluoro-lower alkyl group, a perfluoro-lower alkyl group, a lower alkoxy group, a fluoro-lower alkoxy group, a perfluoro-lower alkoxy group, a lower alkylthio group, a fluoro-lower alkylthio group, a perfluoro-lower alkylthio group, a lower alkylamino group, a halogeno group, a lower alkanoyl group, an alkenyl group, a cyclic alkenyl group, an alkynyl group, an optionally substituted aralkyl group, optionally substituted phenyl group or a lower alkoxy-carbonyl group; and n represents an integer of 0 to 3.]

The term "lower alkyl" in the Compounds (1) and (2) means alkyl groups with one to 6 carbon atoms.

The term "lower alkoxy" means alkoxy groups with one to 6 carbon atoms.

The term "lower alkanoyl" means alkanoyl groups with 2 to 6 carbon atoms.

Additionally, the "alkyl", "alkenyl" and "alkynyl" in the lower alkyl group, the perfluoro-lower alkyl group, the lower alkoxy group, the perfluoro-lower alkoxy group, the lower alkylthio group, the perfluoro-lower alkylthio group, the lower alkylamino group, the lower alkanoyl group, the alkenyl group, the alkynyl group and the lower alkoxy-carbonyl group may be linear or branched.

The lower alkyl group in the Compounds (1) and (2) includes for example methyl group, ethyl group, propyl group, butyl group, pentyl group, isopropyl group, isobutyl group and isopentyl group.

The fluoro-lower alkyl group in the Compounds (1) and (2) means lower alkyl groups where one or plural hydrogen atoms (but not all of the hydrogen atoms) are substituted with fluorine atoms, and includes for example monofluoromethyl group, difluoromethyl group, 2-fluoroethyl group, 2,2-difluoroethyl group, trifluoroethyl group (for example, 2,2,2-trifluoroethyl group), trifluoropropyl group (for example, 3,3,3-trifluoropropyl group and 1,1,1-trifluoro-2-propyl group), 1,3-difluoroisopropyl group and 1,1,1,3,3,3-hexafluoroisopropyl group, preferably trifluoroethyl group (for example, 2,2,2-trifluoroethyl group), trifluoropropyl group (for example, 3,3,3-trifluoropropyl group and 1,1,1-trifluoro-2-propyl group). Additionally, the number of fluorine atoms for substitution is preferably one to 6.

The perfluoro-lower alkyl group in the Compounds (1) and (2) means lower alkyl groups where all of the hydrogen atoms are substituted with fluorine atoms, and includes for example trifluoromethyl group, pentafluoroethyl group and heptafluoropropyl group, preferably trifluoromethyl group.

The lower alkoxy group in the Compounds (1) and (2) includes for example methoxy group, ethoxy group, propyloxy group and isopropyloxy group.

The fluoro-lower alkoxy group in the Compounds (1) and (2) means lower alkoxy groups where one or plural hydrogen atoms (but not all of the hydrogen atoms) are substituted with fluorine atoms, and includes for example monofluoromethoxy group, difluoromethoxy group, 2-fluoroethoxy group, 2,2-difluoroethoxy group, trifluoroethoxy group (for example, 2,2,2-trifluoroethoxy group), trifluoropropyloxy group (for example, 3,3,3-trifluoropropyloxy group, 1,1,1-trifluoro-2-propyloxy group), 1,3-difluoroisopropyloxy group and 1,1,1,3,3,3-hexafluoroisopropyloxy group, preferably trifluoroethoxy group (for example, 2,2,2-trifluoroethoxy group). Additionally, the number of fluorine atoms for substitution is preferably one to 6.

The perfluoro-lower alkoxy group in the Compounds (1) and (2) means lower alkoxy groups where all of the hydrogen atoms are substituted with fluorine atoms, and includes for example trifluoromethoxy group, pentafluoroethoxy group and heptafluoropropyloxy group, preferably trifluoromethoxy group.

The lower alkylthio group in the Compounds (1) and (2) includes for example methylthio group, ethylthio group and propylthio group.

The fluoro-lower alkylthio group in the Compounds (1) and (2) means lower alkylthio groups where one or plural hydrogen atoms (but not all of the hydrogen atoms) are substituted with fluorine atoms, and includes for example monofluoromethylthio group, difluoromethylthio group, 2-fluoroethylthio group, 2,2-difluoroethylthio group, trifluoroethylthio group (for example, 2,2,2-trifluoroethylthio group), trifluoropropylthio group (for example, 3,3,3-trifluoropropylthio group, 1,1,1-trifluoro-2-propylthio group), 1,3-difluoroisopropylthio group and 1,1,1,3,3,3-hexafluoroisopropylthio group, preferably trifluoroethylthio group (for example, 2,2,2-trifluoroethylthio group). Additionally, the number of fluorine atoms for substitution is preferably one to 6.

The perfluoro-lower alkylthio group in the Compounds (1) and (2) means lower alkylthio groups where all of the hydrogen atoms are substituted with fluorine atoms, and includes for example trifluoromethylthio group, pentafluoroethylthio group and heptafluoropropylthio group, preferably trifluoromethylthio group.

The lower alkylamino group in the Compounds (1) and (2) means methylamino group, ethylamino group, propylamino group, dimethylamino group and diethylamino group.

The halogeno group in the Compounds (1) and (2) includes for example fluorine atom, bromine atom, chlorine atom and iodine atom.

The lower alkanoyl group in the Compounds (1) and (2) includes for example acetyl group and propionyl group.

The alkenyl group in the Compounds (1) and (2) includes alkenyl groups with 2 to 6 carbon atoms, for example vinyl group, propenyl group and 2-methyl-1-propenyl group.

The cyclic alkenyl group in the Compounds (1) and (2) includes cyclic alkenyl groups with 5 to 10 carbon atoms, for example cyclopentenyl group and cyclohexenyl group.

The alkynyl group in the Compounds (1) and (2) includes alkynyl groups with 2 to 6 carbon atoms, for example ethynyl group.

The optionally substituted aralkyl group in the Compounds (1) and (2) includes optionally substituted aralkyl groups with 7 to 10 carbon atoms, for example benzyl group, benzyl group optionally substituted with one or two or more substituents on the benzene ring, phenethyl group and phenethyl group optionally substituted with one or two or more substituents on the benzene ring. Herein, the substituents for benzyl group and phenyl group include for example lower alkoxy groups, lower alkyl groups, halogeno groups and halogeno-lower alkyl groups. Additionally, the number of the substituents is preferably one to 3.

The substituents for the optionally substituted phenyl group in the Compounds (1) and (2) include for example lower alkoxy groups, lower alkyl groups, halogeno groups and halogeno-lower alkyl groups. Additionally, the number of the substituents is preferably one to 3.

The lower alkoxy-carbonyl group in the Compounds (1) and (2) includes for example methoxycarbonyl group, ethoxycarbonyl group and isopropoxycarbonyl group.

The "lower alkyl group with unsaturated bond" in the Compounds (1) and (2) includes C2 to C6 alkyl groups with unsaturated bond, for example allyl group and vinyl group.

The "optionally substituted cyclic alkyl group" in the Compounds (1) and (2) includes optionally substituted cyclic alkyl groups with 3 to 7 carbon atoms, for example cyclopropyl group, cyclobutyl group, cyclopentyl group, cyclohexyl group and cycloheptyl group, where these rings may be substituted with methyl group, ethyl group, methoxy group, ethoxy group, fluorine atom, chlorine atom and bromine atom. The number of substituents for the substitution of these rings is preferably one to 3.

The "optionally substituted cyclic unsaturated alkyl group" in the Compounds (1) and (2) includes optionally substituted cyclic unsaturated alkyl groups with 5 to 10 carbon atoms, for example cyclopentenyl group and cyclohexenyl group, where these rings may be substituted with methyl group, ethyl group, methoxy group, ethoxy group, fluorine atom, chlorine atom and bromine atom. The number of substituents for the substitution of these rings is preferably one to 3.

The "lower alkyl group with optionally substituted cyclic alkyl groups" in the Compounds (1) and (2) includes for example cyclobutylmethyl group, cyclobutylethyl group, cyclopentylmethyl group, cyclopentylethyl group, cyclohexylmethyl group and cyclohexylethyl group, where these rings may be substituted with methyl group, ethyl group, methoxy group, ethoxy group, fluorine atom, chlorine atom and bromine atom. Additionally, the number of substituents for the substitution of these rings is preferably one to 3.

The "lower alkyl group with optionally substituted cyclic unsaturated alkyl groups" in the Compounds (1) and (2) includes for example cyclopentenylmethyl group and cyclohexenylmethyl group, where these rings may be substituted with methyl group, ethyl group, methoxy group, ethoxy group, fluorine atom, chlorine atom and bromine atom. The number of substituents for the substitution of these rings is preferably one to 3.

The group for acylating the hydroxyl groups in the Compounds (1) and (2) includes for example acyl group and carbamate group. The acyl group includes for example acetyl group, propionyl group, benzoyl group and pivaloyl group. The carbamate group includes for example methyl carbonate group, ethyl carbonate group, propyl carbonate group, isopropyl carbonate group and phenyl carbonate group.

One or plural hydroxyl groups in β-D-glucopyranosyl group as the group represented as X in the Compounds (1) and (2) may be acylated. Particularly, one or plural hydroxyl groups in the group may be acylated with a group or groups selected from alkanoyl groups with 2 to 20 carbon atoms, lower alkoxy-carbonyl groups and benzoyl group. Such β-D-glucopyranosyl group includes for example 6-acetyl-β-D-glucopyranosyl group and 6-carbomethoxy-β-D-glucopyranosyl group. Further, the number of hydroxyl groups to be acylated is preferably one to 3.

The group represented as X in the Compounds (1) and (2) is particularly preferably β-D-glucopyranosyl group, 6-acetyl-β-D-glucopyranosyl group and 6-carbomethoxy-β-D-glucopyranosyl group. Further, the group is more preferably β-D-glucopyranosyl group.

The group represented as Y in the Compounds (1) and (2) is preferably perfluoro-lower alkyl groups with one to 6 carbon atoms, particularly preferably trifluoromethyl group.

Further, the group represented as Y in the Compounds (1) and (2) is additionally preferably a lower alkyl group with one to 6 carbon atoms. Particularly, methyl group is preferable.

The group represented as Z in the Compounds (1) and (2) is preferably an optionally substituted cyclic alkyl group, more preferably an optionally substituted cyclic alkyl group with 3 to 7 carbon atoms, particularly preferably cyclobutyl group and cyclopentyl group.

Additionally, the group represented as Z is preferably a lower alkyl group with unsaturated bond, more preferably a C2 to C6 alkyl group with unsaturated bond, particularly preferably allyl group and vinyl group.

Still additionally, the group represented by Z is preferably an optionally substituted cyclic unsaturated alkyl group, more preferably a C4 to C7 cyclic unsaturated alkyl group, particularly preferably cyclopentenyl group and cyclohexenyl group.

The groups represented as R1 through R5 in the Compounds (1) and (2) are preferably lower alkyl groups with one to 6 carbon atoms and lower alkylthio groups with one to 6 carbon atoms, particularly preferably methyl group, ethyl group, methylthio group and ethylthio group.

In the Compounds (1) and (2), n is particularly preferably an integer 1.

In the Compounds (1) and (2), Z is preferably an optionally substituted cyclic alkyl group.

In the Compounds (1) and (2), further, Y is preferably trifluoromethyl group.

In the Compounds (1) and (2), preferably, Y is trifluoromethyl group and n is 1.

In the Compounds (1) and (2), additionally preferably, Y is trifluoromethyl group; n is 1; and X is β-D-glucopyranosyl group (where one or plural hydroxyl groups may be acylated with a group or groups selected from alkanoyl groups with 2 to 20 carbon atoms, lower alkoxy-carbonyl groups and benzoyl group).

In the Compounds (1) and (2), additionally preferably, Y is trifluoromethyl group; n is 1; and X is β-D-glucopyranosyl group.

In the Compounds (1), additionally preferably, Y is trifluoromethyl group; n is 1; and X is 6-acetyl-β-D-glucopyranosyl group.

In the Compounds (1) and (2), additionally preferably, Y is trifluoromethyl group; n is 1; and X is 6-carbomethoxy-β-D-glucopyranosyl group.

Further, the Compounds (1) and (2) preferably include the following compounds and pharmaceutically acceptable salts thereof.

1'-Cyclobutyl-4'-[(4-ethylphenyl)methyl]-5'-trifluoromethyl-1H-pyrazole-3'-o-β-D-glucopyranoside
1'-Cyclopentyl-4'-[(4-ethylphenyl)methyl]-5'-trifluoromethyl-1H-pyrazole-3'-o-β-D-glucopyranoside
1'-Cyclohexyl-4'-[(4-ethylphenyl)methyl]-5'-trifluoromethyl-1H-pyrazole-3'-o-β-D-glucopyranoside
1'-(3-Cyclopenten-1-yl)-4'-[(4-ethylphenyl)methyl]-5'-methyl-1H-pyrazole-3'-o-β-D-glucopyranoside
1'-Cyclobutyl-4'-[(4-ethylphenyl)methyl]-5'-methyl-1H-pyrazole-3'-o-β-D-glucopyranoside
1'-Cyclopentyl-4'-[(4-ethylphenyl)methyl]-5'-methyl-1H-pyrazole-3'-o-β-D-glucopyranoside
1'-Cyclohexyl-4'-[(4-ethylphenyl)methyl]-5'-methyl-1H-pyrazole-3'-o-β-D-glucopyranoside
1'-Cyclobutyl-4'-[(4-ethylphenyl)methyl]-5'-trifluoromethyl-1H-pyrazole-3'-o-(6-carbomethoxy)-β-D-glucopyranoside
1'-Cyclopentyl-4'-[(4-ethylphenyl)methyl]-5'-trifluoromethyl-1H-pyrazole-3'-o-(6-carbomethoxy)-β-D-glucopyranoside
1'-Cyclohexyl-4'-[(4-ethylphenyl)methyl]-5'-trifluoromethyl-1H-pyrazole-3'-o-(6-carbomethoxy)-β-D-glucopyranoside
1'-(3-Cyclopenten-1-yl)-4'-[(4-ethylphenyl)methyl]-5'-methyl-1H-pyrazole-3'-o-(6-carbomethoxy)-β-D-glucopyranoside
1'-Cyclobutyl-4'-[(4-ethylphenyl)methyl]-5'-methyl-1H-pyrazole-3'-o-(6-carbomethoxy)-β-D-glucopyranoside
1'-Cyclopentyl-4'-[(4-ethylphenyl)methyl]-5'-methyl-1H-pyrazole-3'-o-(6-carbomethoxy)-β-D-glucopyranoside
1'-Cyclohexyl-4'-[(4-ethylphenyl)methyl]-5'-methyl-1H-pyrazole-3'-o-(6-carbomethoxy)-β-D-glucopyranoside.

Among them, the following compounds and pharmaceutically acceptable salts thereof are particularly preferable.

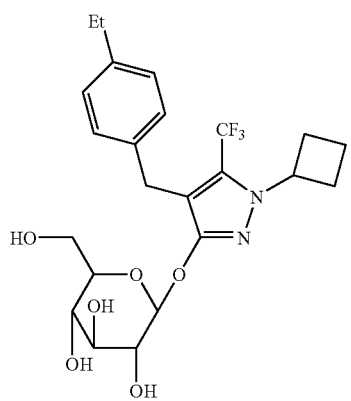

(3)

25
-continued
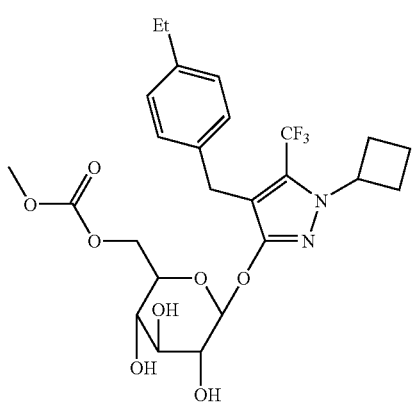
(3a)
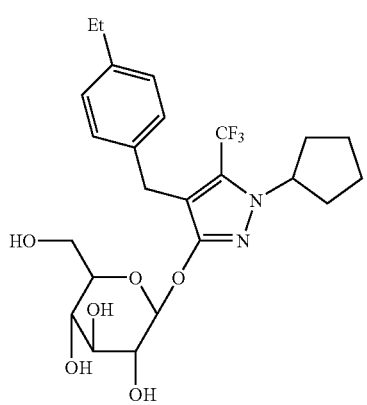
(4)
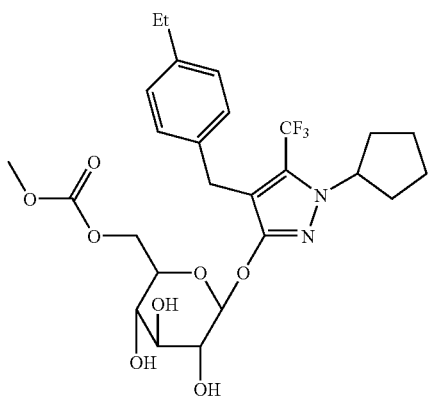
(4a)
As an example of the method for producing the Compounds (1) and (2), the method shown below can be used when X is β-D-glucopyranosyl group.
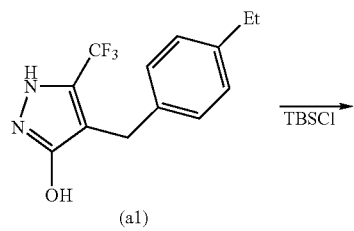
(a1) →TBSCl
26
-continued
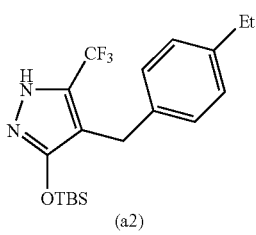
(a2) →DEAD PPH₃ cyclobutanol
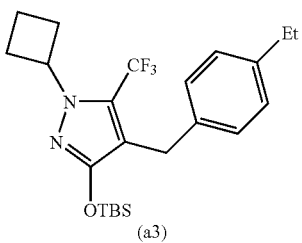
(a3) →HCl aq THF MeOH
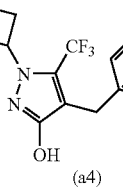
(a4)
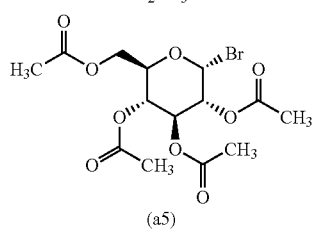
(a5) →K₂CO₃
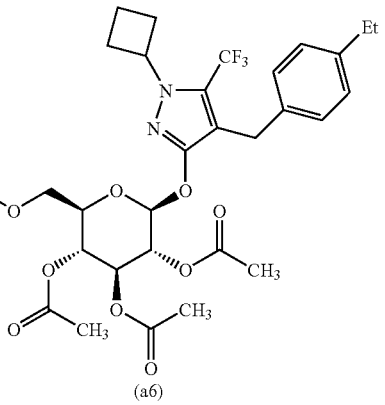
(a6) →NaOH aq EtOH
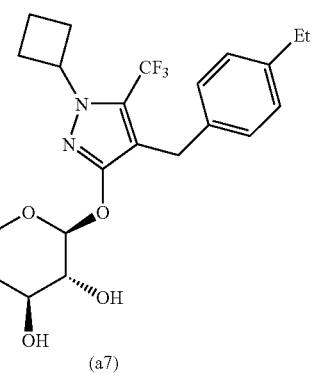
(a7) →ClCOOCH₃ collidine -continued

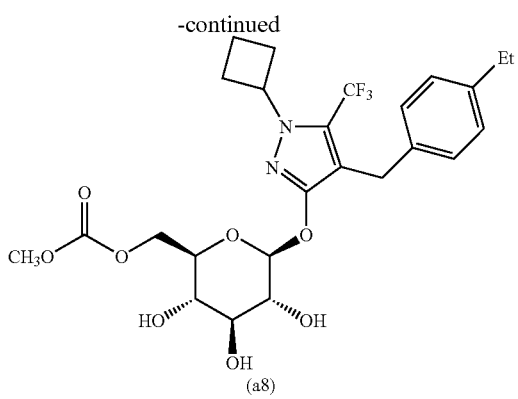

(a8)

The compound (a8) encompassed within the Compound (1) can be produced for example as follows. The hydroxyl group in 1,2-dihydro-4-[(4-ethylphenyl)methyl]-5-(trifluoromethyl)-3H-pyrazol-3-one (a1) is protected with tert-butyldimethylsilyl chloride to prepare (a2). Then, the nitrogen on the pyrazole is allowed to react with cyclobutyl alcohol by Mitsunobu reaction, to prepare (a3). Then, the TBS group in (a3) is deprotected with dilute hydrochloric acid to prepare (a4), followed by overnight reaction with 2,3,4,6-tetra-o-acetyl-α-D-glucopyranosyl bromide (a5) in the presence of potassium carbonate in chloroform and water and subsequent purification using chromatography and the like, to obtain tetra-o-acetyl intermediate (a6). Then, deprotection is done in aqueous sodium hydroxide solution, to obtain (a7). Reaction of the primary hydroxyl group in the resulting (a7) with methyl chlorocarbonate produces (a8).

The Compounds (1) and (2) produced by the method can be separated and purified readily from the reaction mixtures by general isolation and purification measures, for example solvent extraction, chromatography and crystallization.

The hydroxyl groups in the Compounds (1) and (2) may be substituted with appropriate substituents provided that the substituted hydroxyl groups can be modified into unsubstituted hydroxyl group in human body. For example, the substituents for the hydroxyl groups include acyl group and carbamate group. The acyl group includes for example alkanoyl groups with 2 to 20 carbon atoms and benzoyl group. The carbamate group includes for example lower alkoxy-carbonyl groups.

In case that the Compounds (1) and (2) are possibly prepared into salt forms, the salts may satisfactorily be pharmaceutically acceptable. For any acid group in case that such acid group exists in the formulas, the salts include for example ammonium salts; salts with alkali metals such as sodium and potassium; salts with alkali earth metals such as calcium and magnesium; aluminum salts; zinc salts; salts with organic amines such as triethylamine, ethanolamine, morpholine, piperidine and dicyclohexylamine; and salts with basic amino acids such as arginine and lysine. For any basic group in case that such basic group exists in the formulas, the salts thereof include for example salts with inorganic acids such as hydrochloric acid, sulfuric acid and phosphoric acid; salts with organic carboxylic acids such as oxalic acid, acetic acid, citric acid, malic acid, benzoic acid, maleic acid, fumaric acid, tartaric acid, succinic acid and glutamic acid; and salts with organic sulfonic acids such as methanesulfonic acid and p-toluenesulfonic acid. As to the method for preparing such salts, the Compounds (1) and (2) are mixed with necessary acids or bases at appropriate ratios in solvents and dispersants, or other salt forms of the Compounds (1) and (2) may be modified into such salts by cation exchange or anion exchange.

The Compounds (1) and (2) include solvates thereof, for example hydrates thereof and alcohol adducts thereof.

(ii) Compounds (1A) and (2A) and pharmaceutically acceptable salts thereof

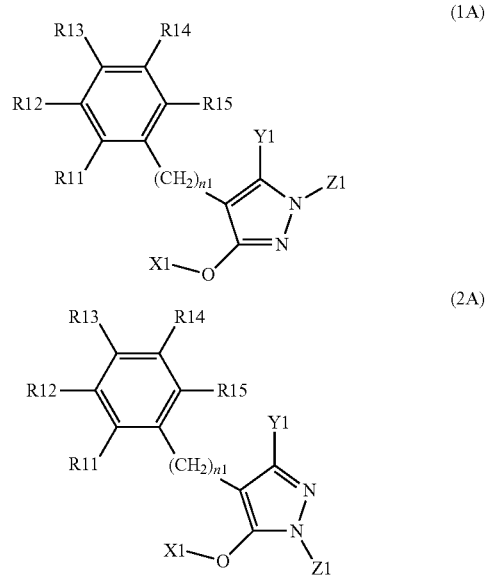

[in the formulas, X1 represents β-D-glucopyranosyl group (where one or plural hydroxyl groups may be acylated) or β-D-glucuronyl group (where one or plural hydroxyl groups may be acylated and carboxyl group may be esterified);

Y1 represents a lower alkyl group or a perfluoro-lower alkyl group;

Z1 represents hydrogen atom, a lower alkyl group, a perfluoro-lower alkyl group, an optionally substituted aralkyl group or optionally substituted phenyl group;

R11 through R15 may be the same or different and represent hydrogen atom, a lower alkyl group, a perfluoro-lower alkyl group, a lower alkoxy group, a perfluoro-lower alkoxy group, a lower alkylthio group, a perfluoro-lower alkylthio group, a lower alkylamino group, a halogeno group, a lower alkanoyl group, a lower alkenyl group or a lower alkynyl group; and n represents an integer of 0 to 3.]

The term "lower" in the Compounds (1A) and (2A) means one to 6 carbon atoms, preferably one to 4 carbon atoms. "Alkyl", "alkenyl" and "alkynyl" in the alkyl group, the perfluoro-lower alkyl group, the lower alkoxy group, the perfluoro-lower alkoxy group, the lower alkylthio group, the perfluoro-lower alkylthio group, the lower alkylamino group, the lower alkanoyl group, the lower alkenyl group and the lower alkynyl group may be linear or branched.

The alkyl moiety in the "aralkyl group" in the Compounds (1A) and (2A) is a lower alkyl group. The aryl moiety in the "aralkyl group" is a monocyclic or bicyclic carbon atom-constituted aromatic substituent with 5 to 12 carbon atoms.

The lower alkyl group in the Compounds (1A) and (2A) includes for example methyl group, ethyl group, propyl group, butyl group, pentyl group, isopropyl group, isobutyl group and isopentyl group.

The perfluoro-lower alkyl group in the Compounds (1A) and (2A) includes for example trifluoromethyl group.

The optionally substituted aralkyl group in the Compounds (1A) and (2A) includes aralkyl groups with 7 to 10 carbon atoms, for example benzyl group, benzyl group optionally substituted with one or two or more substituents on the benzene ring, phenethyl group and phenethyl group optionally substituted with one or two or more substituents on the benzene ring. Herein, the substituents for benzyl group and phenethyl group include for example lower alkoxy groups, lower alkyl groups, halogeno groups and halogeno-lower alkyl groups. Additionally, the number of the substituents is preferably one to 3.

The substituents for the optionally substituted phenyl group in the Compounds (1A) and (2A) include for example lower alkoxy groups, lower alkyl groups, halogeno groups and halogeno-lower alkyl groups. Additionally, the number of the substituents is preferably one to 3.

The lower alkoxy groups in the Compounds (1A) and (2A) include for example methoxy group, ethoxy group, propyloxy group and isopropyloxy group.

The perfluoro-lower alkoxy groups in the Compounds (1A) and (2A) include for example trifluoromethoxy group.

The lower alkylthio groups in the Compounds (1A) and (2A) include for example methylthio group, ethylthio group and propylthio group.

The perfluoro-lower alkylthio groups in the Compounds (1A) and (2A) include for example trifluoromethylthio group.

The lower alkylamino groups in the Compounds (1A) and (2A) include for example methylamino group, ethylamino group, propylamino group, dimethylamino group and diethylamino group.

The halogeno groups in the Compounds (1A) and (2A) include fluorine atom, bromine atom, chlorine atom and bromine atom.

The lower alkanoyl groups in the Compounds (1A) and (2A) include for example acetyl group and propionyl group.

The lower alkenyl groups in the Compounds (1A) and (2A) include for example vinyl group, propenyl group and 2-methyl-1-propenyl group.

The lower alkynyl groups in the Compounds (1A) and (2A) include for example ethynyl group and propynyl group.

The group for acylating the hydroxyl groups in the Compounds (1A) and (2A) includes for example acyl group and carbamate group. The acyl group includes for example acetyl group, propionyl group, benzoyl group and pivaloyl group. The carbamate group includes for example methyl carbonate group, ethyl carbonate group, propyl carbonate group, isopropyl carbonate group and phenyl carbonate group. The group for esterifying carboxyl group includes lower alkyl groups, for example methyl group, ethyl group, propyl group and isopropyl group.

One or plural hydroxyl groups in β-D-glucopyranosyl group as the group represented by X1 in the Compounds (1A) and (2A) may be acylated. Particularly, one or plural hydroxyl groups in the group may be acylated with a group or groups selected from alkanoyl groups with 2 to 20 carbon atoms, lower alkoxy-carbonyl groups and benzoyl group. Such β-D-glucopyranosyl group includes for example 6-o-acetyl-β-D-glucopyranosyl group and 6-o-methoxycarbonyl-β-D-glucopyranosyl group. Further, the number of hydroxyl groups to be acylated is preferably one to 3.

In β-D-glucuronyl group as the group represented by X1 in the Compounds (1A) and (2A), one or plural hydroxyl groups may be acylated and carboxyl group may be esterified. In the group, particularly, one or plural hydroxyl groups may be acylated with a group or groups selected from alkanoyl groups with 2 to 20 carbon atoms, lower alkoxy-carbonyl groups and benzoyl group and carboxylic acid may be esterified with a lower alkyl group. For example, the group includes 6-o-methyl-β-D-glucuronyl group. Additionally, the number of hydroxyl groups to be acylated is preferably one to 3.

In the Compounds (1A) and (2A), the group represented by X1 is particularly preferably β-D-glucopyranosyl group, 6-o-acetyl-β-D-glucopyranosyl group, 6-o-methoxycarbonyl-β-D-glucopyranosyl group, β-D-glucuronyl group and 6-o-methyl-β-D-glucuronyl group. Further, β-D-glucopyranosyl group and β-D-glucuronyl group are more preferable. Particularly preferably, the group represented by X is β-D-glucopyranosyl group where one or plural hydroxyl groups are acylated with a group or groups selected from alkanoyl groups with 2 to 20 carbon atoms, lower alkoxy-carbonyl groups and benzoyl group. More preferably, one or more plural hydroxyl groups therein are acylated with C2 to C6 alkanoyl groups or lower alkoxy-carbonyl groups. Among them, preferably, one hydroxyl group is acylated. Particularly, the hydroxyl group bonded to the carbon atom at 6-position is preferably acylated. Specifically, the group represented by X is preferably 6-o-acetyl-β-D-glucopyranosyl group and 6-o-methoxycarbonyl-β-D-glucopyranosyl group.

The group represented by Y1 in the Compounds (1A) and (2A) is preferably a lower alkyl group with one to 3 carbon atoms or a perfluoro-lower alkyl group with one to 6 carbon atoms, particularly preferably methyl group and trifluoromethyl group.

The group represented by Z1 in the Compounds (1A) and (2A) is preferably hydrogen atom or a lower alkyl group with one to 6 carbon atoms. Additionally preferably, the group is hydrogen atom, a lower alkyl group with one to 3 carbon atoms, an unsubstituted aralkyl group or an aralkyl group with the aryl moiety substituted at the 4-position and unsubstituted phenyl group. Additionally preferably, the group is hydrogen atom, methyl group, ethyl group, propyl group, isopropyl group, unsubstituted benzyl group or benzyl group with the aryl moiety substituted at the 4-position and unsubstituted phenyl group. Among them, hydrogen atom, methyl group, ethyl group, propyl group and isopropyl group are preferable. Particularly, isopropyl group is preferable.

The groups represented by R11 through R15 in the Compounds (1A) and (2A) are preferably lower alkyl groups, perfluoro-lower alkyl groups, lower alkoxy groups, perfluoro-lower alkoxy groups, lower alkylthio groups, perfluoro-lower alkylthio groups, lower alkylamino groups, halogeno groups, lower alkanoyl groups, lower alkenyl groups and lower alkynyl groups, more preferably lower alkyl groups with one to 6 carbon atoms, lower alkylthio groups with one to 6 carbon atoms, halogeno groups, lower alkoxy groups, lower alkenyl groups and lower alkynyl groups, particularly preferably methyl group, ethyl group, methylthio group, ethylthio group, fluorine atom, methoxy group, vinyl group, propenyl group, ethynyl group and propynyl group. Furthermore, at least one of the groups represented by R11 through R15 is any one of the preferable groups described above. Particularly, one or two of the groups represented by R11 through R15 are any of the preferable groups described above, while the remaining groups are hydrogen atom. In this case, more preferably, at least R13 is any one of the preferable groups. In case that two of R11 through R15 are any of the preferable groups, these groups may be the same or different. More preferably, these groups may be different. Among them, preferably, R14 or R15 is fluorine atom when R13 is a lower alkyl group, a lower alkoxy group, a lower alkenyl group or a lower alkynyl group. Preferably, at least one of R11, R12, R14 and R15 is a halogeno group. Particularly preferably, any one of R11, R12, R14 and R15 is a halogeno group or all of R11, R12, R14 and R15 are hydrogen atom, while R13 is a lower alkyl group, a lower alkoxy group, a lower alkenyl group or a lower alkynyl group. Additionally preferably, any one of R11, R12, R14 and R15 is fluorine atom, while R13 is methyl group, ethyl group, methoxy group, vinyl group or ethynyl group.

In the Compounds (1A) and (2A), n1 is particularly preferably an integer 1.

In the Compounds (1A) and (2A), at least one of R11 through R15 is a lower alkyl group, a perfluoro-lower alkyl group, a lower alkoxy group, a perfluoro-lower alkoxy group, a lower alkylthio group, a perfluoro-lower alkylthio group, a lower alkylamino group, a halogeno group, a lower alkanoyl group, a lower alkenyl group or a lower alkynyl group.

In the Compounds (1A) and (2A), additionally, at least one of R11, R12, R14 and R15 is a halogeno group.

In the Compounds (1A) and (2A), further, Y1 is preferably trifluoromethyl group.

In the Compounds (1A) and (2A), preferably, Y1 is trifluoromethyl group and n1 is 1.

In the Compounds (1A) and (2A), additionally preferably, Y1 is trifluoromethyl group; n1 is 1; and X1 is β-D-glucopyranosyl group (where one or plural hydroxyl groups may be acylated with a group or groups selected from alkanoyl groups with 2 to 20 carbon atoms, lower alkoxy-carbonyl groups and benzoyl group.)

In the Compounds (1A) and (2A), additionally preferably, Y1 is trifluoromethyl group; n1 is 1; and X1 is β-D-glucuronyl group (where one or plural hydroxyl groups may be acylated with a group or groups selected from alkanoyl groups with 2 to 20 carbon atoms, lower alkoxy-carbonyl groups and benzoyl group and carbonyl group may be esterified with a lower alkyl group).

In the Compounds (1A) and (2A), additionally preferably, Y1 is trifluoromethyl group; n1 is 1; and X is β-D-glucopyranosyl group.

In the Compounds (1A) and (2A), additionally preferably, Y1 is trifluoromethyl group; n1 is 1; and X is 6-acetyl-β-D-glucopyranosyl group.

In the Compounds (1A) and (2A), additionally preferably, Y1 is trifluoromethyl group; n is 1; and X is 6-carbomethoxy-β-D-glucopyranosyl group.

In the Compounds (1A) and (2A), additionally preferably, Y1 is trifluoromethyl group; n1 is 1; and X is β-D-glucuronyl group.

In the Compounds (1A) and (2A), additionally preferably, Y1 is trifluoromethyl group; n1 is 1; and X is 6-methyl-β-D-glucuronyl group.

In the Compounds (1A) and (2A), additionally preferably, X1 is β-D-glucopyranosyl group (where one or plural hydroxyl groups may be acylated with a group or groups selected from alkanoyl groups with 2 to 20 carbon atoms, lower alkoxy-carbonyl groups and benzoyl group).

In the Compounds (1A) and (2A), additionally preferably, X1 is β-D-glucopyranosyl group (where one or plural hydroxyl groups may be acylated with a lower alkoxy-carbonyl group).

In the Compounds (1A) and (2A), additionally preferably, Y1 is a lower alkyl group with one to 3 carbon atoms or a perfluoro-lower alkyl with one to 6 carbon atoms; n1 is 1; and X1 is β-D-glucopyranosyl group (where one or plural hydroxyl groups may be acylated with a group or groups selected from alkanoyl groups with 2 to 20 carbon atoms, lower alkoxy-carbonyl groups and benzoyl group); Z1 represents hydrogen atom, a lower alkyl group with one to 3 carbon atoms, an unsubstituted aralkyl group or a substituted aralkyl group with a substituent on the aryl moiety at 4-position or unsubstituted phenyl group; any one of R11, R12, R14 and R15 is a halogeno group or all of R11, R12, R14 and R15 are hydrogen atom, while R13 is a lower alkyl group, a lower alkoxy group, a halogeno group, a lower alkenyl group or a lower alkynyl group.

In the Compounds (1A) and (2A), additionally preferably, Y1 is methyl group; n1 is 1; and X is β-D-glucopyranosyl group (where one or plural hydroxyl groups may be acylated with a group or groups selected from alkanoyl groups with 2 to 20 carbon atoms, lower alkoxy-carbonyl groups and benzoyl group); Z1 is isopropyl group; R13 is a lower alkyl group; R14 or R15 is fluorine atom.

In the Compounds (1A) and (2A), additionally preferably, Y1 is methyl group; n1 is 1; and X1 is β-D-glucopyranosyl group (where one or plural hydroxyl groups may be acylated with a group of groups selected from alkanoyl groups with 2 to 20 carbon atoms, lower alkoxy-carbonyl groups and benzoyl group); Z1 is isopropyl group; R13 is a lower alkoxy group; and R14 or R15 is fluorine atom.

In the Compounds (1A) and (2A), additionally preferably, Y1 is methyl group; n1 is 1; and X1 is β-D-glucopyranosyl group (where one or plural hydroxyl groups may be acylated with a group or groups selected from alkanoyl groups with 2 to 20 carbon atoms, lower alkoxy-carbonyl groups and benzoyl group); Z1 is isopropyl group; and R13 is a lower alkynyl group.

In the Compounds (1A) and (2A), additionally preferably, Y1 is methyl group; n1 is 1; and X1 is β-D-glucopyranosyl group (where one or plural hydroxyl groups may be acylated with a group or groups selected from alkanoyl groups with 2 to 20 carbon atoms, lower alkoxy-carbonyl groups and benzoyl group); Z1 is isopropyl group; R13 is a lower alkynyl group; and R14 or R15 is fluorine atom.

In the Compounds (1A) and (2A), additionally preferably, Y1 is methyl group; n1 is 1; and X1 is β-D-glucopyranosyl group (where one or plural hydroxyl groups may be acylated with a group or groups selected from alkanoyl groups with 2 to 20 carbon atoms, lower alkoxy-carbonyl groups and benzoyl group); Z1 is isopropyl group; and R3 is a lower alkenyl group.

In the Compounds (1A) and (2A), additionally preferably, Y1 is methyl group; n1 is 1; and X1 is β-D-glucopyranosyl group (where one or plural hydroxyl groups may be acylated with a group or groups selected from alkanoyl groups with 2 to 20 carbon atoms, lower alkoxy-carbonyl groups and benzoyl group); Z1 is isopropyl group; R13 is a lower alkenyl group; and R14 or R15 is fluorine atom.

In the Compounds (1A) and (2A), additionally preferably, Y1 is methyl group or trifluoromethyl group; n1 is 1; and X1 is β-D-glucopyranosyl group (where one or plural hydroxyl groups may be acylated with a group or groups selected from alkanoyl groups with 2 to 20 carbon atoms, lower alkoxy-carbonyl groups and benzoyl group); Z1 is hydrogen atom, isopropyl group, an aralkyl group or phenyl group; any one of R11, R12, R14 and R15 is fluorine atom, while R13 is methyl group, ethyl group, methoxy group, vinyl group or ethynyl group.

Particularly, the Compounds (1A) and (2A) preferably include the following compounds and pharmaceutically acceptable salts thereof:

4-((4-Methylthiophenyl)methyl)-5-(trifluoromethyl)-1H-pyrazole-3-o-β-D-glucopyranoside;
4-((4-Ethylthiophenyl)methyl)-5-(trifluoromethyl)-1H-pyrazole-3-o-β-D-glucopyranoside;
4-((4-Propylthiophenyl)methyl)-5-(trifluoromethyl)-1H-pyrazole-3-o-β-D-glucopyranoside;

4-((4-Isopropylthiophenyl)methyl)-5-(trifluoromethyl)-1H-pyrazole-3-o-β-D-glucopyranoside;

4-((4-Methylphenyl)methyl)-5-(trifluoromethyl)-1H-pyrazole-3-o-β-D-glucopyranoside;

4-((4-Ethylphenyl)methyl)-5-(trifluoromethyl)-1H-pyrazole-3-o-β-D-glucopyranoside;

4-((4-Propylphenyl)methyl)-5-(trifluoromethyl)-1H-pyrazole-3-o-β-D-glucopyranoside;

4-((4-Isopropylphenyl)methyl)-5-(trifluoromethyl)-1H-pyrazole-3-o-β-D-glucopyranoside;

4-((4-Vinylphenyl)methyl)-5-(trifluoromethyl)-1H-pyrazole-3-o-β-D-glucopyranoside;

4-((4-Ethynylphenyl)methyl)-5-(trifluoromethyl)-1H-pyrazole-3-o-β-D-glucopyranoside;

4-((4-Methylthiophenyl)ethyl)-5-(trifluoromethyl)-1H-pyrazole-3-o-β-D-glucopyranoside;

4-((4-Ethylthiophenyl)ethyl)-5-(trifluoromethyl)-1H-pyrazole-3-o-β-D-glucopyranoside;

4-((4-Propylthiophenyl)ethyl)-5-(trifluoromethyl)-1H-pyrazole-3-o-β-D-glucopyranoside;

4-((4-Isopropylthiophenyl)ethyl)-5-(trifluoromethyl)-1H-pyrazole-3-o-β-D-glucopyranoside;

4-((3-Methylthiophenyl)ethyl)-5-(trifluoromethyl)-1H-pyrazole-3-o-β-D-glucopyranoside;

4-((3-Ethylthiophenyl)ethyl)-5-(trifluoromethyl)-1H-pyrazole-3-o-β-D-glucopyranoside;

4-((3-Propylthiophenyl)ethyl)-5-(trifluoromethyl)-1H-pyrazole-3-o-β-D-glucopyranoside;

4-((3-Isopropylthiophenyl)ethyl)-5-(trifluoromethyl)-1H-pyrazole-3-o-β-D-glucopyranoside;

4'-((4'-Methylthiophenyl)methyl)-5'-trifluoromethyl-3'-o-(6-o-carbomethoxy-β-D-glucopyranosyl)-1H-pyrazole;

4'-((4'-Ethylphenyl)methyl)-5'-(trifluoromethyl)-3'-o-(6-o-carbomethoxy-β-D-glucopyranosyl)-1H-pyrazole;

4'-((4'-Methylthiophenyl)methyl)-5'-trifluoromethyl-3'-o-(2,3,4,6-o-tetraacetyl-β-D-glucopyranosyl)-1H-pyrazole;

4'-((4'-Ethylphenyl)methyl)-5'-(trifluoromethyl)-3'-o-(2,3,4,6-o-tetraacetyl-β-D-glucopyranosyl)-1H-pyrazole;

4-[(4-Trifluoromethoxyphenyl)methyl]-5-trifluoromethyl-1H-pyrazole-3-o-β-D-glucopyranoside;

4'-[(4'-Trifluoromethoxyphenyl)methyl]-5'-trifluoromethyl-1H-pyrazole-3'-o-(2,3,4,6-o-tetraacetyl)-β-D-glucopyranoside;

4'-[(4'-Trifluoromethoxyphenyl)methyl]-5'-trifluoromethyl-1H-pyrazole-3'-o-(6-carbomethoxy)-β-D-glucopyranoside;

4-[(4-Ethylphenyl)methyl]-1-benzyl-5-trifluoromethyl-1H-pyrazole-3-o-β-D-glucopyranoside;

4'-[(4-Ethylphenyl)methyl]-1'-benzyl-5'-trifluoromethyl-1H-pyrazole-3'-o-(2,3,4,6-tetraacetyl)-β-D-glucopyranoside;

4'-[(4-Ethylphenyl)methyl]-1'-benzyl-5'-trifluoromethyl-1H-pyrazole-3'-o-(6-carbomethoxy)-β-D-glucopyranoside;

4-[(4-Ethylphenyl)methyl]-1-[(4-methoxyphenyl)methyl]-5-trifluoromethyl-1H-pyrazole-3'-o-β-D-glucopyranoside;

4'-[(4-Ethylphenyl)methyl]-1'-[(4-methoxyphenyl)methyl]-5'-trifluoromethyl-1H-pyrazole-3'-o-(2,3,4,6-tetraacetyl)-β-D-glucopyranoside;

4'-[(4-Ethylphenyl)methyl]-1'-[(4-methoxyphenyl)methyl]-5'-trifluoromethyl-1H-pyrazole-3'-o-(6-carbomethoxy)-β-D-glucopyranoside;

4-[(4-Ethylphenyl)methyl]-1-phenyl-5-trifluoromethyl-1H-pyrazole-3-o-β-D-glucopyranoside;

4'-[(4-Ethylphenyl)methyl]-1'-phenyl-5'-trifluoromethyl-1H-pyrazole-3'-o-(2,3,4,6-tetraacetyl)-β-D-glucopyranoside;

4'-[ (4-Ethylphenyl)methyl]-1'-phenyl-5'-trifluoromethyl-1H-pyrazole-3'-o-(6-carbomethoxy)-β-D-glucopyranoside;

4'-((3-Fluoro-4-methoxyphenyl)methyl)-1'-isopropyl-5'-methyl-1H-pyrazole-3'-o-(6-carbomethoxy)-β-D-glucopyranoside;

4'-((3-Fluoro-4-methylphenyl)methyl)-1'-isopropyl-5'-methyl-1H-pyrazole-3'-o-(6-carbomethoxy)-β-D-glucopyranoside;

4'-((2-Fluoro-4-methoxyphenyl)methyl)-1'-isopropyl-5'-methyl-1H-pyrazole-3'-o-(6-carbomethoxy)-β-D-glucopyranoside;

4'-((2-Fluoro-4-methylphenyl)methyl)-1'-isopropyl-5'-methyl-1H-pyrazole-3'-o-(6-carbomethoxy)-β-D-glucopyranoside;

4'-((2-Fluoro-4-ethylphenyl)methyl)-1'-isopropyl-5'-methyl-1H-pyrazole-3'-o-(6-carbomethoxy)-β-D-glucopyranoside;

4'-((3-Fluoro-4-ethylphenyl)methyl)-1'-isopropyl-5'-methyl-1H-pyrazole-3'-o-(6-carbomethoxy)-β-D-glucopyranoside;

4'-((4-Ethynylphenyl)methyl)-1'-isopropyl-5'-methyl-1H-pyrazole-3'-o-(6-carbomethoxy)-β-D-glucopyranoside;

4'-((2-Fluoro-4-ethynylphenyl)methyl)-1'-isopropyl-5'-methyl-1H-pyrazole-3'-o-(6-carbomethoxy)-β-D-glucopyranoside;

4'-((3-Fluoro-4-ethynylphenyl)methyl)-1'-isopropyl-5'-methyl-1H-pyrazole-3'-o-(6-carbomethoxy)-β-D-glucopyranoside;

4'-((4-(1-Propynyl)phenyl)methyl)-1'-isopropyl-5'-methyl-1H-pyrazole-3'-o-(6-carbomethoxy)-β-D-glucopyranoside;

4'-((3-Fluoro-4-(1-propynyl)phenyl)methyl)-1'-isopropyl-5'-methyl-1H-pyrazole-3'-o-(6-carbomethoxy)-β-D-glucopyranoside;

4'-((2-Fluoro-4-(1-propynyl) phenyl)methyl)-1'-isopropyl-5'-methyl-1H-pyrazole-3'-o-(6-carbomethoxy)-β-D-glucopyranoside;

4-((3-Fluoro-4-methoxyphenyl)methyl)-1-isopropyl-5-methyl-1H-pyrazole-3-o-β-D-glucopyranoside;

4-((3-Fluoro-4-methylphenyl)methyl)-1-isopropyl-5-methyl-1H-pyrazole-3-o-β-D-glucopyranoside;

4-((2-Fluoro-4-methoxyphenyl)methyl)-1-isopropyl-5-methyl-1H-pyrazole-3-o-β-D-glucopyranoside;

4-((2-Fluoro-4-methylphenyl)methyl)-1-isopropyl-5-methyl-1H-pyrazole-3-o-β-D-glucopyranoside;

4-((2-Fluoro-4-ethylphenyl)methyl)-1-isopropyl-5-methyl-1H-pyrazole-3-o-β-D-glucopyranoside;

4-((3-Fluoro-4-ethylphenyl)methyl)-1-isopropyl-5-methyl-1H-pyrazole-3-o-β-D-glucopyranoside;

4-((4-Ethynylphenyl)methyl)-1-isopropyl-5-methyl-1H-pyrazole-3-o-β-D-glucopyranoside;

4-((2-Fluoro-4-ethynylphenyl)methyl)-1-isopropyl-5-methyl-1H-pyrazole-3-o-β-D-glucopyranoside;

4-((3-Fluoro-4-ethynylphenyl)methyl)-1-isopropyl-5-methyl-1H-pyrazole-3-o-β-D-glucopyranoside;

4-((4-(1-propynyl)phenyl)methyl)-1-isopropyl-5-methyl-1H-pyrazole-3-o-β-D-glucopyranoside;

4-((3-Fluoro-4-(1-propynyl)phenyl)methyl)-1-isopropyl-5-methyl-1H-pyrazole-3-o-β-D-glucopyranoside;

4-((2-Fluoro-4-(1-propynyl)phenyl)methyl)-1-isopropyl-5-methyl-1H-pyrazole-3-o-β-D-glucopyranoside;

4-((4-Methylthiophenyl)methyl)-5-(trifluoromethyl)-1H-pyrazol-3-yl-β-D-glucopyranoside uronic acid;

4-((4-Ethylthiophenyl)methyl)-5-(trifluoromethyl)-1H-pyrazol-3-yl-β-D-glucopyranoside uronic acid;
4-((4-Propylthiophenyl)methyl)-5-(trifluoromethyl)-1H-pyrazol-3-yl-β-D-glucopyranoside uronic acid;
4-((4-Isopropylthiophenyl)methyl)-5-(trifluoromethyl)-1H-pyrazol-3-yl-β-D-glucopyranoside uronic acid;
4-((4-Methylphenyl)methyl)-5-(trifluoromethyl)-1H-pyrazol-3-yl-β-D-glucopyranoside uronic acid;
4-((4-Ethylphenyl)methyl)-5-(trifluoromethyl)-1H-pyrazol-3-yl-β-D-glucopyranoside uronic acid;
4-((4-Propylphenyl)methyl)-5-(trifluoromethyl)-1H-pyrazol-3-yl-β-D-glucopyranoside uronic acid;
4-((4-Isopropylphenyl)methyl)-5-(trifluoromethyl)-1H-pyrazol-3-yl-β-D-glucopyranoside uronic acid;
4-((4-Vinylphenyl)methyl)-5-(trifluoromethyl)-1H-pyrazol-3-yl-β-D-glucopyranoside uronic acid;
4-((4-Ethynylphenyl)methyl)-5-(trifluoromethyl)-1H-pyrazol-3-yl-β-D-glucopyranoside uronic acid;
4-((4-Methylthiophenyl)ethyl)-5-(trifluoromethyl)-1H-pyrazol-3-yl-β-D-glucopyranoside uronic acid;
4-((4-Ethylthiophenyl)ethyl)-5-(trifluoromethyl)-1H-pyrazol-3-yl-β-D-glucopyranoside uronic acid;
4-((4-Propylthiophenyl)ethyl)-5-(trifluoromethyl)-1H-pyrazol-3-yl-β-D-glucopyranoside uronic acid;
4-((4-Isopropylthiophenyl)ethyl)-5-(trifluoromethyl)-1H-pyrazol-3-yl-β-D-glucopyranoside uronic acid;
4-((3-Methylthiophenyl)ethyl)-5-(trifluoromethyl)-1H-pyrazol-3-yl-β-D-glucopyranoside uronic acid;
4-((3-Ethylthiophenyl)ethyl)-5-(trifluoromethyl)-1H-pyrazol-3-yl-β-D-glucopyranoside uronic acid;
4-((3-Propylthiophenyl)ethyl)-5-(trifluoromethyl)-1H-pyrazol-3-yl-β-D-glucopyranoside uronic acid;
4-((3-Isopropylthiophenyl)ethyl)-5-(trifluoromethyl)-1H-pyrazol-3-yl-β-D-glucopyranoside uronic acid;
Methyl 4-((4-methylthiophenyl)methyl)-5-(trifluoromethyl)-1H-pyrazol-3-yl-β-D-glucopyranouronate; and
Ethyl 4-((4-methylthiophenyl)methyl)-5-(trifluoromethyl)-1H-pyrazol-3-yl-β-D-glucopyranouronate.

Among them, the following compounds and pharmaceutically acceptable salts thereof are particularly preferable:
4-((4-Methylthiophenyl)methyl)-5-(trifluoromethyl)-1H-pyrazole-3-o-β-D-glucopyranoside;
4-((4-Ethylphenyl)methyl)-5-(trifluoromethyl)-1H-pyrazole-3-yl-β-D-glucopyranoside uronic acid;
4-[(4-Ethylphenyl)methyl]-1-benzyl-5-trifluoromethyl-1H-pyrazole-3-o-β-D-glucopyranoside;
4'-[(4'-Ethylphenyl)methyl]-1'-benzyl-5'-trifluoromethyl-1H-pyrazole-3'-o-(6-carbomethoxy)-β-D-glucopyranoside;
4-[(4-Ethylphenyl)methyl]-1-[(4-methoxyphenyl)methyl]-5-trifluoromethyl-1H-pyrazole-3-o-β-D-glucopyranoside;
4'-[(4-Ethylphenyl)methyl]-1'-[(4'-methoxyphenyl)methyl]-5'-trifluoromethyl-1H-pyrazole-3'-o-(6-carbomethoxy)-β-D-glucopyranoside;
4-[(4-Ethylphenyl)methyl]-1-phenyl-5-trifluoromethyl-1H-pyrazole-3-o-β-D-glucopyranoside;
4'-[(4'-Ethylphenyl)methyl]-1'-phenyl-5'-trifluoromethyl-1H-pyrazole-3'-o-(6-carbomethoxy)-β-D-glucopyranoside;
4-[(3-Fluoro-4-methoxyphenyl)methyl]-1-isopropyl-5-methyl-1H-pyrazole-3-o-β-D-glucopyranoside;
4'-[(3'-Fluoro-4'-methoxyphenyl)methyl]-1'-isopropyl-5'-methyl-1H-pyrazole-3'-o-(6-carbomethoxy)-β-D-glucopyranoside;
4-[(2-Fluoro-4-methoxyphenyl)methyl]-1-isopropyl-5-methyl-1H-pyrazole-3-o-β-D-glucopyranoside;
4'-[(2-Fluoro-4-methoxyphenyl) methyl]-1'-isopropyl-5'-methyl-1H-pyrazole-3'-o-(6-carbomethoxy)-β-D-glucopyranoside;
4-[(3-Fluoro-4-methylphenyl)methyl]-1-isopropyl-5-methyl-1H-pyrazole-3-o-β-D-glucopyranoside; and
4'-[(3'-Fluoro-4'-methylphenyl)methyl]-1'-isopropyl-5'-methyl-1H-pyrazole-3'-o-(6-carbomethoxy)-β-D-glucopyranoside.

Specifically, the following compounds and pharmaceutically acceptable salts thereof are particularly preferable.

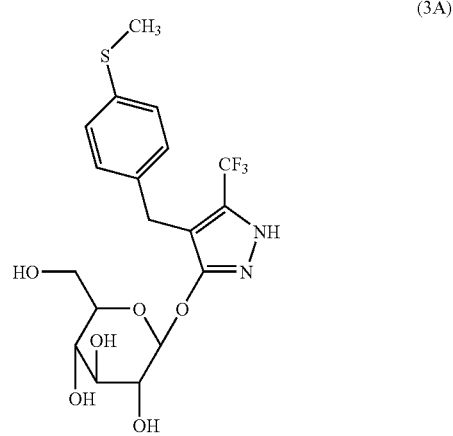

(3A)

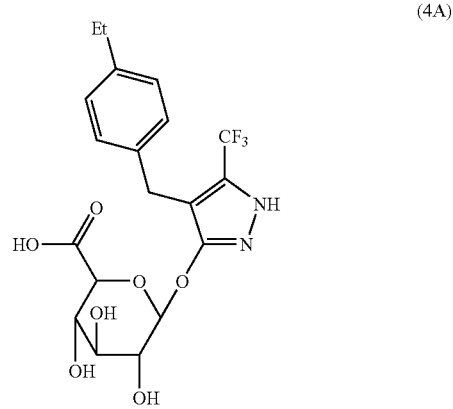

(4A)

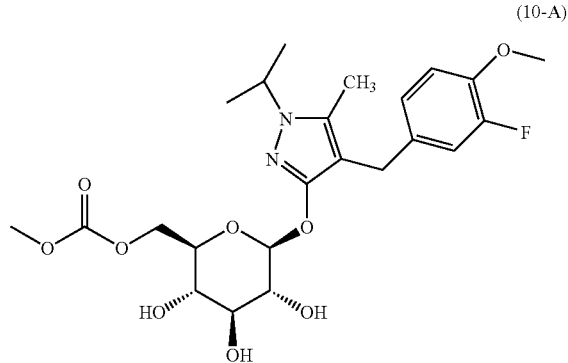

(10-A)

(12-A)

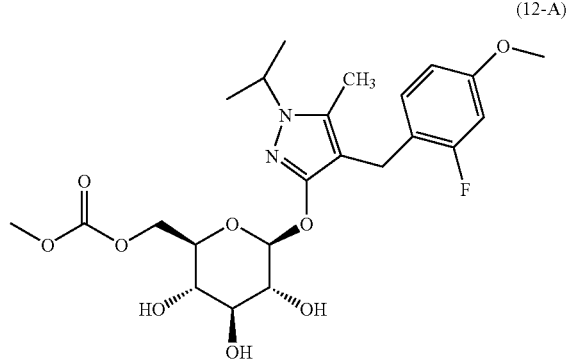

(14-A)

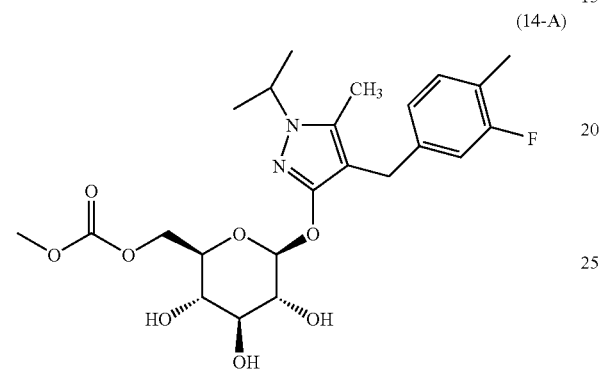

(16-A)

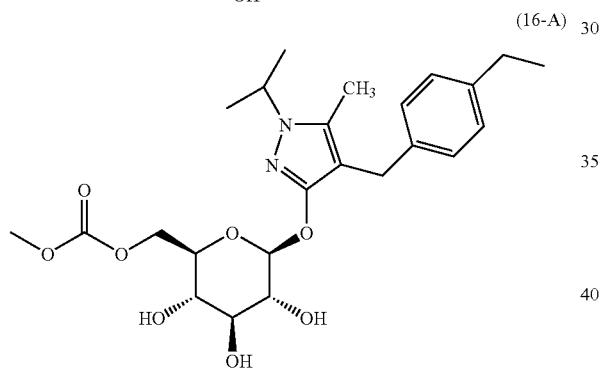

Additionally, the following compounds and pharmaceutically acceptable salts thereof are also particularly preferable:

4'-[(4-Ethylphenyl)methyl]-1'-isopropyl-5'-methyl-1H-pyrazole-3'-o-(6-carbomethoxy)-β-D-glucopyranoside; and 4-[(4-Ethylphenyl)methyl]-1-isopropyl-5'-methyl-1H-pyrazole-3-o-β-D-glucopyranoside.

In case that X is β-D-glucopyranosyl group or β-D-glucuronyl group, the following method can be used as an example of the production method of Compounds (1A) and (2A).

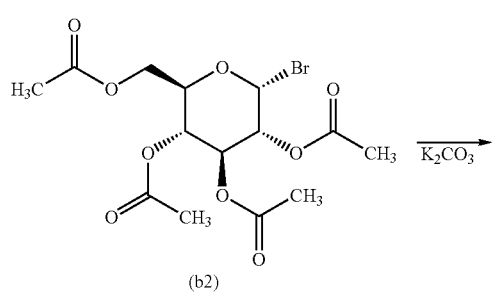

(b2)

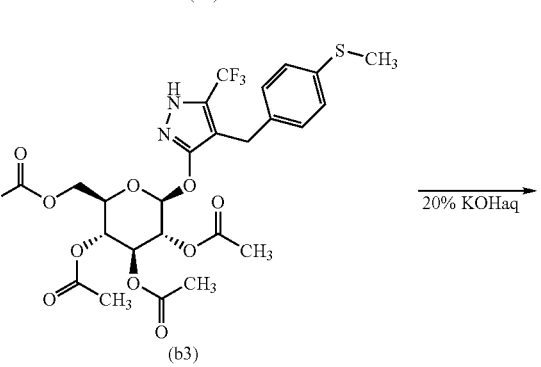

(b3)

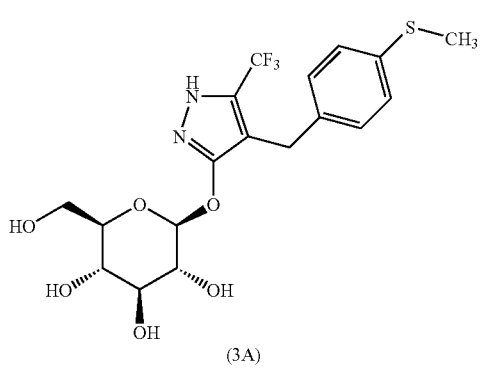

(3A)

The Compound of the formula (3A) can be obtained for example by overnight reaction of 1,2-dihydro-4-[(4-methylthiophenyl)methyl]-5-(trifluoromethyl)-3H-pyrazol-3-one (b1) (prepared by the method described in J. Med. Chem 1996, 39, 3920-3928) with 2,3,4,6-tetra-o-acetyl-α-D-glucopyranosyl bromide (b2) in the presence of potassium carbonate in chloroform and water and purification using chromatography and the like to obtain tetra-o-acetyl intermediate (b3) and subsequent deprotection of the intermediate in an aqueous potassium hydroxide solution.

(b1)            (b4)

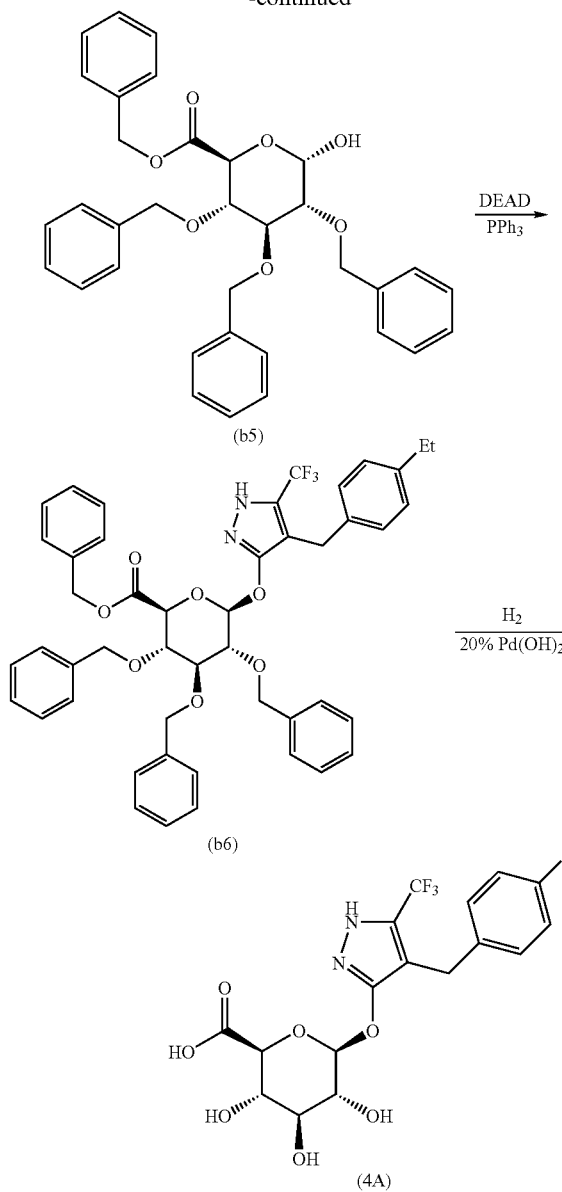

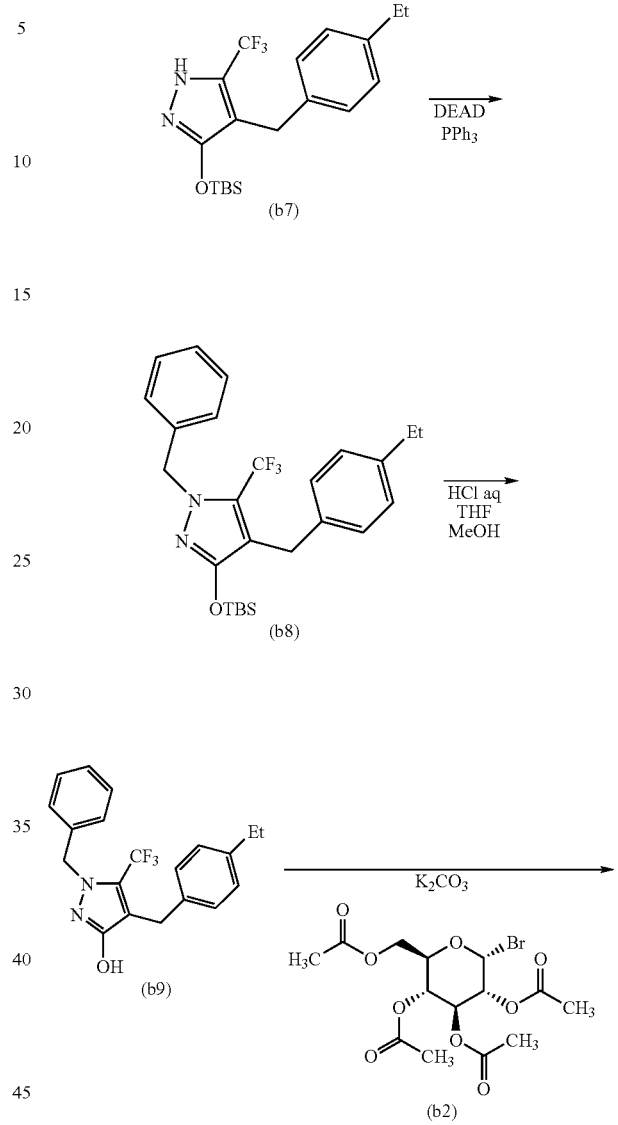

The Compound of the formula (4A) can be obtained for example by reaction of 1,2-dihydro-4-[(4-ethylphenyl)methyl]-5-(trifluoromethyl)-3H-pyrazol-3-one (b4) (prepared by the method described in J. Med. Chem 1996, 39, 3920-3928) and 2,3,4-tri-o-benzyl-D-glucopyranoside uronic acid benzyl ester (b5) with triphenylphosphine and diethyl azodicarboxylate (DEAD) in tetrahydrofuran for 1.5 hours and purification using chromatography and the like to obtain tetrabenzyl intermediate (b6) and subsequent deprotection of the intermediate with 20% Pd(OH)$_2$ in hydrogen atmosphere.

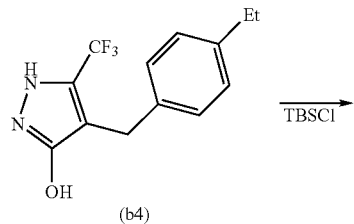

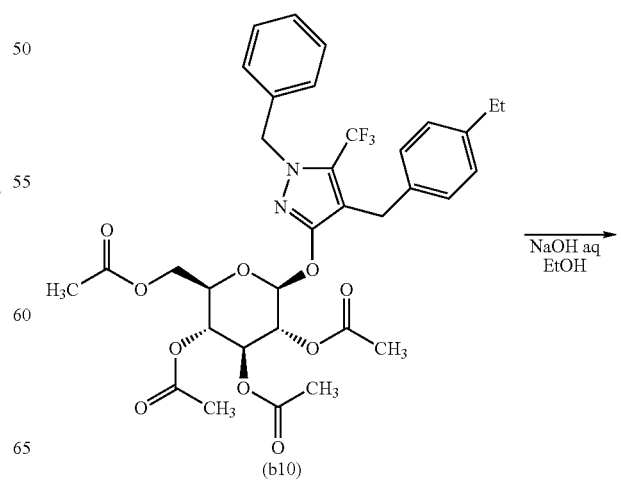

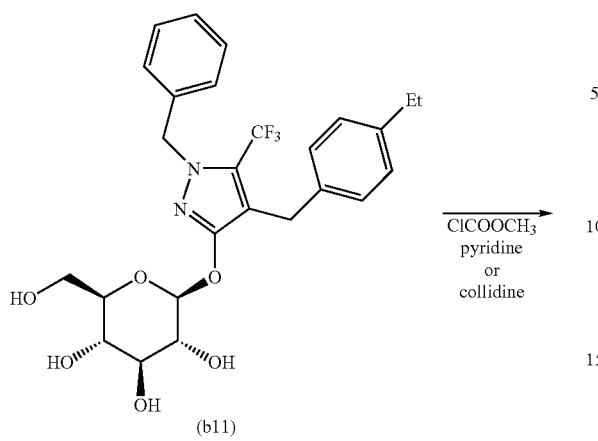

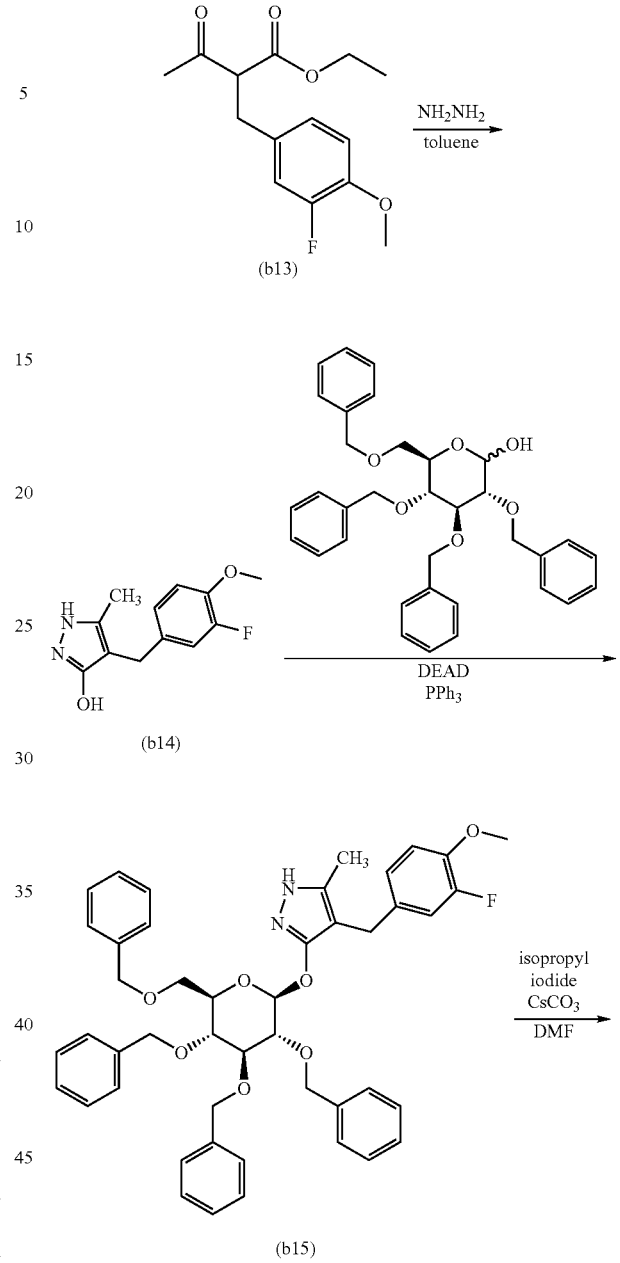

The Compound of the formula (b12) can be obtained as follows. For example, the hydroxyl group of 1,2-dihydro-4-[(4-ethylphenyl)methyl]-5-(trifluoromethyl)-3H-pyrazol-3-one (b4) is protected with tert-butyldimethylsilyl chloride to prepare (b7). Then, the nitrogen on the pyrazole reacts with benzyl alcohol by Mitsunobu reaction to prepare (b8). Then, the TBS group of (b8) is deprotected in dilute hydrochloric acid to prepare (b9), which subsequently reacts with 2,3,4,6-tetra-o-acetyl-α-D-glucopyranosyl bromide (b2) overnight in the presence of potassium carbonate in chloroform and water followed by purification using chromatography and the like, to obtain tetra-o-acetyl intermediate (b10), which is then deprotected in an aqueous potassium hydroxide solution to obtain (b11). Reaction of the primary hydroxyl group of the resulting (b11) with methyl chlorocarbonate can produce (b12).

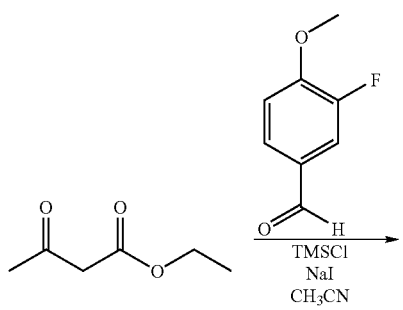

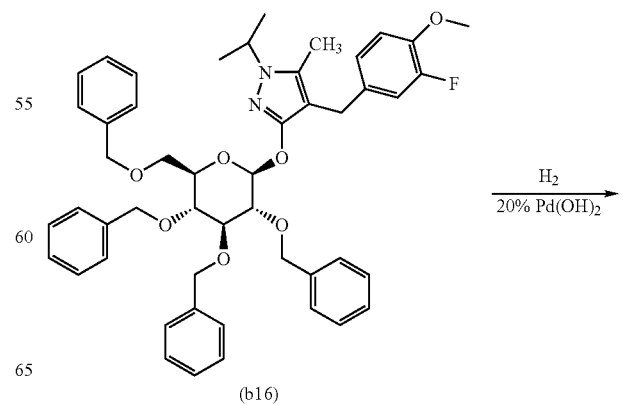

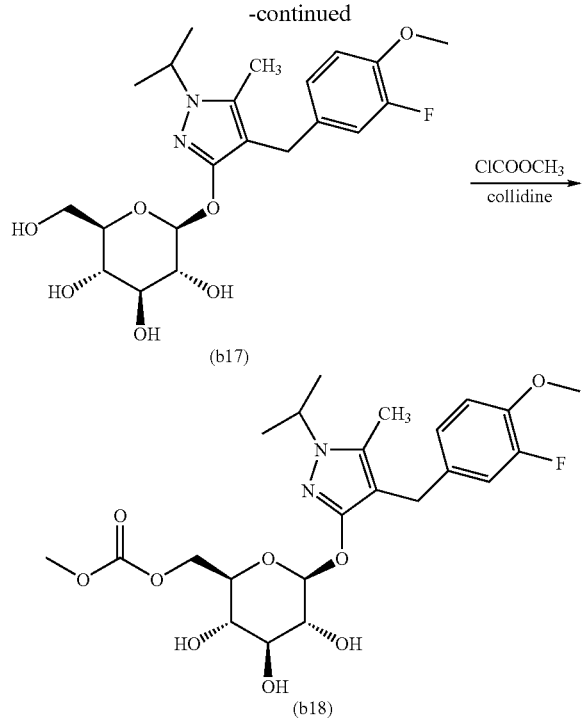

The Compound of the formula (b18) can be obtained as follows. For example, ethyl acetoacetate and 3-fluoro-4-methoxybenzaldehyde react with trimethylsilyl chloride and sodium iodide in acetonitrile, to obtain the intermediate (b13), of which the ring is closed with hydrazine, to obtain 1,2-dihydro-4-[(3-fluoro-4-methoxyphenyl)methyl]-5-methyl-3H-pyrazol-3-one (b14). By Mitsunobu reaction, then, the hydroxyl group on the pyrazole reacts with 2,3,4,6-tetra-benzylglucopyranose to obtain (b15). Continuously, the nitrogen of the pyrazole at 1-position can be isopropylated and prepared into (b16), using cesium carbonate and isopropyl iodide. The benzyl-protecting group of (b16) is deprotected with 20% Pd(OH)$_2$ in hydrogen atmosphere to prepare (b17). Continuously, the hydroxyl group of (b17) at 6-position reacts with methyl chlorocarbonate in collidine to obtain (b18).

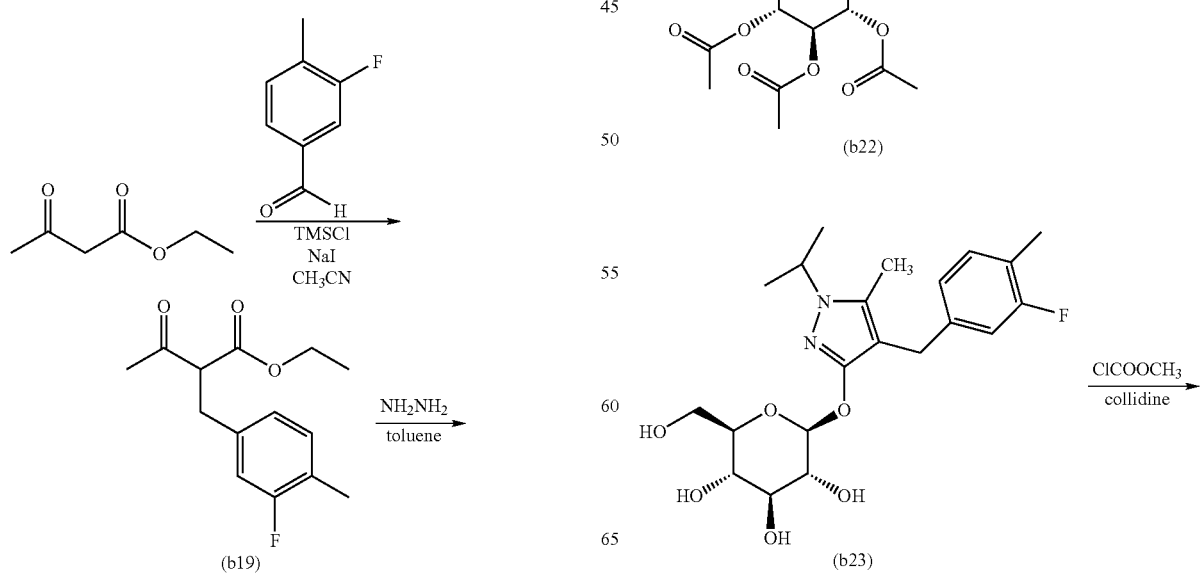

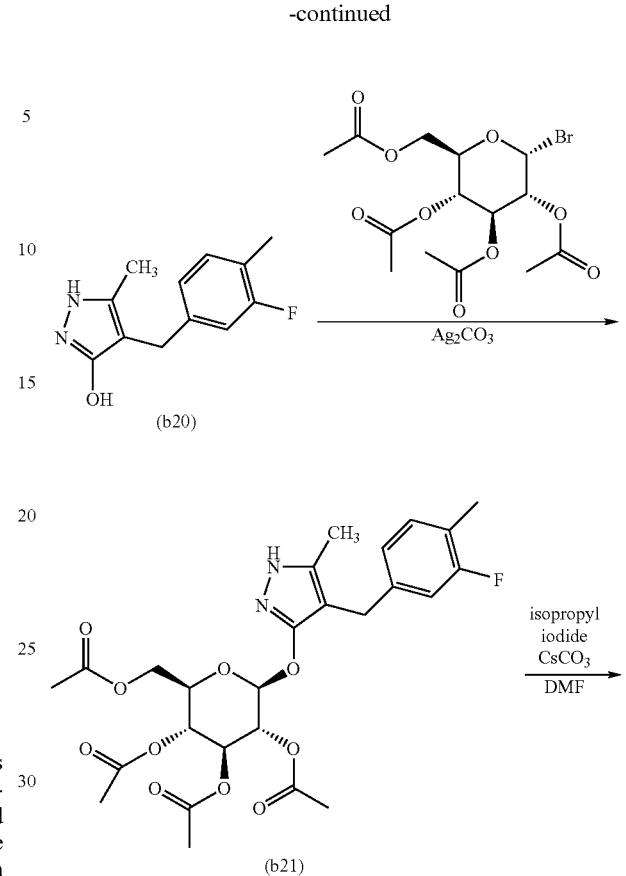

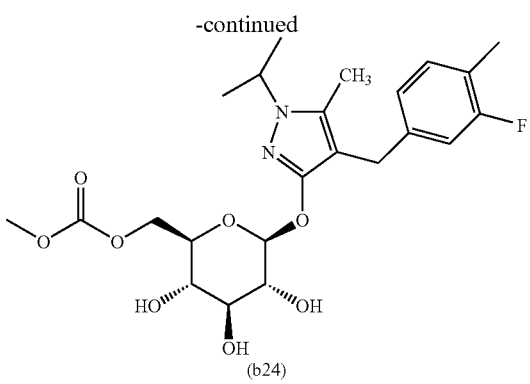

(b24)

The Compound of the formula (b24) can be obtained as follows. For example, ethyl acetoacetate and 3-fluoro-4-methylbenzaldehyde react with trimethylsilyl chloride and sodium iodide in acetonitrile, to obtain the intermediate (b19), which is subjected to ring closing with hydrazine, to obtain 1,2-dihydro-4-[(3-fluoro-4-methylphenyl)methyl]-5-methyl-3H-pyrazol-3-one (b20). Continuously, then, 2,3,4,6-o-tetraacetyl-α-D-glucopyranosyl bromide is allowed to react with the hydroxyl group on the pyrazole, using silver carbonate, to obtain (b21). Continuously, the nitrogen of the pyrazole at 1-position is then isopropylated, using cesium carbonate and isopropyl iodide to obtain (b22). The acetyl-protecting group of (b22) is deprotected with 1N LiOH, to obtain (b23). Continuously, then, the hydroxyl group of (b23) at 6-position reacts with methyl chlorocarbonate in collidine, to obtain (b24).

The Compounds (1A) and (2A) produced by the methods can be separated and purified readily from the reaction mixtures by general isolation and purification measures, for example solvent extraction, chromatography and crystallization.

Further, the hydroxyl groups in the Compounds (1A) and (2A) may be substituted with appropriate substituents provided that the substituted hydroxyl groups can be modified into unsubstituted hydroxyl group in human body. For example, the substituents for the hydroxyl groups include acyl group and carbamate group. The acyl group includes for example alkanoyl groups with 2 to 20 carbon atoms and benzoyl group, while the carbamate group includes for example lower alkoxy-carbonyl groups. Particularly, the substituents for the hydroxyl groups, in glucopyranosyl group preferably include carbamate group, particularly preferably methoxycarbonyl group as a lower alkoxy-carbonyl group. The carboxyl group in the compounds of the invention may be substituted with appropriate substituents provided that the substituted carboxyl group can be modified into unsubstituted carboxyl group in biological organisms. The substituents for the carboxyl group include for example lower alkyl groups, particularly methyl group and ethyl group.

In case that the Compounds (1A) and (2A) are possibly prepared into salt forms, the salts may satisfactorily be pharmaceutically acceptable. For any acid group in case that such acid group exists in the formulas, the salts include ammonium salts; salts with alkali metals such as sodium and potassium; salts with alkali earth metals such as calcium and magnesium; aluminum salts; zinc salts; salts with organic amines such as triethylamine, ethanolamine, morpholine, piperidine and dicyclohexylamine; and salts with basic amino acids such as arginine and lysine. For any basic group in case that such basic group exists in the formulas, the salts thereof include for example salts with inorganic acids such as hydrochloric acid, sulfuric acid and phosphoric acid; salts with organic carboxylic acids such as oxalic acid, acetic acid, citric acid, malic acid, benzoic acid, maleic acid, fumaric acid, tartaric acid, succinic acid and glutamic acid; and salts with organic sulfonic acids such as methanesulfonic acid and p-toluenesulfonic acid. As to the method for preparing such salts, the Compounds (1A) and (2A) are mixed with necessary acids or bases at appropriate ratios in solvents and dispersants, or other salt forms of the Compounds (1A) and (2A) may be modified into such salts by cation exchange or anion exchange.

The Compounds (1A) and (2A) include solvates thereof, for example hydrates thereof and alcohol adducts thereof.

(iii) Compound (5) and pharmaceutically acceptable salts thereof

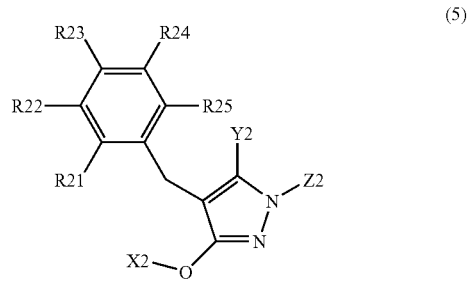

(5)

[in the formula, X2 represents β-D-glucopyranosyl group (where one or plural hydroxyl groups may be acylated);

Y2 represents hydrogen, a lower alkyl group, a fluoro-lower alkyl group or a perfluoro-lower alkyl group;

Z2 represents a halo-lower alkyl group;

R21 through R25 may be the same or different and represent hydrogen atom, a halogeno group, a lower alkyl group, a halo-lower alkyl group, a perfluoro-lower alkyl group, a lower alkoxy group, a perfluoro-lower alkoxy group, a lower alkylthio group, a perfluoro-lower alkylthio group, a lower alkylamino group, a lower alkanoyl group, a lower alkenyl group, a lower alkynyl group or an optionally substituted aralkyl group.]

The term "lower alkyl" in the Compound (5) means alkyl groups with one to 6 carbon atoms (preferably one to 3 carbon atoms).

The term "lower alkenyl" means alkenyl groups with 2 to 6 carbon atoms (preferably 2 to 4 carbon atoms).

The term "lower alkynyl", means alkynyl groups with 2 to 6 carbon atoms (preferably 2 to 4 carbon atoms).

The term "lower alkoxy" means alkoxy groups with one to 6 carbon atoms (preferably 2 to 4 carbon atoms).

The term "lower alkanoyl" means alkanoyl groups with 2 to 6 carbon atoms (preferably 2 to 4 carbon atoms).

In the Compound (5), the "alkyl", "alkenyl" and "alkynyl" in the lower alkyl group, the perfluoro-lower alkyl group, the lower alkoxy group, the perfluoro-lower alkoxy group, the lower alkylthio group, the perfluoro-lower alkylthio group, the lower alkylamino group, the lower alkanoyl group, the lower alkenyl group and the lower alkynyl group may be linear or branched.

The lower alkyl group in the Compound (5) includes for example methyl group, ethyl group, propyl group, butyl group, pentyl group, hexyl group, isopropyl group, isobutyl group, isopentyl group and isohexyl.

The halo-lower alkyl group in the Compound (5) means lower alkyl groups where one or plural hydrogen atoms are substituted with halogeno groups, and includes for example fluoro-lower alkyl groups, chloro-lower alkyl groups and bromo-lower alkyl groups, such as fluoromethyl group, fluoroethyl group, fluoropropyl group, fluorobutyl group, fluoropentyl group, fluorohexyl group, chloromethyl group, chloroethyl group, chloropropyl group, chlorobutyl group, chloropentyl group, chlorohexyl group, bromomethyl group, bromoethyl group, bromopropyl group, bromobutyl group, bromopentyl group and bromohexyl group. Additionally, the number of halogeno groups for substitution is preferably one to 5.

The fluoro-lower alkyl group in the Compound (5) means lower alkyl groups where one or plural hydrogen atoms (but not all of the hydrogen atoms) are substituted with fluorine atoms, and includes for example monofluoromethyl group, difluoromethyl group, 2-fluoroethyl group, 2,2-difluoroethyl group, 2,2,2-trifluoroethyl group, 3,3,3-trifluoropropyl group, 1,3-difluoroisopropyl group, 1,1,1-trifluoro-2-propyl group and 1,1,1,3,3,3-hexafluoroisopropyl group. Additionally, the number of fluorine atoms for substitution is preferably one to 5.

The perfluoro-lower alkyl group in the Compound (5) means lower alkyl groups where all of the hydrogen atoms are substituted with fluorine atoms, and includes for example trifluoromethyl group, pentafluoroethyl group and heptafluoropropyl group.

The lower alkoxy group in the Compound (5) includes for example methoxy group, ethoxy group, propyloxy group, isopropyloxy group and butyloxy group.

The perfluoro-lower alkoxy group in the Compound (5) means lower alkoxy groups where all of the hydrogen atoms are substituted with fluorine atom, and includes for example trifluoromethoxy group, pentafluoroethoxy group and heptafluoropropyloxy group.

The lower alkylthio group in the Compound (5) includes for example methylthio group, ethylthio group and propylthio group.

The perfluoro-lower alkylthio group in the Compound (5) means lower alkylthio groups where all of the hydrogen atoms are substituted with fluorine atom, and includes for example trifluoromethylthio group, pentafluoroethylthio group and heptafluoropropylthio group.

The lower alkylamino group in the Compound (5) includes for example methylamino group, ethylamino group, propylamino group, dimethylamino group, diethylamino group and diisopropylamino group.

The lower alkanoyl group in the Compound (5) includes for example acetyl group and propionyl group.

The lower alkenyl group in the Compound (5) includes for example vinyl group, propenyl group and 2-methyl-1-propenyl group.

The lower alkynyl group in the Compound (5) includes for example ethynyl group and 2-methylethynyl group.

The optionally substituted aralkyl group in the Compound (5) includes for example benzyl group with optionally substituted benzene ring and phenethyl group with optionally substituted benzene ring. Herein, the substituents include lower alkyl groups, lower alkoxy groups, halogeno groups, amino group and lower alkylamino groups, and the number thereof is preferably one to 3.

The halogeno group in the Compound (5) includes for example fluorine atom, chlorine atom, bromine atom and iodine atom.

The group for acylating the hydroxyl groups in the Compound (5) includes for example acyl group and carbamate group. The acyl group includes for example acetyl group, propionyl group, benzoyl group and pivaloyl group. The carbamate group includes for example methyl carbonate group, ethyl carbonate group, propyl carbonate group, isopropyl carbonate group and phenyl carbonate group.

One or plural hydroxyl groups in β-D-glucopyranosyl group as the group represented by X2 in the Compound (5) may be acylated or carbamated. Particularly, one or plural hydroxyl groups in the group may be acylated with a group or groups selected from alkanoyl groups with 2 to 20 carbon atoms (preferably 2 to 6 carbon atoms), lower alkoxy-carbonyl groups and benzoyl group. Such β-D-glucopyranosyl group includes for example 6-acetyl-β-D-glucopyranosyl group and 6-carboxymethoxy-β-D-glucopyranosyl group. Further, the number of hydroxyl groups to be acylated is preferably one to 3.

the group represented by X2 is particularly preferably β-D-glucopyranosyl group, 6-acetyl-β-D-glucopyranosyl group, 6-carboxymethoxy-β-D-glucopyranosyl group and 6-carboethoxy-β-D-glucopyranosyl group.

The group represented by Y2 is preferably a lower alkyl group and a perfluoro-lower alkyl group, particularly preferably trifluoromethyl group and methyl group.

The group represented by Z2 is preferably a halo-lower alkyl group with 2 to 6 carbon atoms. Additionally preferably, the alkyl group is branched. The substitution with halogeno groups may satisfactorily be a single substitution or plural substitutions. The substitution with one to three halogeno groups is preferable. Additionally, the positions for the substitution with halogeno groups are not particularly limited. Particularly, fluoro-lower alkyl groups are preferable, more preferably including monofluoroethyl, monofluoropropyl, monofluoroisopropyl, difluoroisopropyl and trifluoroisopropyl. 1,3-Difluoroisopropyl group is particularly preferable. Further, the group represented by Z2 is preferably a group except for perfluoro-lower alkyl groups.

The groups represented as R21 through R25 are preferably lower alkyl groups with one to 6 carbon atoms, lower alkylthio groups with one to 6 carbon atoms, lower alkoxy groups with one to 6 carbon atoms and halogeno groups, particularly preferably methyl group, ethyl group, methoxy group, ethoxy group and fluorine. Among them, most preferably, R23 represents these groups.

In the Compound (5), preferably, X2 is β-D-glucopyranosyl group (where one or plural hydroxyl groups may be acylated with a group or groups selected from alkanoyl groups with 2 to 20 carbon atoms, lower alkoxy-carbonyl groups and benzoyl group); Y2 is trifluoromethyl group; and Z2 is a halo-lower alkyl group.

In the Compound (5), preferably, X2 is β-D-glucopyranosyl group (where one or plural hydroxyl groups may be acylated with a group or groups selected from alkanoyl groups with 2 to 20 carbon atoms, lower alkoxy-carbonyl groups and benzoyl group); Y2 istrifluoromethyl group; and Z2 is a fluoro-lower alkyl group.

In the Compound (5), preferably, X2 is β-D-glucopyranosyl group (where one or plural hydroxyl groups may be acylated with a group or groups selected from alkanoyl groups with 2 to 20 carbon atoms, lower alkoxy-carbonyl groups and benzoyl group); Y2 is methyl group; and Z2 is a halo-lower alkyl group.

In the Compound (5), preferably, X2 is β-D-glucopyranosyl group (where one or plural hydroxyl groups may be acylated with a group or groups selected from alkanoyl groups with 2 to 20 carbon atoms, lower alkoxy-carbonyl groups and benzoyl group); Y2 is methyl group; and Z2 is a fluoro-lower alkyl group.

In the Compound (5), preferably, X2 is 6-acetyl-β-D-glucopyranosyl group; Y2 is trifluoromethyl group; and Z2 is a fluoro-lower alkyl group.

In the Compound (5), preferably, X2 is 6-carbomethoxy-β-D-glucopyranosyl group; Y2 is trifluoromethyl group; and Z2 is a fluoro-lower alkyl group.

In the Compound (5), preferably, X2 is 6-acetyl-β-D-glucopyranosyl group; Y2 is methyl group; and Z2 is a fluoro-lower alkyl group.

In the Compound (5), preferably, X2 is 6-carbomethoxy-β-D-glucopyranosyl group; Y2 is methyl group; and Z2 is a fluoro-lower alkyl group.

Particularly, the Compound (5) preferably includes the following compounds and pharmaceutically acceptable salts thereof.

4-((4-Ethylphenyl)methyl)-1-(1,3-difluoro-2-propyl)-5-(trifluoromethyl)-1H-pyrazole-3-o-β-D-glucopyranoside;
4'-((4'-Ethylphenyl)methyl)-1'-(1',3'-difluoro-2'-propyl)-5'-(trifluoromethyl)-1H-pyrazole-3'-o-(6-o-acetyl-β-D-glucopyranoside);
4'-((4'-Ethylphenyl)methyl)-1'-(1',3'-difluoro-2'-propyl)-5'-(trifluoromethyl)-1H-pyrazole-3'-o-(6-o-methoxycarbonyl-β-D-glucopyranoside);
4-((4-Ethylphenyl)methyl)-1-(1,3-difluoro-2-propyl)-5-methyl-1H-pyrazole-3-o-β-D-glucopyranoside;
4'-((4'-Ethylphenyl)methyl)-1'-(1',3'-difluoro-2'-propyl)-5'-methyl-1H-pyrazole-3'-o-(6-o-acetyl-β-D-glucopyranoside);
4-((4'-Ethylphenyl)methyl)-1'-(1',3'-difluoro-2'-propyl)-5'-methyl-1H-pyrazole-3'-o-(6-o-methoxycarbonyl-β-D-glucopyranoside);
4-((4-Ethylphenyl)methyl)-1-(2-monofluoroethyl)-5-(trifluoromethyl)-1H-pyrazole-3-o-β-D-glucopyranoside;
4'-((4'-Ethylphenyl)methyl)-1'-(2-monofluoroethyl)-5'-(trifluoromethyl)-1H-pyrazole-3'-o-(6-o-acetyl-β-D-glucopyranoside);
4'-((4'-Ethylphenyl)methyl)-1'-(2'-monofluoroethyl)-5'-(trifluoromethyl)-1H-pyrazole-3'-o-(6-o-methoxycarbonyl-β-D-glucopyranoside);
4-((4-Ethylphenyl)methyl)-1-(2-monofluoroethyl)-5-methyl-1H-pyrazole-3-o-β-D-glucopyranoside;
4'-((4'-Ethylphenyl)methyl)-1'-(2'-monofluoroethyl)-5'-methyl-1H-pyrazole-3'-o-(6-o-acetyl-β-D-glucopyranoside);
4'-((4'-Ethylphenyl)methyl)-1'-(2'-monofluoroethyl)-5'-methyl-1H-pyrazole-3'-o-(6-o-methoxycarbonyl-β-D-glucopyranoside);
4-((4-Ethylphenyl)methyl)-1-(3-monofluoropropyl)-5-(trifluoromethyl)-1H-pyrazole-3-o-β-D-glucopyranoside;
4'-((4'-Ethylphenyl)methyl)-1'-(3'-monofluoropropyl)-5'-(trifluoromethyl)-1H-pyrazole-3'-o-(6-o-acetyl-β-D-glucopyranoside);
4'-((4'-Ethylphenyl)methyl)-1'-(3'-monofluoropropyl)-5'-(trifluoromethyl)-1H-pyrazole-3'-o-(6-o-methoxycarbonyl-β-D-glucopyranoside);
4-((4-Ethylphenyl)methyl)-1-(3-monofluoropropyl)-5-methyl-1H-pyrazole-3-o-β-D-glucopyranoside;
4'-((4'-Ethylphenyl)methyl)-1'-(3'-monofluoropropyl)-5'-methyl-1H-pyrazole-3'-o-(6-o-acetyl-β-D-glucopyranoside);
4'-((4'-Ethylphenyl)methyl)-1'-(3'-monofluoropropyl)-5'-methyl-1H-pyrazole-3'-o-(6-o-methoxycarbonyl-β-D-glucopyranoside);

Specifically, the following compounds and pharmaceutically acceptable salts thereof are particularly preferable.

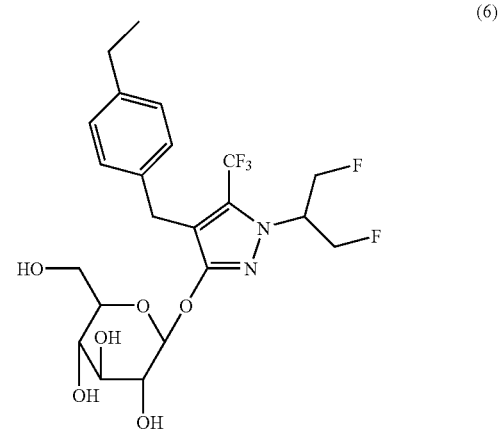

(6)

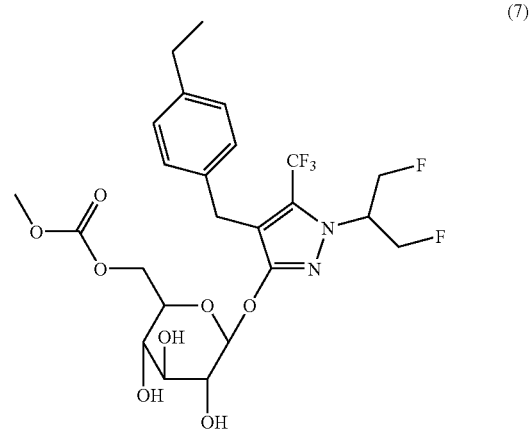

(7)

In case that X2 is β-D-glucopyranosyl group, for example, the following method can be used as an example of the production method of Compound (5).

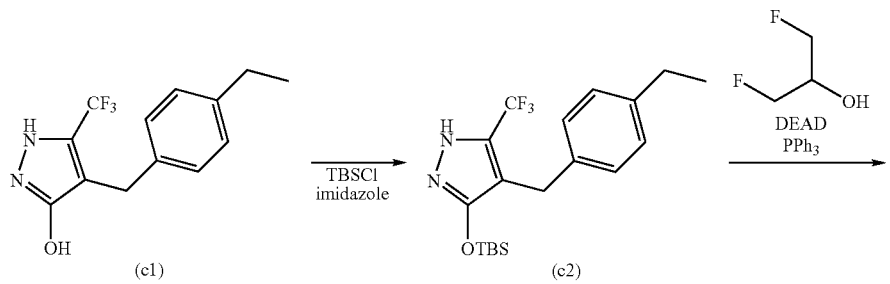

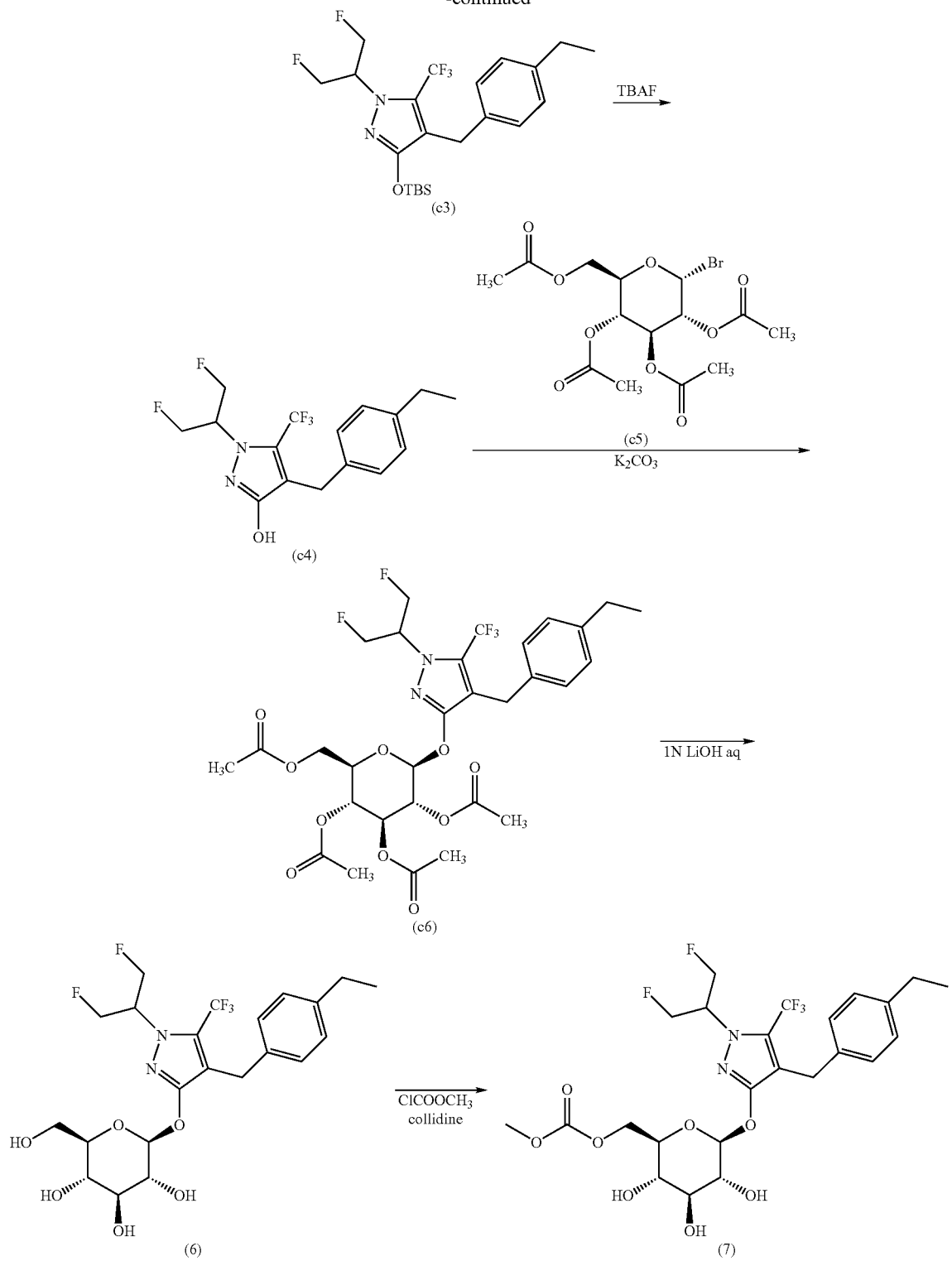

The Compound (5) can be obtained for example from 1,2-dihydro-4-[(4-ethylphenyl)methyl]-5-(trifluoromethyl)-3H-pyrazol-3-one (c1) (prepared by the method described in J. Med. Chem 1996, 39, 3920-3928) as a starting material. Specifically, the hydroxyl group of (c1) is protected with TBS group, to prepare (c2). The nitrogen on the pyrazole is selectively alkylated by Mitsunobu reaction, to obtain (c3). Then, the TBS group of (c3) is deprotected to prepare (c4). Reaction of (c4) with acetobromoglucose (c5) in the presence of potassium carbonate at ambient temperature produces glycoside (c6). The acetyl-protecting group of the glycoside (c6) is deprotected with 1N LiOHaq to prepare pyrazole glycoside (6). Then, (6) is dissolved in collidine for reaction with methyl chlorocarbonate at −10° C., to prepare (7) with methyl-carbonated glucose at the 6-position.

The Compound (5) thus produced by the method described above can be separated and purified readily from the reaction mixtures by general isolation and purification measures, for example solvent extraction, chromatography and crystallization.

The hydroxyl groups in the Compound (5) may be substituted with appropriate substituents provided that the substituted hydroxyl groups can be modified into unsubstituted hydroxyl group in human body. For example, the substituents for the hydroxyl groups include acyl group and carbamate group. The acyl group includes for example alkanoyl groups with 2 to 20 carbon atoms and benzoyl group. The carbamate group includes for example lower alkoxy-carbonyl groups.

In case that the Compound (5) is possibly prepared into salt forms, the salts may satisfactorily be pharmaceutically acceptable. For any acid group in case that such acid group exists in the formula, the salts include for example ammonium salt; salts with alkali metals such as sodium and potassium, salts with alkali earth metals such as calcium and magnesium; aluminum salt; zinc salt; salts with organic amines such as triethylamine, ethanolamine, morpholine, piperidine and dicyclohexylamine, and salts with basic amino acids such as arginine and lysine. For any basic group in case that such basic group exists in the formula, the salts include for example salts with inorganic acids such as hydrochloric acid, sulfuric acid and phosphoric acid; salts with organic carboxylic acids such as oxalic acid, acetic acid, citric acid, malic acid, benzoic acid, maleic acid, fumaric acid, tartaric acid, succinic acid and glutamic acid; and salts with organic sulfonic acids such as methanesulfonic acid and p-toluenesulfonic acid. As to the method for preparing such salts, the Compound (5) is mixed with necessary acids or bases at appropriate ratios in solvents and dispersants, or other salt forms of the Compound (5) may be modified into such salts by cation exchange or anion exchange.

The Compound (5) includes solvates thereof, for example hydrates thereof and alcohol adducts thereof.

(iv) Compound (8) and pharmaceutically acceptable salts thereof

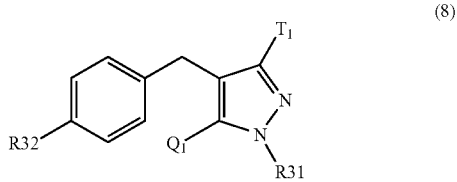

(8)

[in the formulas, R31 is hydrogen atom or a lower alkyl group:
either one of $Q_1$ and $T_1$ is a group represented by the formula

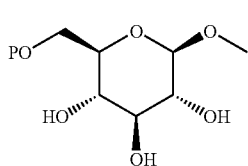

(9)

(where P is hydrogen atom, a lower acyl group, a lower alkoxy-lower acyl group, a lower alkoxy-carbonyl-lower acyl group, a lower alkoxy-carbonyl group or a lower alkoxy-lower alkoxy-carbonyl group), while the remaining one is a lower alkyl group or a halo-lower alkyl group;

R32 is hydrogen atom, a lower alkyl group, a lower alkoxy group, a lower alkylthio group, a halo-lower alkyl group, or a halogen atom.]

The lower alkyl group in the Compound (8) means linear or branched alkyl groups with one to 6 carbon atoms, for example methyl group, ethyl group, propyl group, isopropyl group, butyl group, isobutyl group, sec-butyl group, tert-butyl group, pentyl group, isopentyl group, neopentyl group, tert-pentyl group and hexyl group.

The lower alkoxy group includes linear or branched alkoxy groups with one to 6 carbon atoms, for example methoxy group, ethoxy group, propoxy group, isopropoxy group, butoxy group, isobutoxy group, sec-butoxy group, tert-butoxy group, pentyloxy group, isopentyloxy group, neopentyloxy group, tert-pentyloxy group and hexyloxy group.

The lower alkylthio group includes linear or branched alkylthio groups with one to 6 carbon atoms, for example methylthio group, ethylthio group, propylthio group, isopropylthio group, butylthio group, isobutylthio group, sec-butylthio group, tert-butylthio group, pentylthio group, isopentylthio group, neopentylthio group, tert-pentylthio group and hexylthio group.

The halogen atom includes fluorine atom, chlorine atom, bromine atom or iodine atom. The halo-lower alkyl group means lower alkyl groups substituted with one to three of the halogen atoms described above, which may be the same or different.

The lower acyl group means linear, branched or cyclic acyl groups with 2 to 7 carbon atoms, such as acetyl group, propionyl group, butyryl group, isobutyryl group, pivaloyl group, hexanoyl group and cyclohexylcarbonyl group.

The lower alkoxy-lower acyl group means lower acyl groups substituted with the lower alkoxy groups.

The lower alkoxy-carbonyl group means linear, branched or cyclic alkoxycarbonyl groups with 2 to 7 carbon atoms, such as methoxycarbonyl group, ethoxycarbonyl group, isopropyloxycarbonyl group, isobutyloxycarbonyl group and cyclohexyloxycarbonyl group.

The lower alkoxy-carbonyl-lower acyl group means the lower acyl group after substitution with the lower alkoxy-carbonyl group, such as 3-(ethoxycarbonyl)propionyl group.

The lower alkoxy-lower alkoxy-carbonyl group means the lower alkoxy-carbonyl group after substitution with the lower alkoxy group, such as 2-methoxyethoxycarbonyl group.

The substituent R31 in the Compound (8) is preferably hydrogen atom or a linear or branched alkyl group with one to 3 carbon atoms, more preferably hydrogen atom, ethyl group, propyl group or isopropyl group. The substituent R32 is preferably a linear or branched alkyl group with one to 4 carbon atoms, a linear or branched alkoxy group with one to 3 carbon atoms, or a linear or branched alkylthio group with one to 3 carbon atoms, more preferably ethyl group, ethoxy group, isopropoxy group or methylthio group. Preferably, either one of $Q_1$ and $T_1$ is a linear or branched alkyl group with one to 3 carbon atoms, more preferably methyl group.

Pharmaceutically acceptable salts of the Compound (8) include for example acid addition salts thereof with mineral acids such as hydrochloric acid, hydrobromic acid, hydroiodic acid, sulfuric acid, nitric acid and phosphoric acid; acid addition salts thereof with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid and aspartic acid; and salts thereof with inorganic bases, such as sodium salt and potassium salt.

Preferably, the Compound (8) and pharmaceutically acceptable salts thereof are the compounds described in the Examples 1 to 70 of WO 01/16147 and pharmaceutically acceptable salts thereof.

The Compound (8) can be produced for example by the method described in WO 01/16147. Additionally, the Compound (8) can be prepared into pharmaceutically acceptable salts thereof by general methods.

(v) Compound (10) and pharmaceutically acceptable salts thereof

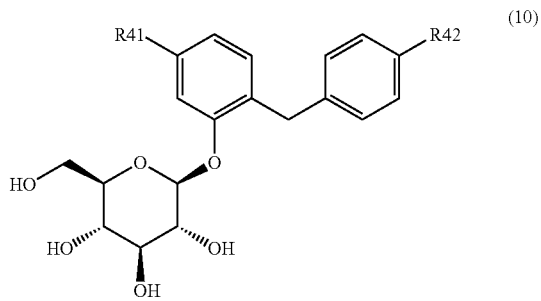

[where R41 is hydrogen atom or a hydroxy-lower alkyl group;

R42 is a lower alkyl group, a lower alkoxy group, a lower alkylthio group, a hydroxy-lower alkyl group, a hydroxy-lower alkoxy group, a hydroxy-lower alkylthio group, a lower alkoxy-lower alkyl group, a lower alkoxy-lower alkoxy group or a lower alkoxy-lower alkylthio group.]

The lower alkyl group in the Compound (10) means a linear or branched alkyl group with one to 6 carbon atoms, for example methyl group, ethyl group, propyl group, isopropyl group, butyl group, isobutyl group, sec-butyl group, tert-butyl group, pentyl group, isopentyl group, neopentyl group, tert-pentyl group and hexyl group. The lower alkoxy group means a linear or branched alkoxy group with one to 6 carbon atoms, for example methoxy group, ethoxy group, propoxy group, isopropoxy group, butoxy group, isobutoxy group, sec-butoxy group, tert-butoxy group, pentyloxy group, isopentyloxy group, neopentyloxy group, tert-pentyloxy group and hexyloxy group. The lower alkylthio group means a linear or branched alkylthio group with one to 6 carbon atoms, for example methylthio group, ethylthio group, propylthio group, isopropylthio group, butylthio group, isobutylthio group, sec-butylthio group, tert-butylthio group, pentylthio group, isopentylthio group, neopentylthio group, tert-pentylthio group and hexylthio group. The hydroxy-lower alkyl group in the Compound (10) means a linear or branched hydroxy-alkyl group with one to 6 carbon atoms, for example hydroxymethyl group, 2-hydroxyethyl group, 1-hydroxyethyl group, 3-hydroxypropyl group, 2-hydroxypropyl group, 1-hydroxypropyl group, 2-hydroxy-1-methylethyl group, 4-hydroxybutyl group, 3-hydroxybutyl group, 2-hydroxybutyl group, 1-hydroxybutyl group, 5-hydroxypentyl group, 4-hydroxypentyl group, 3-hydroxypentyl group, 2-hydroxypentyl group, 1-hydroxypentyl group, 6-hydroxyhexyl group, 5-hydroxyhexyl group, 4-hydroxyhexyl group, 3-hydroxyhexyl group, 2-hydroxyhexyl group and 1-hydroxyhexyl group. The hydroxy-lower alkoxy group means a linear or branched hydroxy-alkoxy group with one to 6 carbon atoms, for example 2-hydroxyethoxy group, 3-hydroxypropoxy group, 2-hydroxypropoxy group, 2-hydroxy-1-methylethoxy group, 4-hydroxybutoxy group, 3-hydroxybutoxy group, 2-hydroxybutoxy group, 5-hydroxypentyloxy group, 4-hydroxypentyloxy group, 3-hydroxypentyloxy group, 2-hydroxypentyloxy group, 6-hydroxyhexyloxy group, 5-hydroxyhexyloxy group, 4-hydroxyhexyloxy group, 3-hydroxyhexyloxy group and 2-hydroxyhexyloxy group. The hydroxy-lower alkylthio group means a linear or branched hydroxy-alkylthio group with one to 6 carbon atoms, for example hydroxymethylthio group, 2-hydroxyethylthio group, 1-hydroxyethylthio group, 3-hydroxypropylthio group, 2-hydroxypropylthio group, 1-hydroxypropylthio group, 2-hydroxy-1-methylethylthio group, 4-hydroxybutylthio group, 3-hydroxybutylthio group, 2-hydroxybutylthio group, 1-hydroxybutylthio group, 5-hydroxypentylthio group, 4-hydroxypentylthio group, 3-hydroxypentylthio group, 2-hydroxypentylthio group, 1-hydroxypentylthio group, 6-hydroxyhexylthio group, 5-hydroxyhexylthio group, 4-hydroxyhexylthio group, 3-hydroxyhexylthio group, 2-hydroxyhexylthio group and 1-hydroxyhexylthio group. The lower alkoxy-lower alkyl group means the hydroxy-lower alkyl group after o-alkylation with the lower alkyl groups. The lower alkoxy-lower alkoxy group means the hydroxy-lower alkoxy group after o-alkylation with the lower alkyl groups. The lower alkoxy-lower alkylthio group means the hydroxy-lower alkylthio group after o-alkylation with the lower alkyl groups.

The protective group of the hydroxyl groups in the Compound (10) means protective groups of hydroxyl group for use in general organic synthetic reaction, such as benzyl group, methoxymethyl group and acetyl group.

The substituent R41 in the Compound (10) is preferably hydrogen atom or a hydroxy-alkyl group with one to 3 carbon atoms. The substituent R42 is preferably a lower alkyl group, a lower alkoxy group or a hydroxy-alkyl group, more preferably an alkyl group with one to 4 carbon atoms, an alkoxy group with one to 3 carbon atoms or a hydroxy-alkyl group with one to 3 carbon atoms.

Pharmaceutically acceptable salts of the Compound (10) include salts thereof with inorganic bases, such as sodium salt and potassium salt.

The Compound (10) includes the hydrate thereof and solvates thereof with solvents acceptable for pharmaceutical products, such as ethanol.

The Compound (10) and pharmaceutically acceptable salts thereof preferably include the compounds described in the Examples 1 to 12 in WO 01/68660 and pharmaceutically acceptable salts thereof.

Specifically, 2-(4-ethylbenzyl)-5-hydroxymethylphenyl-β-D-glucopyranoside and pharmaceutically acceptable salts thereof are particularly preferable.

The Compound (10) can be produced for example by the method described in WO 01/68660. Additionally, the Compound (10) can be prepared into pharmaceutically acceptable salts thereof by general methods.

(vi) Compound (11) and pharmaceutically acceptable salts thereof

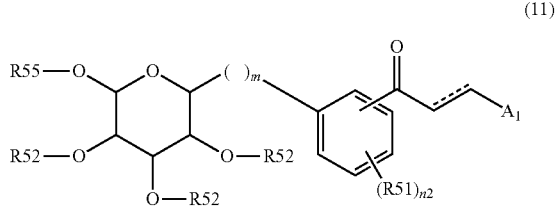

[where R51 represents hydrogen, hydroxyl group, a lower alkyl, lower alkoxy or

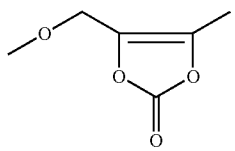
(12)

R52 represents hydrogen, —COO— lower alkyl,

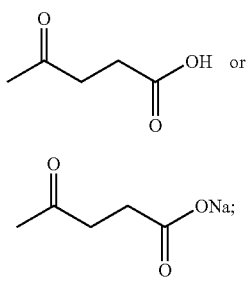
(13)

(14)

R55 represents hydroxymethyl, —CH$_2$OCOO— lower alkyl,

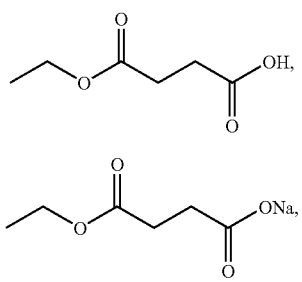
(15)

(16)

—CH$_2$OSO$_3$H, —COOH, —COONa;

m represents 0 or 1;

n2 represents 0, 1, 2, or 3;

A1 represents the following cyclic structure:

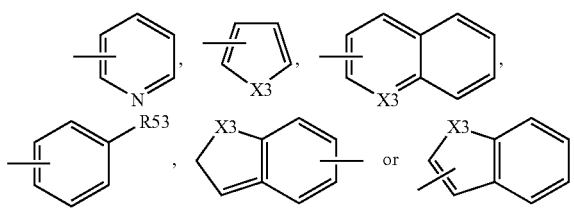

(where X3 represents oxygen, nitrogen or sulfur; when m is 0, R53 is a lower alkyl; when m is 1, R53 is a lower alkyl, hydroxyl group or a lower alkoxy group);

----- represents single bond or double bond.]

The lower alkyl group in the Compound (11) means a linear or branched alkyl group with one to 5 carbon atoms, such as methyl group, ethyl group, propyl group, isopropyl group, butyl group, isobutyl group, sec-butyl group, tert-butyl group, pentyl group, isopentyl group, neopentyl group and tert-pentyl group.

The lower alkoxy group in the Compound (11) means a linear or branched alkoxy group with one to 5 carbon atoms, such as methoxy group, ethoxy group, propoxy group, isopropoxy group, butoxy group, isobutoxy group, sec-butoxy group, tert-butoxy group, pentoxy group, isopentoxy group, neopentoxy group and tert-pentoxy group.

Pharmaceutically acceptable salts of the Compound (11) include for example sodium salt and potassium salt thereof as the salts thereof with inorganic bases. In case that A$_1$ contains a pyridine base, the pharmaceutically acceptable salts thereof include salts with inorganic acids and salts with organic acids. The salts with inorganic acids include salts with hydrochloric acid and sulfuric acid, and the salts with organic acids include salts with acetic acid, succinic acid and fumaric acid.

The Compound (11) preferably includes the compounds described as the Compound Nos. 1 through 58 in the publication of JP-A-2001-288178 and pharmaceutically acceptable salts thereof.

Among them, 3-(benzo[b]furan-5-yl)-3'-(6-o-methoxycarbonyl-β-D-glucopyranosyl)-6'-hydroxy-4'-methoxypropiophenone (the Compound No. 5 in the publication) and pharmaceutically acceptable salts thereof are particularly preferable.

The Compound (11) can be produced for example by the method described in JP-A-2001-288178. Additionally, the Compound (11) can be prepared into pharmaceutically acceptable salts thereof by general methods.

(vii) Compound (22) and pharmaceutically acceptable salts thereof

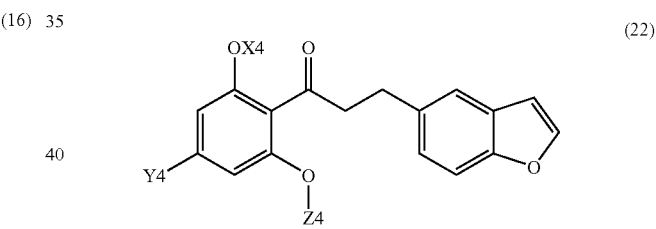
(22)

[in the formula, OX4 represents hydroxyl group optionally protected;

Y4 represents a lower alkyl group;

Z4 represents β-D-glucopyranosyl group where one or plural hydroxyl groups may be protected.]

In case that OX4 is a protected hydroxyl group in the Compound (22), the protective group may satisfactorily be any protective group for phenolic hydroxyl group. Specifically, the protective group includes for example lower alkoxy-lower alkyl groups such as methoxymethyl group; allyl groups; acyl groups such as lower alkanoyl groups, lower alkoxy-lower alkanoyl groups, lower alkoxy-carbonyl groups, lower alkoxy-lower alkoxy-carbonyl groups and arylcarbonyl groups (for example, benzoyl group), preferably acyl groups such as lower alkanoyl groups, lower alkoxy-lower alkanoyl groups, lower alkoxy-carbonyl groups and lower alkoxy-lower alkoxy-carbonyl groups. Particularly, the protective group is a lower alkanoyl group and a lower alkoxy-carbonyl group.

In case that Z4 is β-D-glucopyranosyl group where one or plural hydroxyl groups are protected in the Compound (22), routine hydroxyl group-protecting groups readily removable by general methods such as acid treatment, hydrolysis and reduction can be used. The β-D-glucopyranosyl group where one or plural hydroxyl groups are protected with such groups includes for example [1] β-D-glucopyranosyl group with one or plural hydroxyl groups acylated; [2] β-D-glucopyranosyl group where two hydroxyl groups together with the protective groups thereof form 1-lower alkoxy-lower alkylidenedioxy group, benzylidenedioxy group, phosphinicodioxy group, carbonyldioxy group or the like; or [3] β-D-glucopyranosyl group where one or two hydroxyl groups are acylated and two hydroxyl groups together with the protective groups thereof form 1-lower alkoxy-lower alkylidenedioxy group, benzylidenedioxy group, phosphinicodioxy group, or carbonyldioxy group. However, the protective group of the hydroxyl groups in β-D-glucopyranosyl group is not limited to them. Any protective group with a function giving hydroxyl group after administration into biological organisms and subsequent deprotection, a function enabling ready absorption in biological organisms or ready administration into biological organisms or a function raising solubility in fats or solubility in water can be used preferably.

When the hydroxyl groups in β-D-glucopyranosyl group are acylated, preferably, lower alkanoyl groups, lower alkoxy-lower alkanoyl groups, lower alkoxy-carbonyl groups, lower alkoxy-lower alkoxy-carbonyl groups, aryl-carbonyl groups (for example, benzoyl group) and the like can be used as the acyl group. As the acyl group, additionally, residues prepared by removing hydroxyl group from one carboxyl group in amino acids (the amino groups, carboxyl groups and/or hydroxyl groups existing in the residues may be protected) may also be used. The residues prepared by removing hydroxyl group from one carboxyl group in amino acids include for example residues prepared by removing hydroxyl group from one carboxyl group in a naturally occurring amino acid such as aspartic acid, glutamic acid, glutamine, serine, sarcosine, proline, phenylalanine, leucine, isoleucine, glycine, tryptophan, cysteine, histidine, tyrosine, or valine, or an enantiomer or a racemic mixture thereof.

β-D-glucopyranosyl group where two hydroxyl groups together with the protective groups thereof form 1-lower alkoxy-lower alkylidenedioxy group, benzylidenedioxy group, phosphinicodioxy group, carbonyldioxy group or the like includes β-D-glucopyranosyl group where the hydroxyl groups of β-D-glucopyranosyl group at 4- and 6-positions together with the protective groups form 1-lower alkoxy-lower alkylidenedioxy group, benzylidenedioxy group, phosphinicodioxy group, carbonyldioxy group or the like, namely β-D-glucopyranosyl group forming the structure represented by the following formula

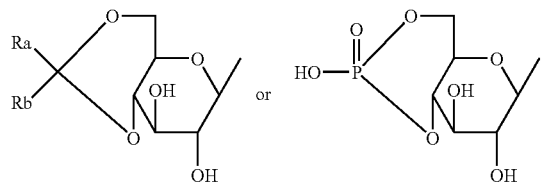

(where one of Ra and Rb represents hydrogen atom or a lower alkyl group and the other represents a lower alkoxy group; or one of Ra and Rb represents hydrogen atom and the other represents phenyl group; or Ra and Rb together form oxo group).

In case that two hydroxyl groups of β-D-glucopyranosyl group together with the protective groups thereof form 1-lower alkoxy-lower alkylidenedioxy group, the 1-lower alkoxy-lower alkylidenedioxy group is preferably 1-lower alkoxy-ethylidenedioxy group. Particularly, 1-methoxyethylidenedioxy group, 1-ethoxyethylidenedioxy group and the like can be used preferably.

Y4 in the Compound (22) is preferably an alkyl group with one to 4 carbon atoms, particularly preferably methyl group and ethyl group.

Specific compounds of the Compound (22) include such compound where Z4 is β-D-glucopyranosyl group where one or plural hydroxyl groups may be acylated with a group or groups selected from lower alkanoyl groups, lower alkoxy-carbonyl groups, lower alkoxy-lower alkanoyl groups and lower alkoxy-lower alkoxy-carbonyl groups, or such compound where Z4 is β-D-glucopyranosyl group where two hydroxyl groups together with the protective groups thereof form 1-lower alkoxy-lower alkylidenedioxy group or phosphinicodioxy group.

More specific compounds thereof include such compound where z4 is β-D-glucopyranosyl group where the hydroxyl group at 2-position, 2- and 3-positions, 4-position or 6-position may be acylated with a group or groups selected from lower alkanoyl groups, lower alkoxy-carbonyl groups, lower alkoxy-lower alkanoyl groups and lower alkoxy-lower alkoxy-carbonyl groups, or such compound where Z4 is β-D-glucopyranosyl group where the hydroxyl groups at 4- and 6-positions together with the protective groups thereof form 1-lower alkoxy-lower alkylidenedioxy group or phosphinicodioxy group.

Preferable compounds as the Compound (22) include compounds where OX4 is hydroxyl group, a lower alkanoyloxy group or a lower alkoxy-carbonyloxy group; Z4 is β-D-glucopyranosyl group, 2-o-(lower alkanoyl)-β-D-glucopyranosyl group, 2,3-di-o-(lower alkanoyl)-β-D-glucopyranosyl group, 4-o-(lower alkoxy-carbonyl)-β-D-glucopyranosyl group, 6-o-(lower alkanoyl)-β-D-glucopyranosyl group, 6-o-(lower alkoxy-carbonyl)-β-D-glucopyranosyl group, 6-o-(lower alkoxy-lower alkanoyl)-β-D-glucopyranosyl group, 6-o-(lower alkoxy-lower alkoxy-carbonyl)-β-D-glucopyranosyl group, 4,6-o-(1-lower alkoxy-lower alkylidene)-β-D-glucopyranosyl group or 4,6-o-phosphinico-β-D-glucopyranosyl group.

More preferable compounds as the Compound (22) include compounds where OX4 is hydroxyl group or a lower alkanoyloxy group; Z4 is β-D-glucopyranosyl group, 2,3-di-o-(lower alkanoyl)-β-D-glucopyranosyl group, 4-o-(lower alkoxy-carbonyl)-β-D-glucopyranosyl group, 6-o-(lower alkoxycarbonyl)-β-D-glucopyranosyl group, 4,6-o-(1-lower alkoxy-lower alkylidene)-β-D-glucopyranosyl group, or 4,6-o-phosphinico-β-D-glucopyranosyl group.

Still more preferable compounds as the Compound (22) include compounds where OX4 is hydroxyl group; Y4 is methyl group or ethyl group; Z4 is β-D-glucopyranosyl group, 4-o-(lower alkoxy-carbonyl)-β-D-glucopyranosyl group, 6-o-(lower alkoxy-carbonyl)-β-D-glucopyranosyl group, 4,6-o-(1-lower alkoxy-lower alkylidene)-β-D-glucopyranosyl group, or 4,6-o-phosphinico-β-D-glucopyranosyl group.

Particularly preferable compounds as the Compound (22) include compounds where Z4 is β-D-glucopyranosyl group or 6-o-(lower alkoxy-carbonyl)-β-D-glucopyranosyl group.

The Compound (22) can be used in the free form or a pharmaceutically acceptable salt thereof for the purpose of the invention. The pharmaceutically acceptable salt thereof includes alkali metal salts thereof, such as sodium salt, mineral acid salts such as hydrochloride salt, and organic acid salts such as tosylate salts.

Additionally, the Compound (22) and the pharmaceutically acceptable salt thereof include any of intramolecular salts thereof, and their solvates and hydrates.

The Compound (22) preferably includes the compounds described in Examples 1 to 22 in the publication of JP-A-10-237089 and pharmaceutically acceptable salts thereof.

Among them, particularly, 3-(5-benzo[b]furanyl)-2'-(6-o-methoxycarbonyl-β-D-glucopyranosyloxy)-6'-hydroxy-4'-methylpropiophenone (Example 2 in the publication) and pharmaceutically acceptable salts thereof are preferable.

The Compound (22) can be produced for example by the method described in JP-A-10-237089. Additionally, the Compound (22) can be prepared into pharmaceutically acceptable salts thereof by general methods.

For the prophylactic and therapeutic agent of diabetes mellitus in accordance with the invention, the combination of an inhibitor of renal glucose reabsorption and a hypoglycemic agent is preferably a combination where the inhibitor of renal glucose reabsorption is at least one selected from (i) the Compounds (1) and (2) and pharmaceutically acceptable salts thereof;

(ii) the Compounds (1A) and (2A) and pharmaceutically acceptable salts thereof;

(iii) the Compound (5) and pharmaceutically acceptable salts thereof; and (iv) the Compound (8) and pharmaceutically acceptable salts thereof;

and where the hypoglycemic agent is at least one selected from sulfonylureas and biguanides.

More preferably, the combination is a combination where the inhibitor of renal glucose reabsorption is at least one selected from pyrazole derivatives and pharmaceutically acceptable salts thereof represented by the formulas (3), (3a), (4a), (7), (10-A), (12-A), (14-A) and (16-A) and the hypoglycemic agent is at least one selected from sulfonylureas and biguanides.

In case of such combination, the prophylactic and therapeutic agent of the invention is superior to a single sulfonylurea therapy or a single biguanide therapy by which the hyperglycemia after meals cannot be suppressed, because the combination can suppress hyperglycemia after meals. Compared with a single therapy with an inhibitor of renal glucose reabsorption, further, the combination can extend the sustainability of the pharmaceutical effect so that the combination is very useful for glycemic control.

Additionally, another preferable combination of the inhibitor of renal glucose reabsorption and the hypoglycemic agent is a combination where the inhibitor of renal glucose reabsorption is at least one selected from the Compound (22) and pharmaceutically acceptable salts thereof and the hypoglycemic agent is meglitinide analogues. More preferably, the combination is a combination where the inhibitor of renal glucose reabsorption is at least one selected from 3-(5-benzo[b]furanyl)-2'-(6-o-methoxycarbonyl-β-D-glucopyranosyloxy)-6'-hydroxy-4'-methylpropiophenone and pharmaceutically acceptable salts thereof and the hypoglycemic agent is meglitinide analogues.

In case of such combination, the prophylactic and therapeutic agent of the invention can more readily suppress hyperglycemia after meals than the single use of meglitinide analogues with short sustainability of pharmaceutical effect does, so that the combination is very useful for glycemic control.

The prophylactic and therapeutic agent of diabetes mellitus in accordance with the invention has a far greater anti-diabetic action compared with the single use of hypoglycemic agents in the related art, and is useful as a prophylactic and therapeutic agent of diabetes mellitus (for example, true diabetes mellitus such as type 1 diabetes mellitus and type 2 diabetes mellitus), and various symptoms due to hyperglycemia (for example, diabetic complications such as diabetic nephropathy, diabetic neuropathy and diabetic retinopathy) for mammalian animals (for example, mouse, rat, hamster, rabbit, cat, dog, cow, sheep, monkey and humans).

The prophylactic and therapeutic agent of diabetes mellitus in accordance with the invention may be any preparation at least containing one active component containing an inhibitor of renal glucose reabsorption and one active component containing a hypoglycemic agent or any preparation containing such active components in mixture. A combination of preparations each containing each active component may also be encompassed within the scope of the prophylactic and therapeutic agent of diabetes mellitus in accordance with the invention. Further, preparations containing other anti-diabetic agents and the like (third and fourth pharmaceutical components) may also be encompassed within the scope of the invention as long as the preparations contain the active components of the invention.

In the prophylactic and therapeutic agent of diabetes mellitus in accordance with the invention, the ratio of an inhibitor of renal glucose reabsorption and a hypoglycemic agent varies within a wide range, in a manner dependent on a variety of factors, for example the desirable dose and the pharmaceutically acceptable carrier to be used therein. In case that both the two agents are combined in a single preparation or in case that the two agents are separately prepared into different preparations, the content of a hypoglycemic agent is preferably about 0.01 to 100 per the content (by weight) of an inhibitor of renal glucose reabsorption, which is defined as 1. Additionally, components contained in the prophylactic and therapeutic agent of diabetes mellitus in accordance with the invention except for an inhibitor of renal glucose reabsorption and a hypoglycemic agent should preferably be about 0.001 to 1000, more preferably about 0.01 to 100, per the content (by weight) of the inhibitor of renal glucose reabsorption, which is defined as 1. In case that the prophylactic and therapeutic agent of diabetes mellitus in accordance with the invention is to be administered in the form of a single preparation to patients, the prophylactic and therapeutic agent can be administered so that the individual components might be within the ranges described above. Additionally in case that the individual active components are to be administered in the form of separate, different preparations, the ratio described above can be used as the ratio on average.

Per one preparation in accordance with the invention, preferably, about 0.01 to 1000 mg of an inhibitor of renal glucose reabsorption can be contained.

The dosage regimen of the prophylactic and therapeutic agent of diabetes mellitus in accordance with the invention is not specifically limited. The prophylactic and therapeutic agent of diabetes mellitus in accordance with the invention can be administered at a safe and necessary dose by intravenous, intra-arterial, subcutaneous and intra-muscular injections, and administration via infusion drops, instantaneously in one portion or by infusion. Additionally, the dosage regimen of the prophylactic and therapeutic agent of diabetes mellitus in accordance with the invention may be given either parenterally or orally. In terms of pain to patients and the like, preparations except for insulin preparations are preferably given orally. However, a combination of preparations with different dosage regimens is also satisfactory.

The prophylactic and therapeutic agent of diabetes mellitus in accordance with the invention may be prepared into for example oral preparations of various dosage forms, for example tablets, capsules, granules, powders, troches and liquids. These preparations can be prepared by methods known per se. Any of the active components and the preparations in accordance with the invention may contain pharmaceutically acceptable carriers, diluents, vehicles, disintegrators, lubricants, flowability-enhancing agents and other substances required for preparations. An appropriate combination is used for formulating these preparations, so that the preparations can be produced.

In the prophylactic and therapeutic agent of diabetes mellitus in accordance with the invention, an inhibitor of renal glucose reabsorption and a hypoglycemic agent can be simultaneously given or sequentially given in any order. A dosage regimen, a sequence and an interval practically preferable can be selected, depending on the preparations of individual pharmaceutical agents to be used, the time required for the expression of the pharmaceutical effect, and the conditions of individual patients to be treated, in overall view of routine techniques and in terms of the information described in this specification. For example, the following dosage regimens and the like are listed. [1] Administration of a composition containing an inhibitor of renal glucose reabsorption and a hypoglycemic agent, namely in the form of a single preparation. [2] Simultaneous administration of two types of preparations obtained by separately formulating an inhibitor of renal glucose reabsorption and a hypoglycemic agent into different preparations, by the same dosage route. [3] Administration of two types of preparations obtained by separately formulating an inhibitor of renal glucose reabsorption and a hypoglycemic agent into different preparations at an interval (for example, in a sequential order of an inhibitor of renal glucose reabsorption and a hypoglycemic agent or in the reverse order thereof) by the same dosage route. [4] Simultaneous administration of two types of preparations obtained by separately formulating an inhibitor of renal glucose reabsorption and a hypoglycemic agent into different preparations, by different dosage routes. [5] Administration of two types of preparations obtained by separately formulating an inhibitor of renal glucose reabsorption and a hypoglycemic agent into different preparations at an interval (for example, in an sequential order of an inhibitor of renal glucose reabsorption and a hypoglycemic agent or in the reverse order thereof) by different dosage routes.

The therapeutic unit practically preferable can vary, depending on each of the individual preparations of an inhibitor of renal glucose reabsorption and a hypoglycemic agent, the condition of each patient to be treated, namely outine markers such as blood glucose value, blood lipid concentration, and blood glycohemoglobin concentration. The therapeutic unit optimal for given conditions can appropriately be selected using the routine markers and therapeutic unit, from the standpoint of the information described in this specification. For example, the compounds represented by the general formulas (or by formulas) (1), (2), (3), (4), (3a), (4a), (1A), (2A), (3A), (4A), (10-A), (12-A), (14-A), (16-A), (5), (6), (7), (8), (10), (11) and (22) and pharmaceutically acceptable salts thereof as inhibitors of renal glucose reabsorption are preferably dosed at about 1 to 500 mg/day. In this case, thus, the dose of a hypoglycemic agent can be about 0.01 to 50,000 mg/day. For combined use of another agent, any of dosage regimens such as simultaneous administration of both the two agents, pre-administration or post-administration of an inhibitor of renal glucose reabsorption, and plural combinations thereof may be possible. Preferably, these individual pharmaceutical agents are given up to three times per day. Unless hypoglycemic symptoms or other adverse effects cause contraindication, such therapy may satisfactorily be repeated.

Additionally, the invention includes a commercial package including a combination agent including a combination of an inhibitor of renal glucose reabsorption and a hypoglycemic agent, along with an instruction insert about the combination agent, telling that the combination agent can be or should be used for the prophylaxis and therapy of diabetes mellitus.

The invention is now described in detail in the following examples. However, these examples never limit the invention.

In the following examples, the following inhibitors of renal glucose reabsorption were used: the inhibitor A of renal glucose reabsorption as represented by the formula (3):
1'-cyclobutyl-4'-[(4-ethylphenyl)methyl]-5'-trifluoromethyl-1H-pyrazole-3'-o-β-D-glucopyranoside; and
the inhibitor B of renal glucose reabsorption as represented by the formula (22), which is one of propiophenone derivatives:
3-(5-benzo[b]furanyl)-2'-(6-o-methoxycarbonyl-β-D-glucopyranosyloxy)-6'-hydroxy-4'-methylpropiophenone.

Example I

Wistar rats (age of 7 weeks; male) were divided into groups with matched body weights. After 17-hour starvation, glucose was orally given at 1 g/kg to the animals. Immediately after the administration, the inhibitor A of renal glucose reabsorption or the inhibitor B of renal glucose reabsorption (A at 30 mg/kg or 60 mg/kg; B at 30 mg/kg or 80 mg/kg) or glibenclamide (1 mg/kg or 2 mg/kg) or nateglinide (50 mg/kg or 80 mg/kg) was orally given. Additionally, a group on the combined use of both of an inhibitor of renal glucose reabsorption and a hypoglycemic agent was also prepared. A vehicle was orally given to a control group after glucose administration.

Blood glucose was measured in a time course. As apparently shown in FIG. 1, consequently, glibenclamide (1 mg/kg) did not suppress hyperglycemia immediately after glucose loading (30 minutes), but lowered blood glucose 120 minutes after glucose loading and thereafter, compared with the vehicle group. However, even the increase of the dose (2 mg/kg) did not change changed the pattern of glycemic suppression. The inhibitor A of renal glucose reabsorption (30 mg/kg) suppressed hyperglycemia observed in the vehicle group immediately after glucose loading (30 minutes) but did not lower the blood glucose level 120 minutes after glucose loading and thereafter as greatly as glibenclamide did. The pattern of glycemic suppression did not change even when the dose was elevated (60 mg/kg). In case of using glibenclamide (1 mg/kg) and the inhibitor A of renal glucose reabsorption (30 mg/kg) in combination, blood glucose levels immediately after glucose loading (30 minutes) and 120 minutes after glucose loading and thereafter were both lower than the levels in the vehicle group.

Figure 2:
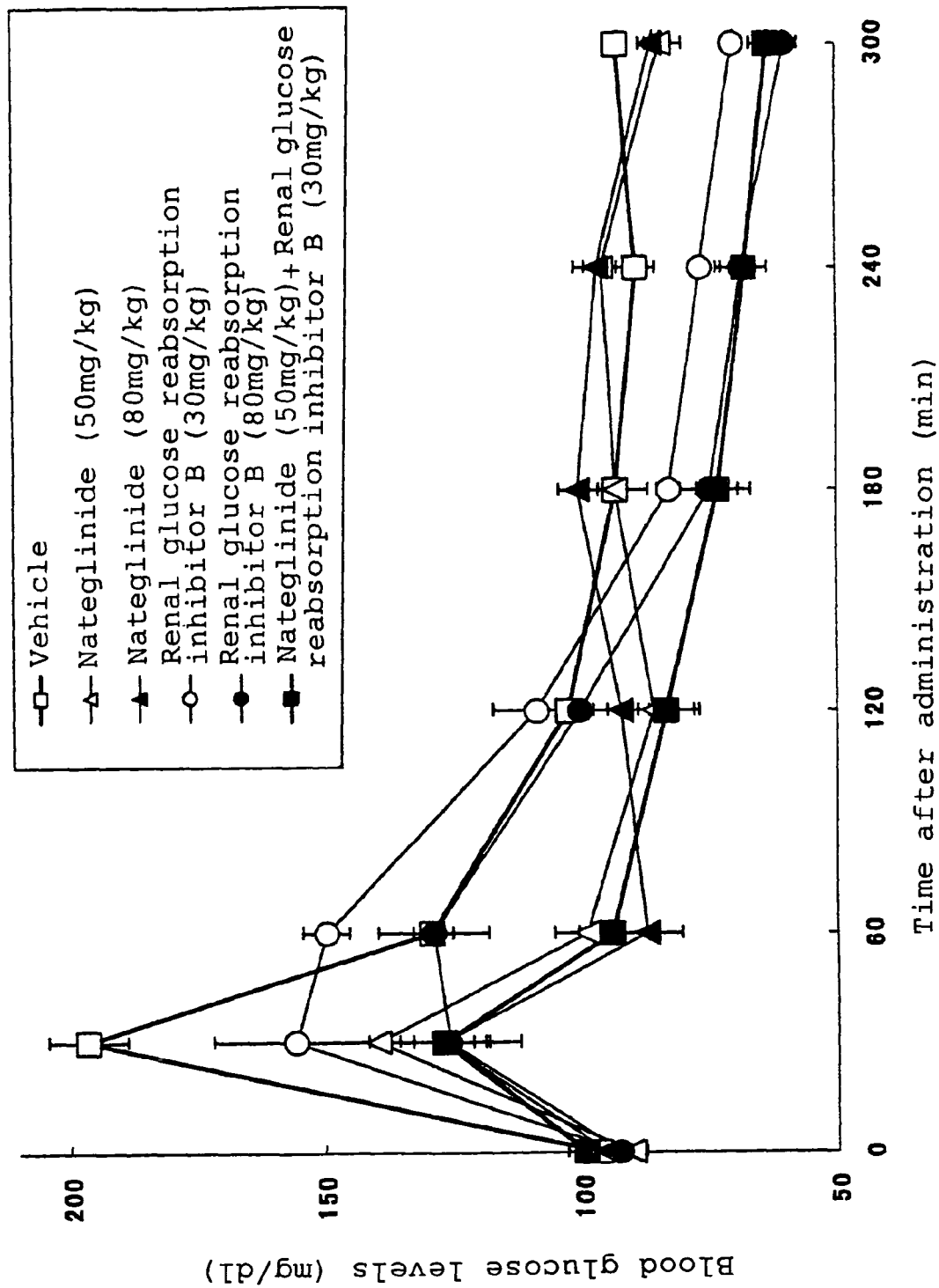
FIG. 2 shows graphs depicting the effect of a combined use of nateglinide and an inhibitor B of renal glucose reabsorption in Example I (mean±standard deviation; N=6 in each group).

As apparently shown in FIG. 2, nateglinide (50 mg/kg) more highly suppressed hyperglycemia immediately after glucose loading (30 minutes and 60 minutes), compared with the vehicle-dosed group, but did not lower the blood glucose level 120 minutes after glucose loading and thereafter. Further, the pattern of glycemic suppression did not change even by the elevation of the dose (80 mg/kg). The hyperglycemia 30 minutes after glucose loading in the group given with the inhibitor B of renal glucose reabsorption (30 mg/kg) was not reduced as greatly as in the case of nateglinide, while the blood glucose level 60 minutes later was similar to that in the vehicle-dosed group. The blood glucose level 180 minutes after glucose loading and thereafter was lower than that in the vehicle-dosed group. This pattern of glycemic suppression was also observed in the group with the increase of the dose (80 mg/kg). In case of using nateglinide (50 mg/kg) and the inhibitor B of renal glucose reabsorption (30 mg/kg), the blood glucose levels immediately after glucose loading (30 minutes and 60 minutes) and the blood glucose level 180 minutes later and thereafter were all lowered than those in the vehicle group. This apparently indicates that such strict glycemic control as never been obtained by the existing hypoglycemic agents can be obtained by the combined use of the inhibitors of renal glucose reabsorption and the existing hypoglycemic agents at the tests using the glucose-loaded rats.

Example II

KK mice (age of 25 weeks; male) fed with a commercially available high-calories feed for breeding (CMF; Oriental Yeast) were divided into groups with matched body weights. After starvation for 17 hours, glucose was orally given at 1 g/kg. Immediately thereafter, the inhibitor A of renal glucose reabsorption (30 mg/kg or 45 mg/kg) or metformin (200 mg/kg or 300 mg/kg) was orally given. Additionally, a group given with the inhibitor A of renal glucose reabsorption (30 mg/kg) and metformin (200 mg/kg) was prepared. A vehicle was orally given to a control group after glucose dosing.

Blood glucose level was assayed in a time course. As apparently shown in FIG. 3, consequently, metformin (200 mg/kg) dosed did not suppress the increase of blood glucose in the mice 30 minutes after glucose loading but suppressed the increase 60 minutes later and thereafter. The pattern of glycemic suppression did not change even when the dose was elevated (300 mg/kg). The administration of the inhibitor A of renal glucose reabsorption (30 mg/kg) alone could suppress hyperglycemia 30 minutes and 60 minutes after glucose loading, compared with the control group, but could not suppress the blood glucose level 2 hours later and thereafter. Additionally, the pattern of glycemic suppression did not change even when the dose was elevated (45 mg/kg). However, the blood glucose in the group given with a combination of the inhibitor A of renal glucose reabsorption (30 mg/kg) and metformin (200 mg/kg) was suppressed at all the assay points, compared with the blood glucose level in the control group. This apparently indicates that such strict glycemic control as has never been obtained by the existing hypoglycemic agents can be obtained by the combined use of the inhibitor of renal glucose reabsorption and the existing hypoglycemic agent at the test using the glucose-loaded mice.

Figure 3:
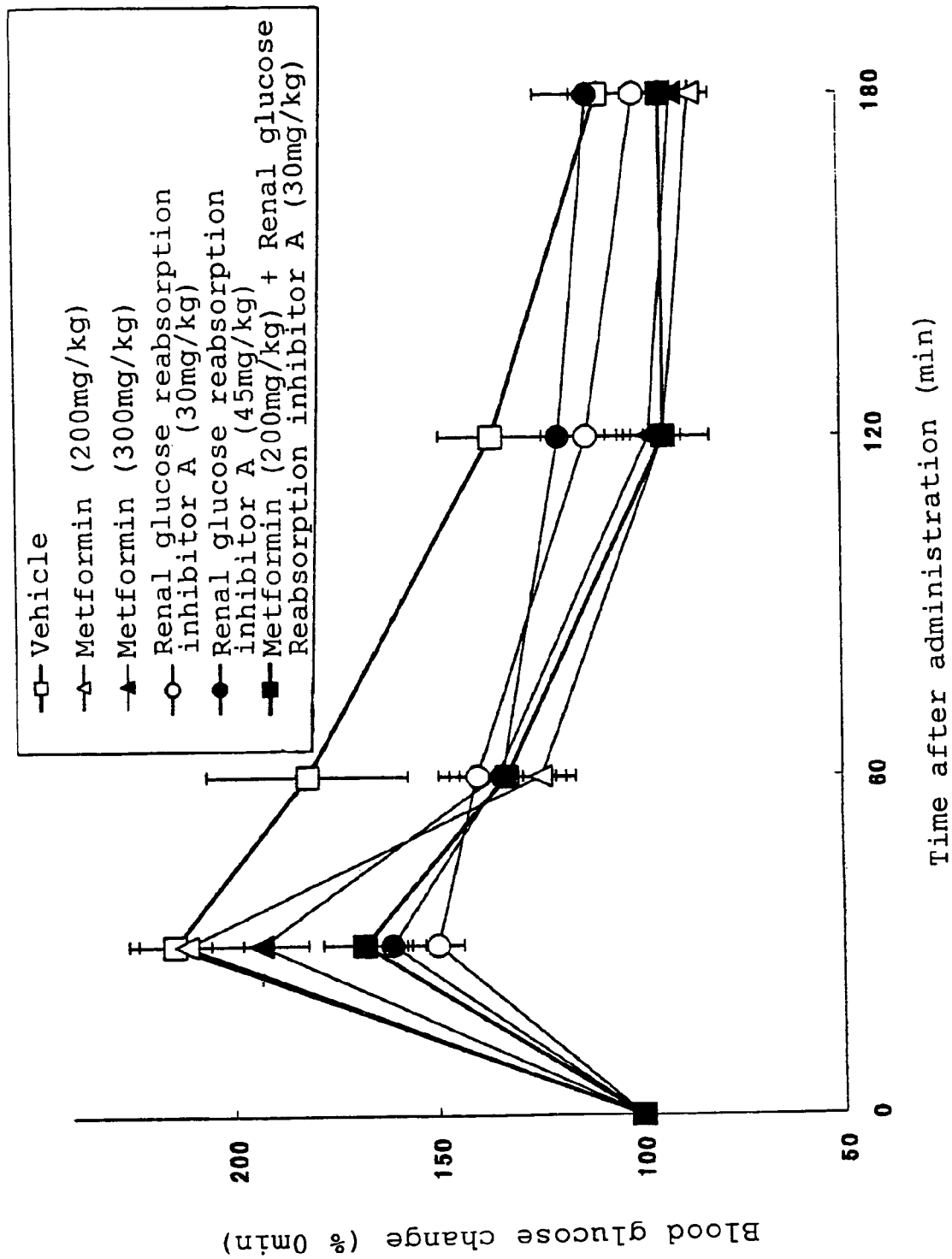
FIG. 3 shows graphs depicting the effect of a combined use of metformin and an inhibitor A of renal glucose reabsorption in Example II (mean±standard deviation; N=4 in each group).

As described above, the results in the Examples as shown in FIGS. 1, 2 and 3 indicate that the methods using combinations of the inhibitors of renal glucose reabsorption and the existing hypoglycemic agents in accordance with the invention can achieve strict glycemic control immediately after glucose loading and thereafter in the glucose-loaded animals as hyperglycemic models after meals and that the method could produce a higher effect, compared with their single use.

Example III

Type 2 diabetic model GK rats (age of 7 weeks; male) were divided into groups with matched blood glucose levels and body weights, for once daily oral administration of the inhibitor A of renal glucose reabsorption (30 mg/kg) or glibenclamide at 3 or 6 mg/kg. Further, a group given with a combination of the inhibitor A of renal glucose reabsorption at 30 mg/kg and glibenclamide at 3 mg/kg was prepared. These agents were orally given once daily at the same time period as in the group administered with a single one agent. Only a vehicle was given orally to a control group. On day 25 after the start of administration, blood glucose was assayed sequentially, to compare the groups in terms of the resulting blood glucose levels. The results are shown in FIG. 4.

Figure 4:
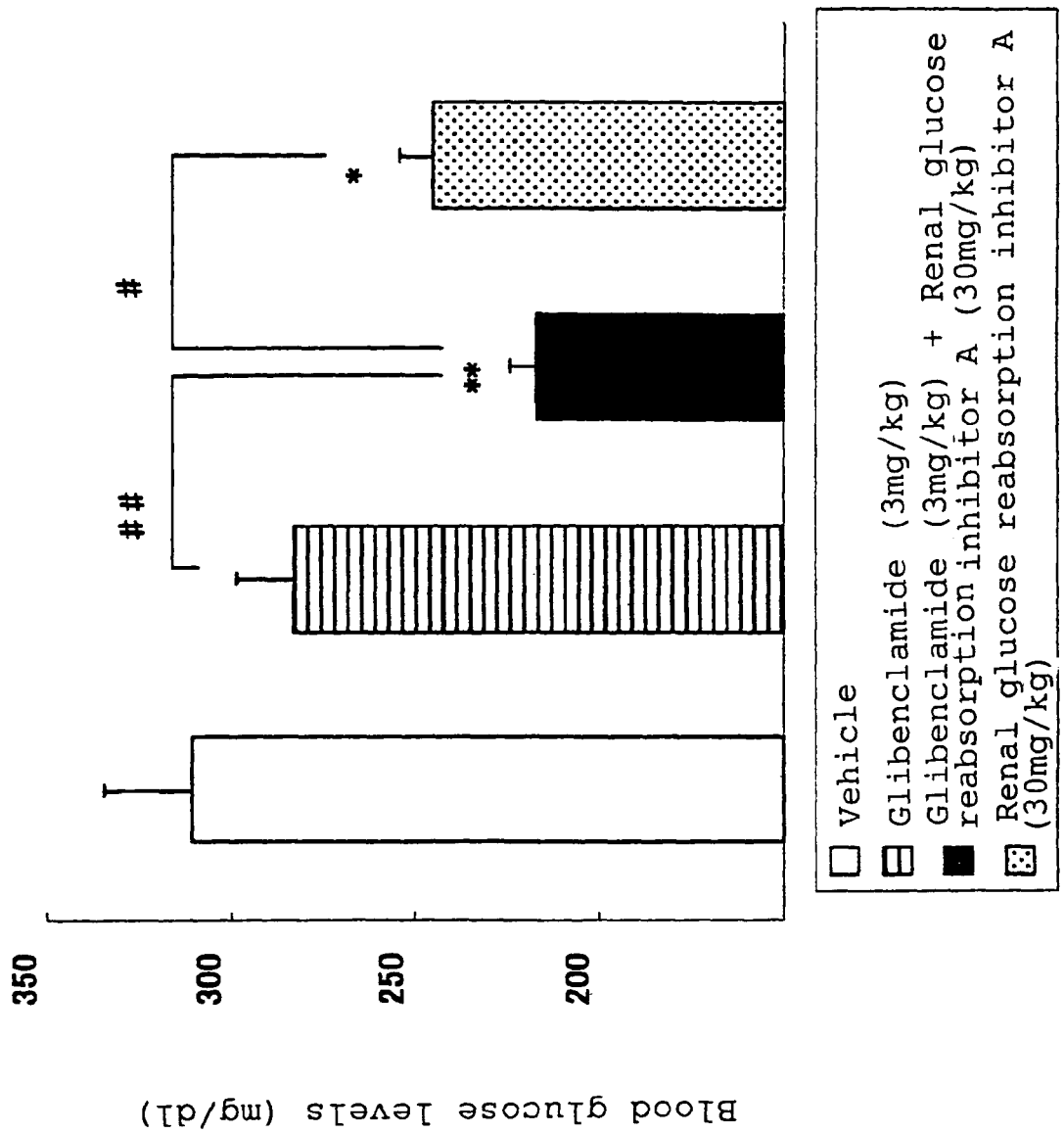
FIG. 4 shows graphs depicting the effect of a combined use of glibenclamide and an inhibitor A of renal glucose reabsorption in Example III (mean±standard deviation; N=8 in each group; *, #: P<0.05; **; ##: P<0.01; *, **: with significance from vehicle group).

As shown in FIG. 4, hyperglycemia was observed in the vehicle-dosed group. In the group given glibenclamide alone (3 mg/kg), however, no difference was observed from the vehicle-dosed group in terms of the blood glucose levels. Additionally, even the elevation of the dose (6 mg/kg) did not produce any difference in blood glucose level from the vehicle-dosed group. In this diabetic model animals, no effect of glibenclamide was observed. The blood glucose level in the group given the inhibitor of renal glucose reabsorption alone was significantly lowered, compared with the group given the vehicle. The effect of the administration of the inhibitor of renal glucose reabsorption alone was observed in this model animals. In the group given the combination of glibenclamide and the inhibitor of renal glucose reabsorption (given at 3 mg/kg and 30 mg/kg, respectively), meanwhile, the blood glucose level was significantly lowered, compared with not only the vehicle-dosed group and the group given glibenclamide alone but also the group given the inhibitor of renal glucose reabsorption alone. In other words, the condition of diabetes mellitus in the group given the combination was greatly improved, compared with the group given the inhibitor of renal glucose reabsorption alone, although glibenclamide was not observed to be effective. The combined use of the existing hypoglycemic agent and the inhibitor of renal glucose reabsorption could show a synergistic therapeutic effect on the conditions of diabetic mellitus, as never been obtained by the administration of the existing hypoglycemic agent alone.

Example IV

Type 2 diabetes model db/db mice (age 6 weeks) were fed and kept with a feed twice daily over one hour starting 9 am and one hour starting 3 pm, for one week. Then, the mice were divided into groups with matched blood glucose levels and body weights. Subsequently, the inhibitor B of renal glucose reabsorption at 80 mg/kg or nateglinide at 80 mg/kg was orally given, immediately before feeding twice daily. Only a vehicle was orally given immediately before feeding twice daily to the animals of a control group. On day 25 from the start of administration, the mice of the individual experimental groups were starved for 17 hours and then orally given glucose (1 g/kg) and nateglinide (50 mg/kg). Blood glucose levels were measured before and after the administration, to examine whether or not the hypoglycemic action of nateglinide could be observed (nateglinide load test). The results are shown in Table I.

TABLE I

Blood glucose levels (mg/dl) at the time of nateglinide load test

| Compound successively dosed | Blood glucose level before loading | Blood glucose level 30 minutes after loading | Blood glucose level 120 minutes after loading |
|---|---|---|---|
| Vehicle (N = 4) | 134 ± 10 | 239 ± 25 | 126 ± 8 |
| Nateglinide | 158 ± 12 | 259 ± 18 | 144 ± 20 |
| Inhibitor B of renal glucose reabsorption | 131 ± 6 | 172 ± 14*,# | 103 ± 5 |

Mean ± SD;
N = 5 for groups except for vehicle group;
*p < 0.05 for difference from vehicle group;
p < 0.05 for difference from nateglinide group.

As shown in Table I, the blood glucose levels immediately before the nateglinide load test did not differ in these groups. 30 minutes after loading with glucose and nateglinide, nateglinide greatly suppressed hyperglycemia due to glucose loading in the group given the inhibitor B of renal glucose reabsorption, compared with the vehicle-dosed group and the nateglinide-dosed group. In other words, it was found that the long-term administration of the inhibitor of renal glucose reabsorption distinctly activated the nateglinide sensitivity of the diabetic model animals, so that the combined use of the inhibitor of renal glucose reabsorption and nateglinide could produce an effect as never been anticipated from the single use.

Example V

Type 2 diabetes model Zucker diabetic fatty rats (age 15 weeks) were divided into groups with matched blood glucose levels and body weights. Subsequently, the inhibitor A of renal glucose reabsorption at 30 mg/kg or metformin at 200 mg/kg was orally given twice daily. Further, a group to be on a combined use of the inhibitor A of renal glucose reabsorption (30 mg/kg) and metformin (200 mg/kg) was prepared. The agents were orally given twice daily at the same time period as in the case of the groups administered with a single one of these agents. Only a vehicle was orally given twice daily to the animals in a control group. On day 39 from the start of administration, the animals were starved for 18 hours. Then, pancreas was resected from the animals, for the assay of insulin in pancreas homogenates by ELISA, to compare the groups in terms of insulin content in pancreas. The results are shown in FIG. 5.

Figure 5:
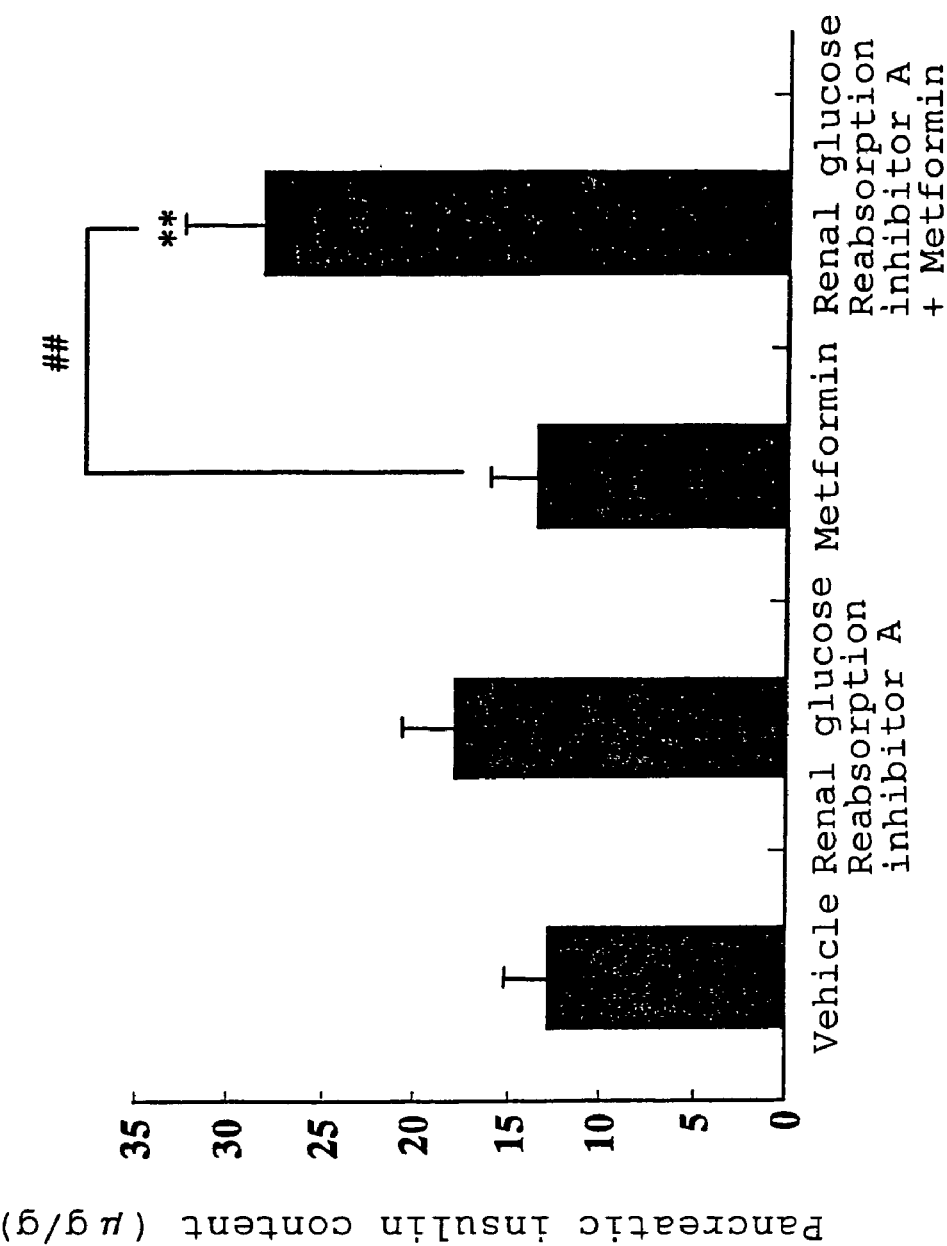
FIG. 5 shows graphs depicting the effect of a combined use of metformin and an inhibitor A of renal glucose reabsorption in Example V (mean±standard deviation; N=6 in each group; , ##: p<0.01; : with significance from vehicle group).

As shown in FIG. 5, no difference was observed in insulin content in spleen among the vehicle group, the group given the inhibitor A of renal glucose reabsorption and the group given metformin. However, the insulin content in the group given the combination of the inhibitor A of renal glucose reabsorption and metformin was so high, compared with the remaining groups. Zucker diabetic fatty rat is a type 2 diabetic model animal, where the sustainment of hyperglycemic conditions induces a high concentration of glycated hemoglobin so that the aging of the model animal involves the decrease of the insulin content in pancreas. In other words, it was shown that a synergistic therapeutic effect of diabetes mellitus and a synergistic effect on the prevention of the progress of diabetes mellitus as have never been obtained by the administration of any one of them could be obtained from the combined use of the inhibitor of renal glucose reabsorption and metformin.

Production Example 1

Synthesis of 1'-cyclobutyl-4'-[(4-ethylphenyl)methyl]-5'-trifluoromethyl-1H-pyrazole-3'-o-β-D-glucopyranoside Step 1

Synthesis of 4-[(4-ethylphenyl)methyl]-5-trifluoromethyl-3-o-t-butyldimethylsilyl-1H-pyrazole 1,2-Dihydro-4-[(4-ethylphenyl)methyl]-5-trifluoromethyl-3H-pyrazol-3-one (4.76 g; 17.6 mmol) (prepared by the method described in J. Med. Chem 1996, 39, 3920-3928) and imidazole (1.57 g; 23.1 mmol) were dissolved in dimethylformamide (20 ml). t-Butyldimethylsilyl chloride (2.98 g; 19.8 mmol) was added to the resulting mixture. The mixture was stirred at room temperature for 30 minutes. After the addition of water (100 ml), the mixture was extracted with ethyl acetate and hexane (a mixture solvent at 2:1) three times. The organic phase was washed with water, dried over sodium sulfate and concentrated, to give the desired compound. (6.9 g, 17.9 mmol; quantitative).

$^1$H-NMR (300 MHz, CDCl$_3$) δ: 0.21 (6H, s), 0.93 (9H, s), 1.19 (3H, t, J=7.6 Hz), 2.59 (2H, q, J=7.6 Hz), 3.74 (2H, s), 7.09 (4H, m). ESI-MS(m/z) 269[(M-TBS)$^-$].

Step 2

Synthesis of 1-cyclobutyl-4-[(4-ethylphenyl)methyl]-5-trifluoromethyl-3-o-t-butyldimethylsilyl-1H-pyrazole 4-[(4-Ethylphenyl)methyl]-5-trifluoromethyl-3-o-t-butyldimethylsilyl-1H-pyrazole (2.5 g; 6.5 mmol), triphenylphosphine (1.9 g; 7.2 mmol) and cyclobutanol (0.71 g; 9.8 mmol) were dissolved in anhydrous tetrahydrofuran (15 ml), the mixture was stirred at room temperature. A 40% toluene solution of diethyl azodicarboxylate (3.4 ml; 7.5 mmol) was gradually added. Twenty minutes later, the resulting mixture was concentrated, to which hexane (20 ml) was added. The precipitate was filtered, followed by concentration. By purification on a silica gel column (hexane→5% ethyl acetate/hexane), the objective compound was obtained. (1.4 g, 3.3 mmol, 51%).

$^1$H-NMR (300 MHz, CDCl$_3$) δ: 0.27 (6H, s), 0.96 (9H, s), 1.20 (3H, t, J=7.5 Hz), 2.26-2.34 (2H, m), 2.59 (2H, q, J=7.5 Hz), 2.54-2.67 (2H, m), 3.72 (2H, s), 4.67 (1H, quint, J=8.1 Hz), 7.06 (2H, d, J=8.5 Hz), 7.10 (2H, d, J=8.5 Hz). ESI-MS (m/z) [323 (M-TBS)$^-$].

Step 3

Synthesis of 1-cyclobutyl-4-[(4-ethylphenyl)methyl]-5-trifluoromethyl-1H-pyrazole 1-Cyclobutyl-4-[(4-ethylphenyl)methyl]-5-trifluoromethyl-3-o-t-butyldimethylsilyl-1H-pyrazole (1.4 g; 3.3 mmol) was dissolved in tetrahydrofuran (25 ml) and methanol (5 ml), to which aqueous 1 M HCl solution (5 ml) was added, for agitation overnight at room temperature. After the addition of water (100 ml), the mixture was extracted three times with 10 ml of ethyl acetate. After drying over anhydrous sodium sulfate and concentration, the residue was purified on a silica gel column chromatography (hexane→5% ethyl acetate/hexane) to give the desired compound (0.84 g; 2.6 mmol). (78%)

$^1$H-NMR (300 MHz, CDCl$_3$) δ: 1.20 (3H, t, J=7.5 Hz), 1.70-1.90 (2H, m), 2.28-2.36 (2H, m), 2.59 (2H, q, J=7.5 Hz), 2.55-2.68 (2H, m), 3.80 (2H, s), 4.75 (1H, pseudo quint, J=8.1 Hz), 7.10 (2H, d, J=8.8 Hz), 7.18 (2H, d, J=8.8 Hz). ESI-MS (m/z) [325 (M+H)$^+$], [323 (M–H)$^-$].

Step 4

Synthesis of 1'-cyclobutyl-4'-[(4-ethylphenyl)methyl]-5'-trifluoromethyl-1H-pyrazole-3'-o-(2,3,4,6-tetraacetyl)-β-D-glucopyranoside Water (2 mL) and chloroform (10 mL) were added to 1-cyclobutyl-4-[(4-ethylphenyl)methyl]-5-trifluoromethyl-1H-pyrazole (0.84 g; 2.6 mmol), 2,3,4,6-o-tetraacetyl-α-D-glucopyranosyl bromide (1.5 g; 3.7 mmol), benzyl chloride tri-n-butylammonium (0.10 g; 0.32 mmol) and potassium carbonate (3.23 g; 23 mmol). The mixture was stirred at room temperature for 18 hours. The organic layer was purified by silica gel column chromatography (hexane→hexane:ethyl acetate=10:1 to 2:1), to obtain 2.1 g of a crude product mainly containing the objective compound, which was then used for the following reaction.

$^1$H-NMR (300 MHz, CDCl$_3$) δ: 1.19 (3H, t, J=7.6 Hz), 1.72-1.84 (2H, m), 1.89 (3H, s), 2.03 (3H, s), 2.04 (3H, s), 2.06 (3H, s), 2.29-2.38 (2H, m), 2.58 (2H, q, J=7.6 Hz), 2.58-2.68 (2H, m), 3.72 (2H, s), 3.88 (1H, ddd, J=9.9, 4.9, 2.3 Hz), 4.11-4.17 (1H, m), 4.26 (1H, dd, J=12.3, 9.4 Hz), 4.70-4.76 (1H, m), 5.15-5.22 (1H, m), 5.28-5.32 (2H, m), 5.64-5.66 (1H, m), 7.06 (4H, s). ESI-MS (m/z) [655 (M+H)$^+$].

Step 5

Synthesis of 1'-cyclobutyl-4'-[(4-ethylphenyl)methyl]-5'-trifluoromethyl-1H-pyrazole-3'-o-β-D-glucopyranoside A crude product (2.1 g) of 1'-cyclobutyl-4'-[(4-ethylphenyl)methyl]-5'-trifluoromethyl-1H-pyrazole-3'-o-(2,3,4,6-tetraacetyl)-β-D-glucopyranoside was dissolved in ethanol (20 ml), followed by addition of 4 ml of aqueous 4N NaOH solution. The mixture was stirred at room temperature. After one hour, aqueous saturated sodium chloride (50 ml) and water (10 ml) were added, and the mixture was extracted three times with 20 ml of ethyl acetate. After concentration, the extract was purified on a silica gel column chromatography (dichloromethane→10% methanol/dichloromethane) to give the desired compound. (0.63 g, 1.3 mmol). (50%)

$^1$H-NMR (300 MHz, CD$_3$OD) δ=1.18 (3H, t, J=7.6 Hz), 1.79-1.89 (2H, m), 2.28-2.36 (2H, m), 2.57 (2H, q, J=7.6 Hz), 2.60-2.72 (2H, m), 3.37-3.45 (4H, m), 3.65-3.71 (1H, m), 3.81 (2H, s), 3.81-3.86 (1H, m), 5.39-5.41 (1H, m), 7.06 (4H, s). MS (ESI) m/z[487 (M+H)$^+$], [485 (M−H)$^-$].

Production Example 2

Synthesis of 1'-cyclobutyl-4'-[(4-ethylphenyl)methyl]-5'-trifluoromethyl-1H-pyrazole-3'-o-(6-carbomethoxy)-β-D-glucopyranoside 1'-Cyclobutyl-4'-[(4-ethylphenyl)methyl]-5'-trifluoromethyl-1H-pyrazole-3'-o-β-D-glucopyranoside (0.18 g; 0.32 mmol) was dissolved in 2,4,6-collidine (2.0 ml) and cooled to −50° C. Methyl chlorocarbonate (0.035 ml; 0.45 mmol) was added to the resulting mixture, which was then back to room temperature over 0.5 hour. 27 hours later, ethyl acetate (20 ml) and aqueous 1M HCl solution (20 ml) were added and the mixture was extracted with ethyl acetate. After drying and concentration, the residue was purified on a silica gel column chromatography (hexane:ethyl acetate 1:1 to 1:3→ethyl acetate) to give the desired compound. (0.12 g, 0.20 mmol). (62%)

$^1$H-NMR (300 MHz, CDCl$_3$) δ: 1.20 (3H, t, J=7.6 Hz), 1.71-1.86 (2H, m), 2.29-2.38 (2H, m), 2.48 (1H, d, J=2.6 Hz), 2.60-2.68 (2H, m), 2.60 (2H, q, J=7.6 Hz), 2.68 (1H, s), 2.72 (1H, s), 3.49-3.65 (4H, m), 3.72 (1H, d, J=15.2 Hz), 3.79 (3H, s), 3.87 (1H, d, J=15.2 Hz), 4.32 (1H, dd, J=12.0, 2.1 Hz), 4.48 (1H, dd, J=12.0, 4.1 Hz), 4.74 (1H, pseudo quint, J=8.4 Hz), 5.22 (1H, d, J=7.9 Hz), 7.10 (4H, s). MS (ESI) m/z [545 (M+H)$^+$], [543 (M−H)$^-$].

Production Example 3

Synthesis

1'-cyclopentyl-4'-[(4-ethylphenyl)methyl]-5'-trifluoromethyl-1H-pyrazole-3'-o-β-D-glucopyranoside Step 1

Synthesis of 1-cyclopentyl-4-[(4-ethylphenyl)methyl]-5-trifluoromethyl-3-o-t-butyldimethylsilyl-1H-pyrazole In the same manner as in the Step 2 of the Production Example 1 except for the use of cyclopentanol instead of cyclobutanol, the desired compound was obtained. (86%)

$^1$H-NMR (300 MHz, CDCl$_3$) δ: 0.23 (6H, s), 0.94 (9H, s), 1.20 (3H, t, J=7.6 Hz), 1.55-1.70 (2H, m), 1.80-2.05 (6H, m), 2.59 (2H, q, J=7.6 Hz), 3.72 (2H, s), 4.54-4.66 (1H, m), 7.06 (2H, d, J=8.4 Hz), 7.11 (2H, d, J=8.4 Hz).

Step 2

Synthesis of 1-cyclopentyl-4-[(4-ethylphenyl)methyl]-5-trifluoromethyl-1H-pyrazole In the same manner as in the Step 3 of the Production Example 1, the desired compound was obtained from 1-cyclopentyl-4-[(4-ethylphenyl)methyl]-5-trifluoromethyl-3-o-t-butyldimethylsilyl-1H-pyrazole. (95%)

$^1$H-NMR (300 MHz, CDCl$_3$) δ: 1.20 (3H, t, J=7.6 Hz), 1.50-1.70 (2H, m), 1.80-2.10 (6H, m), 2.60 (2H, q, J=7.6 Hz), 3.79 (2H, s), 4.53-4.68 (1H, m), 7.09 (2H, d, J=8.1 Hz), 7.17 (2H, d, J=8.1 Hz), 10.1-10.2 (1H, br). MS (ESI) m/z 339[(M+H)$^+$], [337 (M−H)$^-$].

Step 3

Synthesis of 1-cyclopentyl-4'-[(4-ethylphenyl)methyl]-5'-trifluoromethyl-1H-pyrazole-3'-o-(2,3,4,6-tetraacetyl)-β-D-glucopyranoside In the same manner as in the Step 4 of the Production Example 1, a crude product of the desired compound was obtained from 1-cyclopentyl-4-[(4-ethylphenyl)methyl]-5-trifluoromethyl-1H-pyrazole.

$^1$H-NMR (300 MHz, CDCl$^3$) δ: 1.19 (3H, t, J=7.6 Hz), 1.60-1.68 (2H, m), 1.88 (3H, s), 2.02 (3H, s), 2.04 (3H, s), 2.06 (3H, s), 1.98-2.0 (2H, m), 2.58 (2H, q, J=7.6 Hz), 3.72 (2H, s), 3.80-3.85 (1H, m), 4.11 (1H, dd, J=8.5, 3.8 Hz), 4.25 (1H, dd, J=12.5, 4.8 Hz), 4.65 (1H, pseudo quint, J=7.0 Hz), 5.14-5.20 (1H, m), 5.24-5.30 (2H, m), 5.56-5.59 (1H, m), 7.06 (4H, s). MS (ESI) m/z[669 (M+H)$^+$].

Step 4

Synthesis of 1'-cyclopentyl-4'-[(4-ethylphenyl)methyl]-5'-trifluoromethyl-1H-pyrazole-3'-o-β-D-glucopyranoside In the same manner as in the Step 5 of the Production Example 1, the desired compound was obtained via the hydrolysis of a crude product of 1'-cyclopentyl-4'-[(4-ethylphenyl)methyl]-5'-trifluoromethyl-1H-pyrazole-3'-o-(2,3,4,6-tetraacetyl)-β-D-glucopyranoside. (90%)

$^1$H-NMR (300 MHz, CD$_3$OD) δ=1.19 (3H, t, J=7.6 Hz), 1.62-1.68 (2H, m), 1.87-2.04 (6H, m), 2.57 (2H, q, J=7.6 Hz), 3.32-3.45 (3H, m), 3.67 (1H, dd, J=12.0, 5.0 Hz), 3.78-3.82 (3H, m), 4.70 (1H, pseudo quint, J=6.9 Hz), 5.30-5.37 (1H, m), 7.06 (4H, s). MS (ESI) m/z[501 (M+H)$^+$], [499 (M−H)$^-$].

Production Example 4

Synthesis of 1'-cyclopentyl-4'-[(4-ethylphenyl)methyl]-5'-trifluoromethyl-1H-pyrazole-3'-o-(6-carbomethoxy)-β-D-glucopyranoside In the same manner as in the Step 6 of Production example 1, the desired compound was obtained via the reaction of 1'-cyclopentyl-4'-[(4-ethylphenyl)methyl]-5'-trifluoromethyl-1H-pyrazole-3'-o-β-D-glucopyranoside with methyl chlorocarbonate. (67%)

$^1$H-NMR (300 MHz, CDCl$_3$) δ: 1.20 (3H, t, J=7.5 Hz), 1.60-1.70 (2H, m), 1.84-1.94 (2H, m), 1.98-2.04 (4H, m), 2.55 (1H, d, J=2.3 Hz), 2.60 (2H, q, J=7.5 Hz), 2.75 (1H, d, J=2.1 Hz), 2.85 (1H, d, J=2.6 Hz), 3.47-3.63 (4H, m), 3.72 (1H, dd, J=15.8, 1.2 Hz), 3.78 (3H, s), 3.87 (1H, d, J=15.8 Hz), 4.36 (1H, dd, J=12.0, 1.8 Hz), 4.45 (1H, dd, J=12.0, 4.1 Hz), 4.66 (1H, pseudo quint, J=6.9 Hz), 5.14 (1H, d, J=7.9 Hz), 7.10 (4H, s) MS (ESI) m/z[559 (M+H)$^+$], [557 (M−H)$^-$].

The structures of the compounds obtained in the Production Examples 1 to 4 are shown below.

Compound of Production Example 1

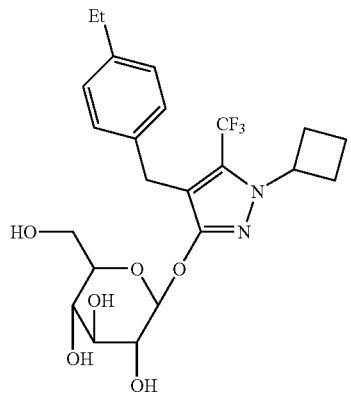

Compound of Production Example 2

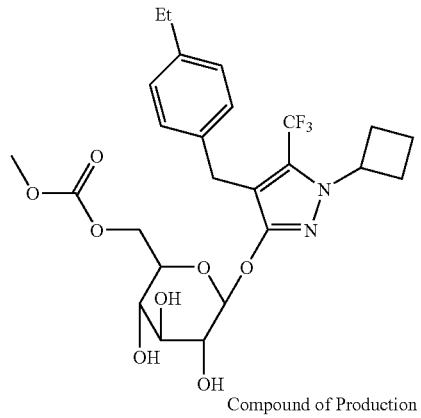

Compound of Production Example 3

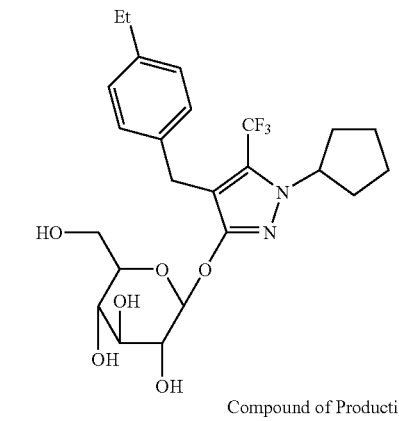

Compound of Production Example 4

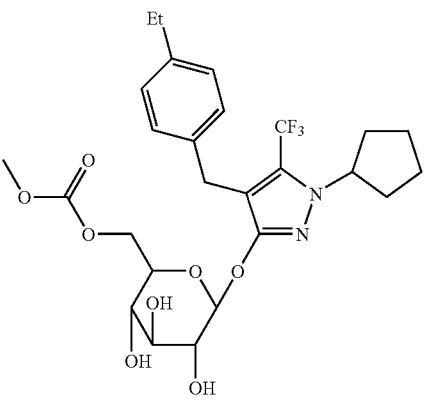

Test Example 1

Evaluation of Urine Sugar Excretion Action in Rats

Male Wistar rats aged 5 weeks (purchased from Charles River Japan, Inc.) were acclimatized in metabolic cages for one week, for use at this experiment. The test compounds suspended in olive oil were prepared into a 20 mg/ml solution to a dose of 5 ml per 1 kg rat body weight.

After the rats were starved for 4 hours, the test compounds were orally given at 100 mg/kg to the rats at 11 am. Immediately after dosing until 24 hours later, urine was collected. The volume of urine was measured. Then, urine sugar concentration was assayed by glucose oxidase method, to calculate the glucose excretion into urine per individual per day.

The results are shown in Table 1.

TABLE 1

| Test Compounds | Urine sugar excretion (mg) |
|---|---|
| Compound of Production Example 2 | 656 |
| Compound of Production Example 4 | 452 |

As apparently shown above, the resulting pyrazole derivatives showed excellent excretion actions of urine sugar.

Production Example 1-A

Synthesis of 4-((4-methylthiophenyl)methyl)-5-(trifluoromethyl)-1H-pyrazole-3-o-β-D-glucopyranoside Step 1

Synthesis of 4'-((4'-methylthiophenyl)methyl)-5'-(trifluoromethyl)-1H-pyrazole-3'-o-(2,3,4,6-o-tetraacetyl)-β-D-glucopyranoside Water (0.1 mL) and chloroform (4 mL) were added to 1,2-dihydro-4-((4-methylthiophenyl)methyl)-5-(trifluoromethyl)-3H-pyrazol-3-one (519 mg; 1.80 mmol) (prepared by the method described in J. Med. Chem 1996, 39, 3920-3928), 2,3,4,6-o-tetraacetyl-β-D-glucopyranosyl bromide (1.258 mg; 3.06 mmol), benzyl chloride tri-n-butylammonium (112 mg; 0.36 mmol) and potassium carbonate (1.244 g; 9.0 mmol), then the mixture was stirred at room temperature for 21 hours. After completion of the reaction, the resulting reaction mixture was adjusted to pH 7, using 10% hydrochloric acid. Chloroform (5 ml) was added to the pH-adjusted mixture, from which the aqueous layer was removed. The resulting organic layer was washed sequentially with aqueous saturated sodium hydrogen carbonate (4 mL) and aqueous saturated sodium chloride (4 mL). After drying over magnesium sulfate, the obtained product was concentrated and purified by silica gel column chromatography (chloroform: methanol=20:1 (V/V)), to give 4'-((4'-methylthiophenyl)methyl)-5'-(trifluoromethyl)-1H-pyrazole-3'-o-(2,3,4,6-o-tetraacetyl)-β-D-glucopyranoside as pale yellow oil (870 mg; 1.41 mmol).

$^1$H-NMR (300 MHz, DMSO-d6) δ: 1.92 (3H, s), 2.03 (3H, s), 2.05 (3H, s), 2.10 (3H, s), 2.45 (3H, s), 3.74 (2H, s), 4.21 (1H, dd, J=2.4, 12.6 Hz), 4.28 (1H, dd, J=4.2, 12.6 Hz), 5.19-5.28 (4H, m), 5.41 (1H, d, J=6.3 Hz), 7.09 (2H, d, J=8.1 Hz), 7.16 (2H, d, J=8.1 Hz). ESI-MS(m/z):619 [ (M+H)$^+$], 617 [ (M−H)$^−$].

Step 2

Synthesis of 4-((4-methylthiophenyl)methyl)-5-(trifluoromethyl)-1H-pyrazole-3-o-β-D-glucopyranoside The pale yellow oil of 4'-((4'-methylthiophenyl)methyl)-5'-(trifluoromethyl)-1H-pyrazole-3'-o-(2,3,4,6-o-tetraacetyl)-β-D-glucopyranoside (804 mg; 1.30 mmol) was dissolved in ethanol (6 mL), followed by dropwise addition of aqueous 50% potassium hydroxide solution (0.8 mL), then the reaction mixture was stirred at room temperature for 10 minutes. After completion of the reaction, the resulting reaction mixture was adjusted to pH 7, using 10% hydrochloric acid, for agitation for 24 hours. The resulting crystal was filtered, followed by washing with ethanol (5 mL). The mother solution was concentrated, to give the oil, which was then purified by silica gel column chromatography (chloroform:methanol=10:1 (V/V)), to give 4-((4-methylthiophenyl)methyl)-5-(trifluoromethyl)-1H-pyrazole-3-o-β-D-glucopyranoside as white crystal (321 mg; 0.71 mmol).

$^1$H-NMR (300 MHz, DMSO-d6) δ: 2.43 (3H, s), 3.15-3.25 (4H, m), 4.39 (1H, dd, J=5.3, 12.0 Hz), 3.67 (1H, d, J=12.0), 3.75 (2H, s), 4.92 (1H, br-s), 5.04 (1H, br-s), 5.12 (1H, br-s), 7.12 (2H, d, J=8.7 Hz), 7.16 (2H, d, J=8.7 Hz). ESI-MS(m/z):449[(M−H)$^-$].

Production Example 2-A

Synthesis of 4-((4-ethylphenyl)methyl)-5-(trifluoromethyl)-1H-pyrazol-3-yl-β-D-glucopyranoside uronic acid Step 1

Synthesis of benzyl 4'-((4'-ethylphenyl)methyl)-5'-(trifluoromethyl)-1H-pyrazol-3'-yl-2,3,4-o-tribenzyl-β-D-glucopyranouronate 2,3,4-Tri-o-benzyl-D-glucopyranoside uronic acid benzyl ester (SIGMA) (199 mg; 0.359 mmol), 1,2-dihydro-4-((4-ethylphenyl)methyl)-5-(trifluoromethyl)-3H-pyrazol-3-one (99 mg; 0.367 mmol) (prepared by the method described in J. Med. Chem 1996, 39, 3920-3928) and triphenylphosphine (109 mg; 0.416 mmol) were dissolved in dry THF (with no content of stabilizers) (0.5 ml). A 40% toluene solution of diethyl azodicarboxylate (0.18 ml; 0.40 mmol) was added to the resulting solution under ice cooling, then the mixture was stirred at room temperature for 1.5 hours. The reaction solution was directly purified by silica gel chromatography (hexane-ethyl acetate:hexane=1:10 to 1:5), followed by concentration under reduced pressure, to give benzyl 4'-((4'-ethylphenyl)methyl)-5'-(trifluoromethyl)-1H-pyrazol-3'-yl-2,3,4-o-tribenzyl-β-D-glucopyranouronate as pale yellow oil (127 mg; 0.157 mmol).

$^1$H-NMR (300 MHz, DMSO-d6) δ: 1.12 (3H, t, J=7.8 Hz), 2.50 (2H, q, J=7.8 Hz), 3.64-3.86 (4H, m), 3.90-4.02 (1H, m), 4.05-4.20 (1H, m), 4.40-4.58 (3H, m), 4.65-4.82 (3H, m), 5.10 (1H, d, J=12.1 Hz), 5.15 (1H, d, J=12.1 Hz), 5.20-5.30 (1H, br), 6.90-7.35 (24H, m).

Step 2

Synthesis of 4-((4-ethylphenyl)methyl)-5-(trifluoromethyl)-1H-pyrazol-3-yl-β-D-glucopyranoside uronic acid Benzyl 4'-((4'-ethylthiophenyl)methyl)-5'-(trifluoromethyl)-1H-pyrazol-3'-yl-2,3,4-o-tribenzyl-β-D-glucopyranouronate (122 mg; 0.151 mmol) was dissolved in ethyl acetate (4 ml) and methanol (4 ml). The mixture was stirred in the presence of 20% palladium hydroxide-carbon (50% wet; Aldrich) (204 mg) under hydrogen atmosphere at atmospheric pressure and at room temperature for 8 hours. The 20% palladium hydroxide-carbon was filtered off using combined solution of dichloromethane and methanol (4:1) (100 ml), then the filtrate was concentrated and dried up under reduced pressure. The resulting solid was suspended in distilled water, purified on a SepPack column (water methanol=1:0 to 0:1), and then dried up under reduced pressure at a bath temperature of 40° C. or less, to give 4-((4-ethylphenyl)methyl)-5-(trifluoromethyl)-1H-pyrazol-3-yl-β-D-glucopyranoside uronic acid as amorphous white solid (22 mg; 0.050 mmol).

$^1$H-NMR (300 MHz, DMSO-d6) δ: 1.19 (3H, t, J=7.5 Hz), 2.58 (2H, q, J=7.5 Hz), 3.35-3.51 (2H, m), 3.52-3.65 (1H, m), 3.70-3.90 (3H, m), 5.00-5.20 (1H, br), 7.06 (2H, d, J=8.4 Hz), 7.09 (2H, d, J=8.4 Hz). ESI-MS(m/z) 445[(M−H)$^+$], 447 [(M+H)$^+$].

Production Example 3-A

Synthesis of 4'-[(4'-ethylphenyl)methyl]-1'-benzyl-5'-trifluoromethyl-1H-pyrazole-3'-o-β-D-glucopyranoside Step 1

Synthesis of 4-[(4-ethylphenyl)methyl]-5-trifluoromethyl-3-o-t-butyldimethylsilyl-1H-pyrazole 1,2-Dihydro-4-[(4-ethylphenyl)methyl]-5-trifluoromethyl-3H-pyrazol-3-one (4.76 g; 17.6 mmol) (prepared by the method described in J. Med. Chem 1996, 39, 3920-3928) and imidazole (1.57 g; 23.1 mmol) were dissolved in dimethylformamide (20 ml). T-Butyldimethylsilyl chloride (2.98 g; 19.8 mmol) was added to the resulting mixture, the mixture was stirred at room temperature for 30 minutes. After the addition of water (100 ml), the mixture was extracted with ethyl acetate and hexane (a mixture solvent at 2:1) three times. The organic phase was washed with water, dried over sodium sulfate and concentrated, to give the desired compound. (6.9 g, 17.9 mmol; quantitative).

$^1$H-NMR (300 MHz, CDCl$_3$) δ: 0.21 (6H, s), 0.93 (9H, s), 1.19 (3H, t, J=7.6 Hz), 2.59 (2H, q, J=7.6 Hz), 3.74 (2H, s), 7.09 (4H, pseudo ABq). ESI-MS(m/z) 269[(M-TBS)$^-$].

Step 2

Synthesis of 4-[(4-ethylphenyl)methyl]-1-benzyl-5-trifluoromethyl-3-o-t-butyldimethylsilyl-1H-pyrazole 4-[(4-Ethylphenyl)methyl]-5-trifluoromethyl-3-o-t-butyldimethylsilyl-1H-pyrazole (0.39 g; 1.0 mmol), triphenylphosphine (0.30 g; 1.1 mmol) and benzyl alcohol (0.14 ml; 1.4 mmol) were dissolved in anhydrous tetrahydrofuran (2.0 ml), then the mixture was stirred at room temperature. A 40% toluene solution of diethyl azodicarboxylate (0.50 ml; 1.1 mmol) was gradually added. Twenty minutes later, the resulting mixture was concentrated, to which hexane (1 ml) was added. The deposited precipitate was filtered off, followed by concentration. By purification on a silica gel column chromatography (hexane→5% ethyl acetate/hexane), the desired compound was obtained. (0.40 g, 0.83 mmol) (83%).

¹H-NMR (300 MHz, CDCl₃) δ: 0.22 (6H, s), 0.92 (9H, s), 1.20 (3H, t, J=7.5 Hz), 2.59 (2H, q, J=7.5 Hz), 3.74 (2H, s), 5.19 (2H, s), 7.06 (4H, pseudo ABq), 7.11-7.33 (5H, m).

Step 3

Synthesis of 4-[(4-ethylphenyl)methyl]-1-benzyl-5-trifluoromethyl-1H-pyrazole

4-[(4-Ethylphenyl)methyl]-1-benzyl-5-trifluoromethyl-3-o-t-butyldimethylsilyl-1H-pyrazole (0.40 g; 0.83 mmol) was dissolved in tetrahydrofuran (2 ml) and methanol (0.5 ml), to which aqueous 1 M HCl solution (1 ml) was added, then the mixture was stirred at room temperature for 7 hours. Water (5 ml) was added, for extraction three times with 5 ml of ethyl acetate. After drying over anhydrous sodium sulfate and concentration, purification on a silica gel column (hexane→10% ethyl acetate/hexane) was done to obtain the objective compound (0.27 g; 0.74 mmol). (89%)

¹H-NMR (300 MHz, CDCl₃) δ: 1.21 (3H, t, J=7.6 Hz), 2.61 (2H, q, J=7.6 Hz), 3.77 (2H, s), 5.18 (2H, s), 7.07-7.31 (9H, m). ESI-MS(m/z) [361 (M+H)⁺], [359 (M−H)⁻].

Step 4

Synthesis of 4'-[(4-ethylphenyl)methyl]-1'-benzyl-5'-trifluoromethyl-1H-pyrazole-3'-o-(2,3,4,6-tetraacetyl)-β-D-glucopyranoside Water (1 mL) and chloroform (10 mL) were added to 4-[(4-ethylphenyl)methyl]-1-benzyl-5-trifluoromethyl-1H-pyrazole (0.22 g; 0.62 mmol), 2,3,4,6-o-tetraacetyl-α-D-glucopyranosyl bromide (0.39 g; 0.94 mmol), benzyl chloride tri-n-butylammonium (0.055 g; 0.18 mmol) and potassium carbonate (0.79 g; 5.7 mmol), the mixture was stirred at room temperature for overnight. About 0.1 g of benzyl chloride tri-n-butylammonium was further added, then the mixture was stirred for overnight. The organic layer was purified by silica gel column chromatography (ethyl acetate:hexane 10:1), to give 0.39 g of a crude product mainly containing the objective compound, which was then used for the following reaction.

¹H-NMR (300 MHz, CDCl₃) δ: 1.19 (3H, t, J=7.6 Hz), 1.86 (3H, s), 2.015 (3H, s), 2.019 (3H, s), 2.03 (3H, s), 2.58 (2H, q, J=7.6 Hz), 3.74 (2H, s), 3.81 (1H, ddd, J=9.5, 4.2, 2.3 Hz), 4.08 (1H, dd, J=12.5, 2.3 Hz), 4.27 (1H, dd, J=12.5, 4.2 Hz), 5.16-5.28 (3H, m), 5.24 (2H, s), 5.58-5.63 (1H, m), 7.05 (4H, s), 7.16-7.35 (5H, m). ESI-MS(m/z) [691 (M+H)⁺].

Step 5

Synthesis of 4-[(4-ethylphenyl)methyl]-1-benzyl-5-trifluoromethyl-1H-pyrazole-3-o-β-D-glucopyranoside A crude product (0.28 g) of 4'-[(4'-ethylphenyl)methyl]-1'-benzyl-5'-trifluoromethyl-1H-pyrazole-3'-o-(2,3,4,6-tetraacetyl)-β-D-glucopyranoside was dissolved in ethanol (5 ml), followed by addition of 5 ml of aqueous 4N NaOH solution, then the mixture was stirred at room temperature. One hour later, water (50 ml) was added, and the mixture was extracted five times with 5 ml of ethyl acetate. After concentration, the extract was purified on a silica gel column chromatography (dichloromethane→+10% methanol/dichloromethane) to give the desired compound. (0.11 g, 0.21 mmol).

¹H-NMR (300 MHz, CD3OD) δ: 1.19 (3H, t, J=7.6 Hz), 2.58 (2H, q, J=7.6 Hz), 3.34-3.46 (4H, m), 3.68 (1H, dd, J=12.0, 4.7 Hz), 3.81 (1H, dd, J=12.0, 2.1 Hz), 3.83 (2H, s), 5.32 (2H, s), 5.34-5.37 (1H, m), 7.07 (4H, s), 7.10-7.12 (2H, m), 7.25-7.33 (3H, m).

Production Example 4-A

Synthesis of 4'-[(4'-ethylphenyl)methyl]-1'-benzyl-5'-trifluoromethyl-1H-pyrazole-3'-o-(6-carbomethoxy)-β-D-glucopyranoside 4'-[ (4'-Ethylphenyl)methyl]-1'-benzyl-5'-trifluoromethyl-1H-pyrazole-3'-o-β-D-glucopyranoside (0.11 g; 0.21 mmol) was dissolved in pyridine (1.5 ml) and cooled in an ice bath. Methyl chlorocarbonate (0.020 ml; 0.26 mmol) was added to the resulting mixture, which was then back to ambient temperature over 0.5 hour. 2 hours and 19 hours later, individually, methyl chlorocarbonate (0.020 ml; 0.26 mmol) was added, and the mixture was stirred at room temperature for 6 hours. Ethyl acetate (5 ml), aqueous 1M HCl solution (10 ml) and water (20 ml) were added, and the mixture was extracted with ethyl acetate. After drying and concentration, the residue was purified on a silica gel column chromatography (ethyl acetate) to give the desired compound. (0.059 g, 0.10 mmol). (47%)

¹H-NMR (300 MHz, CDCl3) δ: 1.18 (3H, t, J=7.6 Hz), 2.57 (2H, q, J=7.6 Hz), 3.48-3.60 (4H, m), 3.70 (3H, s), 3.74 (1H, d, J=15.8 Hz), 3.82 (1H, d, J=15.8 Hz), 4.34 (2H, s), 5.22 (1H, d, J=4.4 Hz), 5.23 (2H, s), 7.07 (4H, s), 7.12 (2H, d, J=6.4 Hz), 7.21-7.32 (3H, m). ESI-MS(m/z) [581 (M+H)⁺], [579 (M−H)⁻].

Production Example 5-A

Synthesis of 4-[(4-ethylphenyl)methyl]-1-[(4-methoxyphenyl)methyl]-5-trifluoromethyl-1H-pyrazole-3-o-β-D-glucopyranoside Step 1

Synthesis of 4-((4-ethylphenyl)methyl)-1-[(4-methoxyphenyl)methyl]-5-trifluoromethyl-3-o-t-butyldimethylsilyl-1H-pyrazole The objective compound was obtained in the same manner as in the Step 2 of the Production Example 3-A except for the use of 4-methoxybenzyl bromide instead of benzyl bromide.

¹H-NMR (300 MHz, CDCl₃) δ: 0.22 (6H, s), 0.93 (9H, s), 1.19 (3H, t, J=7.6 Hz), 2.58 (2H, q, J=0.6 Hz), 3.72 (2H, s), 3.78 (3H, s), 5.14 (2H, s), 6.83 (2H, d, J=8.8 Hz), 7.07 (4H, pseudo ABq), 7.16 (2H, d, J=8.8 Hz).

Step 2

Synthesis of 4-[(4-ethylphenyl)methyl]-1-[(4-methoxyphenyl)methyl]-5-(trifluoromethyl)-1H-pyrazole The objective compound was obtained from 4-[(4-ethylphenyl)methyl]-1-[(4-methoxyphenyl)methyl]-5-(trifluoromethyl)-3-o-t-butyldimethylsilyl-1H-pyrazole in the same manner as in the Step 3 of the Production Example 3-A. (82%)

¹H-NMR (300 MHz, CDCl₃) δ: 1.21 (3H, t, J=7.5 Hz), 2.60 (2H, q, J=7.5 Hz), 3.77 (5H, s), 5.10 (2H, s), 6.81-6.84 (2H, m), 7.07-7.19 (6H, m). ESI-MS(m/z) [391 (M+H)⁺], [389 (M−H)⁻].

Step 3

Synthesis of 4'-[(4'-ethylphenyl)methyl]-1'-[(4-methoxyphenyl)methyl]-5'-(trifluoromethyl)-1H-pyrazole-3'-o-(2,3,4,6-tetraacetyl)-β-D-glucopyranoside A crude product of the objective compound was obtained from 4-[(4-ethylphenyl)methyl]-1-[(4-methoxyphenyl)methyl]-5-(trifluoromethyl)-1H-pyrazole in the same manner as in the Step 4 of the Production Example 3-A.

$^1$H-NMR (300 MHz, CDCl$_3$) δ: 1.19 (3H, t, J=7.6 Hz), 1.86 (3H, s), 2.07 (3H, s), 2.11 (6H, s), 2.58 (2H, q, J=7.6 Hz), 3.73 (2H, s), 3.75-3.84 (1H, m), 4.24-4.30 (1H, m), 5.16 (2H, s), 5.19-5.28 (3H, m), 5.56-5.60 (1H, m), 6.75 (2H, d, J=8.8 Hz), 7.05 (4H, s), 7.15 (2H, d, J=8.8 Hz). ESI-MS(m/z) [721 (M+H)$^+$]

Step 4

Synthesis of 4-[(4-ethylphenyl)methyl]-1-[(4-ethoxyphenyl)methyl]-5-trifluoromethyl-1H-pyrazole-3-o-β-D-glucopyranoside The objective compound was obtained from 4'-[(4'-ethylphenyl)methyl]-1'-[(4-methoxyphenyl)methyl]-5'-trifluoromethyl-1H-pyrazole-3'-o-(2,3,4,6-tetraacetyl)-β-D-glucopyranoside in the same manner as in the Step 5 of the Production Example 3-A. (91% in 2 steps).

$^1$H-NMR (300 MHz, CD3OD) δ: 1.19 (3H, t, J=7.6 Hz), 2.57 (2H, q, J=7.6 Hz), 3.36-3.44 (4H, m), 3.66-3.82 (2H, m), 3.76 (3H, s), 3.82 (2H, s), 5.24 (2H, s), 5.33-5.36 (1H, m), 6.86 (2H, d, J=8.5 Hz), 7.07 (4H, s), 7.12 (2H, d, J=8.5 Hz). ESI-MS(m/z) [553 (M+H)$^+$], [551 (M–H)$^-$].

Production Example 6-A

Synthesis of 4'-[(4'-ethylphenyl)methyl]-1'-[(4'-methoxyphenyl)methyl]-5'-trifluoromethyl-1H-pyrazole-3'-o-(6-carbomethoxy)-β-D-glucopyranoside 4-[(4-Ethylphenyl)methyl]-1-[(4-methoxyphenyl)methyl]-5-trifluoromethyl-1H-pyrazole-3-o-β-D-glucopyranoside (0.18 g; 0.32 mmol) was dissolved in 2,4,6-collidine (2 ml) and cooled to –50° C. Methyl chlorocarbonate (0.035 ml; 0.45 mmol) was added to the resulting mixture, which was then back to room temperature over one hour. 27 hours later, ethyl acetate (20 ml) and aqueous 1M HCl solution (20 ml) were added, then the mixture was extracted with ethyl acetate. After drying and concentration, the residue was purified n on a silica gel column chromatography (hexane→ethyl acetate) to give the desired compound. (0.12 g, 0.20 mmol). (62%)

$^1$H-NMR (300 MHz, CDCl$_3$) δ: 1.21 (3H, t, J=7.6 Hz), 2.26 (1H, d, J=2.3 Hz), 2.61 (2H, q, J=7.6 Hz), 2.69 (1H, s), 2.86 (1H, s), 3.45-3.61 (4H, m), 3.73 (1H, d, J=15.2 Hz), 3.80 (3H, s), 3.80 (3H, s), 3.88 (1H, d, J=15.2 Hz), 4.37 (1H, d, J=12.3 Hz), 4.49 (1H, dd, J=12.3, 3.0 Hz), 5.19 (2H, s), 5.20 (1H, d, J=7.6 Hz), 6.86 (2H, d, J=8.5 Hz), 7.10 (4H, s), 7.16 (2H, d, J=8.5 Hz).

Production Example 7-A

Synthesis of 4-[(4-ethylphenyl)methyl]-1-phenyl-5-trifluoromethyl-1H-pyrazole-3-o-β-D-glucopyranoside Step 1

Synthesis of 4-[(4-ethylphenyl)methyl]-1-phenyl-5-trifluoromethyl-3-o-t-butyldimethylsilyl-1H-pyrazole 4-[(4-Ethylphenyl)methyl]-5-trifluoromethyl-3-o-t-butyldimethylsilyl-1H-pyrazole (0.079 g; 0.21 mmol), phenyl-boronic acid (0.049 g; 0.40 mmol), and anhydrous copper (II) acetate (0.057 g; 0.32 mmol) were dissolved in dry dichloromethane (5 ml), followed by addition of Molecular Sieves 4A powder (0.15 g) and pyridine (0.032 ml; 0.40 mmol), then the mixture was stirred at room temperature for overnight. The reaction solution was purified on a silica gel column chromatography (hexane→hexane:dichloromethane 5:1 to 3:1) to give the desired compound. (0.074 g; 0.16 mmol). (80%)

$^1$H-NMR (300 MHz, CDCl$_3$) δ: 0.27 (6H, s), 0.96 (9H, s), 1.21 (3H, t, J=7.6 Hz), 2.61 (2H, q, J=7.6 Hz), 3.84 (2H, s), 7.11 (2H, J=8.3 Hz), 7.18 (2H, J=8.3 Hz), 7.35-7.45 (5H, m). ESI-MS(m/z) [461 (M+H)$^+$], [459 (M–H)$^-$].

Step 2

Synthesis of 4-[(4-ethylphenyl)methyl]-1-phenyl-5-trifluoromethyl-1H-pyrazole

The objective compound was obtained using 4-[(4-ethylphenyl)methyl]-1-phenyl-5-(trifluoromethyl)-3-o-t-butyldimethylsilyl-1H-pyrazole in the same manner as in the Step 3 of the Production Example 3-A. (95%)

$^1$H-NMR (300 MHz, CDCl$_3$) δ: 1.22 (3H, t, J=7.6 Hz), 2.62 (2H, q, J=7.6 Hz), 3.81 (2H, s), 7.10 (2H, d, J=8.1 Hz), 7.17 (2H, d, J=8.1 Hz), 7.35-7.50 (5H, m), 10.40-10.80 (1H, br-s). ESI-MS(m/z) [347 (M+H)$^+$], [345 (M–H)$^-$].

Step 3

Synthesis of 4'-[(4'-ethylphenyl) methyl]-1'-phenyl-5'-trifluoromethyl-1H-pyrazole-3'-o-(2,3,4,6-tetraacetyl)-β-D-glucopyranoside A crude product of the objective compound was obtained using 4-[(4-ethylphenyl)methyl]-1-phenyl-5-trifluoromethyl-1H-pyrazole in the same manner as in the Step 4 of the Production Example 3-A.

$^1$H-NMR (300 MHz, CDCl$_3$) δ: 1.21 (3H, t, J=7.6 Hz), 1.90 (3H, s), 2.02 (3H, s), 2.03 (3H, s), 2.04 (3H, s), 2.61 (2H, q, J=7.6 Hz), 3.80-3.90 (2H, s and 1H, m), 4.10-4.30 (2H, m), 5.15-5.36 (3H, m), 5.68 (1H, d, J=7.5 Hz), 7.10 (2H, d, J=8.3 Hz), 7.15 (2H, d, J=8.3 Hz), 7.38-7.47 (5H, m). ESI-MS(m/z) [677 (M+H)$^+$].

Step 4

Synthesis of 4-[(4-ethylphenyl)methyl]-1-phenyl-5-trifluoromethyl-1H-pyrazole-3-o-β-D-glucopyranoside The objective compound was obtained using a crude product of 4'-[(4'-ethylphenyl)methyl]-1'-phenyl-5'-trifluoromethyl-1H-pyrazole-3'-o-(2,3,4,6-tetraacetyl)-β-D-glucopyranoside in the same manner as in the Step 5 of the Production Example 3-A. (84% in 2 steps)

$^1$H-NMR (300 MHz, DMSO-d$_6$) δ: 1.19 (3H, t, J=7.6 Hz), 2.60 (2H, q, J=7.6 Hz), 3.15-3.35 (4H, m), 3.45-3.55 (1H, m), 3.69 (1H, dd, J=11.4, 5.7 Hz), 3.85 (1H, d, J=15.6 Hz), 3.92 (1H, d, J=15.6 Hz), 4.55 (1H, t, J=5.7 Hz), 5.03 (1H, d, J=4.5 Hz), 5.13 (1H, d, J=3.9 Hz), 5.35 (1H, d, J=7.5 Hz), 5.41 (1H, d, J=4.5 Hz), 7.17 (2H, d, J=8.3 Hz), 7.22 (2H, d, J=8.3 Hz), 7.47-7.62 (5H, m). ESI-MS(m/z) [509 (M+H)$^+$], [507 (M–H)$^-$].

Production Example 8-A

Synthesis of 4'-[(4'-ethylphenyl)methyl]-1'-phenyl-5'-trifluoromethyl-1H-pyrazole-3'-o-(6-carbomethoxy)-β-D-glucopyranoside The objective compound was obtained, using 4-[(4-ethylphenyl)methyl]-1-phenyl-5-trifluoromethyl-1H-pyrazole-3-o-β-D-glucopyranoside in the same manner as in the Production Example 4-A. (71%).

$^1$H-NMR (300 MHz, CDCl$_3$) δ: 1.22 (3H, t, J=7.6 Hz), 2.18 (1H, br), 2.62 (2H, q, J=7.6 Hz), 2.72 (1H, br), 2.89 (1H, br), 3.45-3.63 (4H, m), 3.78 (3H, s), 3.81 (1H, d, J=15.6 Hz), 3.98 (1H, d, J=15.6 Hz), 4.37 (1H, dd, 12.0, 1.7 Hz), 4.49 (1H, dd, 12.0, 3.6 Hz), 5.32 (1H, d, J=7.2 Hz), 7.14 (2H, d, J=8.3 Hz), 7.19 (2H, d, J=8.3 Hz), 7.39-7.47 (5H, m). ESI-MS(m/z) [567 (M+H)$^+$], [565 (M−H)$^-$].

Production Example 9-A

Synthesis of 4-[(3-fluoro-4-methoxyphenyl)methyl]-1-isopropyl-5-methyl-1H-pyrazole-3-o-β-D-glucopyranoside

Step 1

Synthesis of ethyl 2-[(3-fluoro-4-methoxy)benzyl]-3-oxobutylate

Ethyl acetoacetate (1.69 g; 13.0 mmol) and sodium iodide (9.6 g; 65 mmol) were dissolved in 100 ml of acetonitrile. The resulting solution was cooled to 0° C. Then, trimethylsilyl chloride (8.2 ml; 65 mmol) was gradually added. 10 minutes later, 3-fluoro-4-methoxybenzaldehyde (2.0 g; 13.0 mmol) was added in three portions. 10 minutes later, the resulting mixture was back to room temperature and continuously stirred. 6 hours later, the mixture was transferred into a bath at 60° C., for overnight stirring. The reaction solution was cooled, to which water (250 ml), ethyl acetate (250 ml) and aqueous saturated sodium chloride (50 ml) were then added. The ethyl acetate layer was extracted, using a separation funnel. The resulting organic layer was washed with aqueous saturated sodium sulfite and dried over anhydrous magnesium sulfate. After concentration, the dried product was purified by silica gel column chromatography (EtOAc:-Hex; 1:4), to give the desired compound (2.54 g; 9.5 mmol). (73%.)

$^1$H-NMR (300 MHz, CDCl$_3$) δ: 6.82-6.96 (3H, m), 4.12-4.20 (2H, m), 3.86 (3H, s), 3.71 (1H, t, J=7.8), 3.08 (2H, d, J=8.1), 2.20 (3H, s), 1.23 (3H, t, J=7.2).

Step 2

Synthesis of 1,2-dihydro-4-[(3-fluoro-4-methoxyphenyl)methyl]-5-methyl-3H-pyrazol-3-one Ethyl 2-[(3-fluoro-4-methoxy)benzyl]-3-oxobutylate (2.54 g; 9.5 mmol) was dissolved in toluene (50 ml), followed by addition of hydrous hydrazine (0.72 g; 14.2 mmol), then the mixture was stirred 100° C. for overnight. The reaction solution was cooled, and the crystals were filtered. Obtained crystals were dried with a vacuum pump, to give the desired compound (1.86 g; 7.9 mmol). (83%).

$^1$H-NMR (300 MHz, DMSO-d6) δ: 7.00 (1H, t, J=8.4), 6.86-6.94 (2H, m), 3.75 (3H, s), 3.46 (2H, s), 1.98 (3H, s). ESI-MS(m/z):237[(M+H)$^+$], 235[(M−H)$^-$].

Step 3

Synthesis of 4'-[(3'-fluoro-4'-methoxyphenyl)methyl]-5'-methyl-1H-pyrazole-3'-o-(2,3,4,6-tetrabenzyl)-β-D-glucopyranoside 2,3,4,6-Tetra-o-benzyl-D-glucopyranoside (2.3 g; 4.2 mmol), 1,2-dihydro-4-[(3-fluoro-4-methoxyphenyl)methyl]-5-methyl-3H-pyrazol-3-one (1.0 g; 4.2 mmol) and triphenylphosphine (1.1 mg; 4.2 mmol) were dissolved in dry THF (with no content of stabilizers) (40 ml). A 40% toluene solution of diethyl azodicarboxylate (1.9 ml; 4.2 mmol) was added to the resulting solution under ice cooling, then the mixture was stirred at room temperature for overnight. After the reaction solution was concentrated, the concentrate was directly purified by silica gel chromatography (hexane-ethyl acetate:hexane=2:3), followed by concentration under reduced pressure, to give the desired compound (2.2 g; 2.9 mmol). (70%).

$^1$H-NMR (300 MHz, CDCl$_3$) δ: 7.10-7.32 (20H, m), 6.78-6.92 (2H, m), 6.67 (1H, t, J=8.1), 5.51 (1H, d, J=7.5), 4.46-4.92 (10H, m), 3.60-3.76 (6H, m), 3.71 (3H, s), 2.07 (3H, s). ESI-MS(m/z):759[(M+H)$^+$], 757[(M−H)$^-$].

Step 4

Synthesis of 4'-[(3'-fluoro-4'-methoxyphenyl)methyl]-1'-isopropyl-5'-methyl-1H-pyrazole-3'-o-(2,3,4,6-tetrabenzyl)-β-D-glucopyranoside 4'-[ (3'-Fluoro-4'-methoxyphenyl)methyl]-5'-methyl-1H-pyrazole-3'-o-(2,3,4,6-tetrabenzyl)-β-D-glucopyranoside (2.2 g; 2.9 mmol) was dissolved in dimethylformamide (44 ml), followed by addition of cesium carbonate (9.6 g; 29.5 mmol) and isopropyl iodide (2.5 g; 14.8 mmol), then the mixture was stirred at room temperature for overnight.

Water (200 ml), aqueous saturated sodium chloride (50 ml) and dichloromethane (300 ml) were added. The organic layer was extracted with a separation funnel. The extract was dried over anhydrous sodium sulfate and concentrated. The concentrate was purified by silica gel chromatography (hexane-ethyl acetate:hexane=1:3), followed by concentration under reduced pressure, to give the desired compound (1.7 g; 2.2 mmol). (74%).

$^1$H-NMR (300 MHz, CDCl$_3$) δ: 7.12-7.32 (20H, m), 6.80-6.92 (2H, m), 6.68 (1H, t, J=8.4), 5.47 (1H, d, J=7.2), 4.74-4.94 (5H, m), 4.44-4.64 (5H, m), 4.24-4.32 (1H, m), 3.73 (3H, s), 3.60-3.72 (6H, m), 2.06 (3H, s), 1.38 (3H, t, J=7.5). ESI-MS(m/z):801[(M+H)$^+$].

Step 5

Synthesis of 4-[(3-fluoro-4-methoxyphenyl)methyl]-1-isopropyl-5-methyl-1H-pyrazole-3-o-β-D-glucopyranoside 4'-[ (3'-Fluoro-4'-methoxyphenyl) methyl]-1'-isopropyl-5'-methyl-1H-pyrazole-3'-o-(2,3,4,6-tetrabenzyl)-β-D-glucopyranoside (1.7 g; 2.2 mmol) was dissolved in ethanol (70 ml), followed by addition of 20% palladium hydroxide-carbon (1.0 g). Under hydrogen atmosphere, the resulting mixture was stirred for 2 hours. The reaction solution was filtered through a filter cell, to give the filtrate, which was then concentrated and purified by silica gel chromatography (15% methanol:dichloromethane). Subsequently, the purified product was again concentrated under reduced pressure, to give the desired compound (828 mg; 1.9 mmol). (88%).

¹H-NMR (300 MHz, DMSO-d6) δ: 6.92-7.04 (3H, m), 5.20 (1H, d, J=4.5), 5.11 (1H, d, J=7.2), 5.02 (1H, d, J=3.6), 4.93 (1H, d, J=4.5), 4.41 (1H, t, J=5.7), 4.28-4.40 (1H, m), 3.77 (3H, s), 3.56-3.66 (1H, m), 3.42-3.52 (1H, m), 3.08-3.24 (4H, m), 2.07 (3H, s), 1.24-1.30 (3H, m). ESI-MS(m/z):[441 (M+H)⁺].

Production Example 10-A

Synthesis of 4'-[(3'-fluoro-4'-methoxyphenyl)methyl]-1'-isopropyl-5'-methyl-1H-pyrazole-3'-o-(6-carbomethoxy)-β-D-glucopyranoside 4-[(3-Fluoro-4-methoxyphenyl)methyl]-1-isopropyl-5-methyl-1H-pyrazole-3-o-β-D-glucopyranoside (820 mg; 1.9 mmol) was dissolved in collidine (8 ml) and cooled to 0° C. 10 minutes later, methyl chlorocarbonate (0.22 ml) was added, then the mixture was stirred for 7 hours. The resulting mixture was neutralized with 2N HCl, then the mixture was extracted with ethyl acetate. The organic layer was dried over anhydrous sodium sulfate. After concentration, the residue was purified by silica gel chromatography (ethyl acetate). The resulting solution was concentrated under reduced pressure, to give the desired compound (303 mg; 0.61 mmol). (33%).
¹H-NMR (300 MHz, CDCl₃) δ: 6.80-6.92 (3H, m), 5.02 (1H, d, J=8.1), 4.40 (2H, s), 4.22-4.34 (1H, m), 3.85 (3H, s), 3.78 (3H, s), 3.44-3.66 (6H, m), 2.08 (3H, s), 1.38 (6H, d, J=6.6). ESI-MS(m/z):[499(M+H)⁺].

Production Example 11-A

Synthesis of 4-[(2-fluoro-4-methoxyphenyl)methyl]-1-isopropyl-5-methyl-1H-pyrazole-3-o-β-D-glucopyranoside Step 1

Synthesis of ethyl 2-[(2-fluoro-4-methoxy)benzyl]-3-oxobutylate

The objective compound (3.4 g; 12.7 mmol) was obtained, using 2-fluoro-4-methoxybenzaldehyde (3.0 g) in the same manner as in the Step 1 of Production Example 9. Yield 65%.
¹H-NMR (300 MHz, CDCl₃) δ: 7.07 (1H, t, J=8.7), 6.40-6.62 (2H, m), 4.10-4.20 (2H, m), 3.79 (1H, t, J=7.8), 3.77 (3H, s), 3.04-3.18 (2H, m), 2.21 (3H, s), 1.21 (3H, t, J=7.2).

Step 2

Synthesis of 1,2-dihydro-4-[(2-fluoro-4-methoxyphenyl)methyl]-5-methyl-3H-pyrazol-3-one The objective compound (2.46 g; 10.4 mmol) was obtained, using ethyl 2-[(2-fluoro-4-methoxy)benzyl]-3-oxobutylate (3.4 g) in the same manner as in the Step 2 of Production Example 9-A. Yield 83%.
¹H-NMR (300 MHz, CDCl₃) δ: 7.02 (1H, t, J=8.7), 6.72 (1H, dd, J=2.4, 12.0), 6.66 (1H, d, J=2.7, 8.4), 3.71 (3H, s) 3.47 (2H, s), 1.99 (3H, s). ESI-MS(m/z):237[(M+H)⁺], 235 [(M−H)⁻].

Step 3

Synthesis of 4'-[(2'-fluoro-4'-methoxyphenyl)methyl]-5'-methyl-1H-pyrazole-3'-o-(2,3,4,6-tetrabenzyl)-β-D-glucopyranoside The objective compound (2.6 g; 3.46 mmol) was obtained, using 1,2-dihydro-4-[(2-fluoro-4-methoxyphenyl)methyl]-5-methyl-3H-pyrazol-3-one (1.0 g; 4.2 mmol) in the same manner as in the Step 3 of Production Example 9-A. Yield 82%.
¹H-NMR (300 MHz, DMSO-d6) δ: 7.12-7.32 (20H, m), 6.99 (1H, t, J=9.0), 6.50 (1H, dd, J=2.4, 11.7), 6.42 (1H, dd, J=2.7, 8.4), 5.54 (1H, d, J=7.2), 4.44-4.92 (8H, m), 3.60-3.76 (8H, m), 3.62 (3H, s), 2.09 (3H, s). ESI-MS(m/z):759[(M+H)⁺], 757 [ (M−H)⁻].

Step 4

Synthesis of 4'-[(2'-fluoro-4'-methoxyphenyl)methyl]-1'-isopropyl-5'-methyl-1H-pyrazole-3'-o-(2,3,4,6-tetrabenzyl)-β-D-glucopyranoside The objective compound (157 mg; 0.19 mmol) was obtained, using 4'-[(2'-fluoro-4'-methoxyphenyl)methyl]-5'-methyl-1H-pyrazole-3'-o-(2,3,4,6-tetrabenzyl)-β-D-glucopyranoside (212 mg; 0.28 mmol) in the same manner as in the Step 4 of Production Example 9-A. Yield 70%.
¹H-NMR (300 MHz, CDCl₃) δ: 7.14-7.30 (20H, m), 6.99 (1H, t, J=8.7), 6.49 (1H, dd, J=2.4, 11.7), 6.41 (1H, dd, J=2.4, 8.7), 5.50 (1H, d, J=7.5), 4.74-4.96 (5H, m), 4.46-4.66 (5H, m), 4.22-4.32 (1H, m), 3.64 (3H, s), 3.60-3.74 (6H, m), 2.08 (3H, s), 1.37 (6H, t, J=6.6). ESI-MS(m/z):801[(M+H)⁺].

Step 5

Synthesis of 4-[(2-fluoro-4-methoxyphenyl)methyl]-1-isopropyl-5'-methyl-1H-pyrazole-3-o-β-D-glucopyranoside The objective compound (80 mg; 0.18 mmol) was obtained, using 4'-[(2'-fluoro-4'-methoxyphenyl)methyl]-1'-isopropyl-5'-methyl-1H-pyrazole-3'-o-(2,3,4,6-tetrabenzyl)-β-D-glucopyranoside (150 mg; 0.19 mmol) in the same manner as in the Step 5 of Production Example 9-A. Yield 97%.
¹H-NMR (300 MHz, DMSO-d6) δ: 7.09 (1H, t, J=9.0), 6.73 (1H, dd, J=2.7, 12.3), 6.66 (1H, dd, J=2.7, 8.7), 5.18 (1H, d, J=4.8), 5.11 (1H, d, J=7.5), 5.01 (1H, d, J=4.2), 4.91 (1H, d, J=4.2), 4.42 (1H, t, J=6.0), 4.30-4.38 (1H, m), 3.72 (3H, s), 3.53 (2H, s), 3.42-3.66 (2H, m), 3.06-3.24 (4H, m), 2.07 (3H, s), 1.28 (3H, d, J=2.7), 1.26 (3H, d, J=2.7). ESI-MS(m/z):441 [(M+H)⁺], 439 [(M−H)⁻].

Production Example 12-A

Synthesis of 4'-[(2'-fluoro-4'-methoxyphenyl)methyl]-1'-isopropyl-5'-methyl-1H-pyrazole-3'-o-(6-carbomethoxy)-β-D-glucopyranoside The objective compound (380 mg; 0.76 mmol) was obtained, using 4-[(2-fluoro-4-methoxyphenyl)methyl]-1-isopropyl-5-methyl-1H-pyrazole-3-o-β-D-glucopyranoside (1.1 g; 2.42 mmol). Yield 31%.
¹H-NMR (300 MHz, CDCl₃) δ: 7.08 (1H, t, J=8.4), 6.52-6.62 (2H, m), 5.02 (1H, d, J=7.8), 4.64 (1H, brs), 4.40 (2H, d, J=2.4), 4.24-4.33 (1H, m), 3.77 (3H, s), 3.75 (3H, s), 3.59 (3H, s), 3.10-3.66 (6H, m), 1.38 (3H, s), 1.35 (3H, s).

Production Example 13-A

Synthesis of 4-[(3-fluoro-4-methylphenyl)methyl]-1-isopropyl-5-methyl-1H-pyrazole-3-o-β-D-glucopyranoside

Step 1

Synthesis of ethyl 2-[(3-fluoro-4-methyl)benzyl]-3-oxobutylate

The objective compound (4.5 g; 17.9 mmol) was obtained, using 3-fluoro-4-methylbenzaldehyde (3.0 g; 21.7 mmol) in the same manner as in the Step 1 of Production Example 9-A. Yield 82%.

$^1$H-NMR (300 MHz, CDCl$_3$) δ: 7.06 (1H, t, J=8.1), 6.78-6.88 (2H, m), 4.15 (2H, q, J=6.9), 3.73 (1H, t, J=7.8), 3.10 (1H, d, J=7.8), 2.22 (3H, s), 2.19 (3H, s), 1.22 (3H, t, J=6.9).

Step 2

Synthesis of 1,2-dihydro-4-[(3-fluoro-4-methylphenyl)methyl]-5-methyl-3H-pyrazol-3-one The objective compound (2.3 g; 10.5 mmol) was obtained, using ethyl 2-[(3-fluoro-4-methyl)benzyl]-3-oxobutylate (2.84 g; 11.3 mmol) in the same manner as in the Step 2 of Production Example 9-A. Yield 93%.

$^1$H-NMR (300 MHz, DMSO-d6) δ: 7.11 (1H, d, J=8.4), 6.81-6.89 (2H, m), 3.49 (2H, s), 2.13 (3H, s), 1.98 (3H, s). ESI-MS(m/z):221[(M+H)$^+$]

Step 3

Synthesis of 4'-[(3'-fluoro-4'-methylphenyl)methyl]-5'-methyl-1H-pyrazole-3'-o-(2,3,4,6-tetraacetyl)-β-D-glucopyranoside 2,3,4,6-o-Tetraacetyl-α-D-glucopyranosyl bromide (2.1 g; 5.0 mmol), 1,2-dihydro-4-[(3-fluoro-4-methylphenyl)methyl]-5-methyl-3H-pyrazol-3-one (1.1 g; 5.0 mmol) and silver carbonate (1.38 g; 5 mmol) were dissolved in dry THF (with no content of stabilizers) (50 ml), then the mixture was stirred overnight at 65° C. in darkness. The reaction solution was filtered through a filter cell, followed by addition of dichloromethane and washing with water. The organic layer was dried over anhydrous sodium sulfate and concentrated, and purified by silica gel chromatography (hexane-ethyl acetate:hexane=1:3). The resulting purified product was concentrated under reduced pressure, to give the desired compound (1.1 g; 2.0 mmol). (40%).

$^1$H-NMR (300 MHz, CDCl$_3$) δ: 7.03 (1H, t, J=7.5), 6.82 (1H, dd, J=1.2, 7.8), 6.74 (1H, dd, J=1.5, 10.8), 5.59 (1H, d, J=8.1), 5.16-5.30 (3H, m), 4.31 (1H, dd, J=3.9, 12.3), 4.12 (1H, dd, J=2.1, 12.3), 3.82-3.88 (1H, m), 3.63 (1H, d, J=15.9), 3.54 (1H, d, J=15.9), 2.20 (3H, d, J=1.5), 2.11 (3H, s), 2.06 (3H, s), 2.03 (3H, s), 2.02 (3H, s), 1.91 (3H, s). ESI-MS(m/z):551[(M+H)$^+$], 549[(M−H)$^-$].

Step 4

Synthesis of 4'-[(3'-fluoro-4'-methylphenyl)methyl]-1'-isopropyl-5'-methyl-1H-pyrazole-3'-o-(2,3,4,6-tetraacetyl)-β-D-glucopyranoside 4'-[(3'-Fluoro-4'-methylphenyl)methyl]-5'-methyl-1H-pyrazole-3'-o-(2,3,4,6-tetraacetyl)-β-D-glucopyranoside (290 mg; 0.53 mmol) was dissolved in dimethylformamide (6 ml), followed by addition of cesium carbonate (1.7 g; 5.2 mmol) and isopropyl iodide (447 mg; 2.6 mmol), then the mixture was stirred overnight at room temperature.

Water, aqueous saturated sodium chloride and dichloromethane were added, then the mixture was extracted, with a separation funnel. The organic layer was dried over anhydrous sodium sulfate and concentrated. After purification by silica gel chromatography (hexane-ethyl acetate:hexane=1:3), the resulting purified product was concentrated under reduced pressure, to give the desired compound (165 mg; 0.28 mmol). (53%).

$^1$H-NMR (300 MHz, CDCl$_3$) δ: 7.02 (1H, t, J=7.8), 6.82 (1H, d, J=7.8), 6.74 (1H, d, J=10.8), 5.79 (1H, d, J=8.1), 5.12-5.34 (3H, m), 4.18-4.32 (2H, m), 4.06-4.16 (1H, m), 3.78-3.88 (1H, m), 3.48-3.64 (2H, m), 2.19 (3H, s), 2.07 (3H, s), 2.06 (3H, s), 2.04 (3H, s), 2.02 (3H, s), 1.93 (3H, s). ESI-MS(m/z):593[M$^+$].

Step 5

Synthesis of 4-[(3-fluoro-4-methylphenyl)methyl]-1-isopropyl-5-methyl-1H-pyrazole-3-o-β-D-glucopyranoside 4'-[(3'-Fluoro-4'-methylphenyl)methyl]-1'-isopropyl-5'-methyl-1H-pyrazole-3'-o-(2,3,4,6-tetraacetyl)-β-D-glucopyranoside (56 mg; 0.09 mmol) was dissolved in methanol (0.2 ml) and tetrahydrofuran (0.4 ml), to which 1N LiOH (0.38 ml) was added at 0° C. After stirring for one hour, water and ethyl acetate were added to the mixture, then organic layer of the mixture was extracted. After drying and concentration, followed by purification by silica gel chromatography (15% methanol:dichloromethane), the resulting purified product was concentrated under reduced pressure, to give the desired compound (34 mg; 0.08 mmol). (85%).

$^1$H-NMR (300 MHz, DMSO-d6) δ: 7.11 (1H, t, J=8.4), 5.19 (1H, d, J=4.8), 5.09 (1H, d, J=7.5), 4.99 (1H, d, J=3.9), 4.91 (1H, d, J=4.2), 4.41 (1H, t, J=5.7), 4.28-4.38 (1H, m), 3.56 (2H, m), 3.54-3.64 (1H, m), 3.40-3.50 (1H, m), 3.06-3.24 (4H, m), 2.13 (3H, s), 2.05 (3H, s), 1.26 (3H, d, J=3.0), 1.24 (3H, d, J=3.0). ESI-MS(m/z):425[(M+H)$^+$], 423[(M−H)$^-$].

Production Example 14-A

Synthesis of 4'-[(3'-fluoro-4'-methylphenyl)methyl]-1'-isopropyl-5'-methyl-1H-pyrazole-3'-o-(6-carbomethoxy)-β-D-glucopyranoside The objective compound (283 mg; 0.59 mmol) was obtained, using 4-[(3-fluoro-4-methylphenyl)methyl]-1-isopropyl-5-methyl-1H-pyrazole-3-o-β-D-glucopyranoside (334 mg; 0.787 mmol) in the same manner as in Production Example 12-A. Yield 75%.

$^1$H-NMR (300 MHz, DMSO-d6) δ: 1.26 (3H, d, J=6.3 Hz), 1.28 (3H, d, J=6.3 Hz), 2.07 (3H, s), 2.15 (3H, s), 3.09-3.41 (4H, m), 3.56 (2H, s), 4.10 (1H, dd, J=6.0, 11.4 Hz), 4.29 (1H, dd, J=1.8, 11.7 Hz), 4.34 (1H, m), 5.10 (1H, d, J=7.8 Hz), 5.13 (1H, d, J=5.1 Hz), 5.24 (1H, d, J=5.1 Hz), 5.31 (1H, d, J=5.1 Hz), 6.89-7.13 (3H, m). ESI-MS(m/z):483 [M+H]$^+$ 481 [(M−H)$^-$]

Production Example 15-A

Synthesis of 4-[(4-ethylphenyl)methyl]-1-isopropyl-5-methyl-1H-pyrazole-3-o-β-D-glucopyranoside

Step 1

Synthesis of ethyl 2-(4-ethylbenzyl)-3-oxobutylate

The objective compound (3.9 g; 15.7 mmol) was obtained, using 4-ethylbenzaldehyde (3.0 g) in the same manner as in Production Example 9-A. Yield 70%.

$^1$H-NMR (300 MHz, CDCl$_3$) δ: 4.15 (2H, q, J=7.2), 3.76 (1H, t, J=7.5), 3.12 (2H, d, J=8.1), 2.60 (2H, q, J=7.8), 2.19 (3H, s), 1.21 (6H, t, J=7.2).

Step 2

Synthesis of 1,2-dihydro-4-[(4-ethylphenyl)methyl]-5-methyl-3H-pyrazol-3-one

The objective compound (3.1 g; 14.3 mmol) was obtained, using ethyl 2-(4-ethylbenzyl)-3-oxobutylate (3.9 g) in the same manner as in the Step 2 of Production Example 9-A. Yield 91%.

$^1$H-NMR (300 MHz, DMSO-d6) δ: 7.06 (4H, s), 3.49 (2H, s), 2.52 (2H, q, J=7.8), 1.99 (3H, s), 1.33 (3H, t, J=7.5). ESI-MS(m/z):217[(M+H)$^+$], 215[(M−H)$^−$].

Step 3

Synthesis of 4'-[(4-ethylphenyl)methyl]-5'-methyl-1H-pyrazole-3'-o-(2,3,4,6-tetrabenzyl)-β-D-glucopyranoside The objective compound (2.3 g; 3.1 mmol) was obtained, using 1,2-dihydro-4-[(4-ethylphenyl)methyl]-5-methyl-3H-pyrazol-3-one (1.0 g; 4.6 mmol) in the same manner as in the Step 3 of Production Example 9-A. Yield 62%.

$^1$H-NMR (300 MHz, CDCl$_3$) δ: 7.10-7.34 (20H, m), 7.07 (2H, d, J=8.4), 6.97 (2H, d, J=8.4), 5.23 (1H, d, J=6.9), 4.44-5.00 (8H, m), 3.56-3.80 (8H, m), 2.50 (2H, q, J=7.5), 2.08 (3H, s), 1.13 (3H, t, J=7.5). ESI-MS(m/z):739[(M+H)$^+$], 737 [(M−H)$^−$].

Step 4

Synthesis of 4'-[(4-ethylphenyl)methyl]-1'-isopropyl-5'-methyl-1H-pyrazole-3'-o-(2,3,4,6-tetrabenzyl)-β-D-glucopyranoside The objective compound (1.6 g; 2.0 mmol) was obtained, using 4'-[(4-ethylphenyl)methyl]-5'-methyl-1H-pyrazole-3'-o-(2,3,4,6-tetrabenzyl)-β-D-glucopyranoside (1.9 g; 2.6 mmol) in the same manner as in the Step 4 of Production Example 9-A. Yield 79%.

$^1$H-NMR (300 MHz, CDCl$_3$) δ: 7.14-7.38 (20H, m), 7.07 (2H, d, J=8.1), 6.97 (2H, d, J=8.1), 5.47 (1H, d, J=7.5), 4.20-5.00 (9H, m), 3.60-3.76 (8H, m), 2.52 (2H, q, J=7.8), 2.07 (3H, s), 1.37 (6H, t, J=6.9), 1.14 (3H, t, J=8.1): 781[(M+H)$^+$].

Step 5

Synthesis of 4-[(4-ethylphenyl)methyl]-1-isopropyl-5'-methyl-1H-pyrazole-3-o-β-D-glucopyranoside The objective compound (743 mg; 1.8 mmol) was obtained, using 4'-[(4-ethylphenyl)methyl]-1'-isopropyl-5'-methyl-1H-pyrazole-3'-o-(2,3,4,6-tetrabenzyl)-β-D-glucopyranoside in the same manner as in the Step 5 of Production Example 9-A. Yield 87%.

$^1$H-NMR (300 MHz, DMSO-d6) δ: 7.09 (2H, d, J-7.8), 7.03 (2H, d, J=7.8), 5.18 (1H, brd, J=4.5), 5.11 (1H, d, J=6.9), 4.84-5.02 (2H, m), 4.26-4.44 (3H, m), 3.40 3.64 (3H, m), 3.04-3.26 (4H, m), 2.51 (2H, q, J=7.5), 2.06 (3H, s), 1.25 (6H, d, J=6.6), 1.14 (3H, t, J=5.7):421[(M+H)$^+$], 419[(M−H)$^−$].

Production Example 16-A

Synthesis of 4'-[(4-ethylphenyl)methyl]-1'-isopropyl-5'-methyl-1H-pyrazole-3'-o-(6-carbomethoxy)-β-D-glucopyranoside The objective compound (570 mg; 1.2 mmol) was obtained, using 4-[(4-ethylphenyl)methyl]-1-isopropyl-5'-methyl-1H-pyrazole-3-o-β-D-glucopyranoside (702 mg; 1.67 mmol) in the same manner as in Production Example 10-A. Yield 71%.

$^1$H-NMR (300 MHz, CDCl$_3$) δ: 7.08 (4H, s), 4.99 (1H, d, J=7.5), 4.24-4.48 (4H, m), 3.77 (3H, s), 3.44-3.68 (6H, m), 2.94-3.16 (2H, m), 2.58 (2H, q, J=7.8), 2.09 (3H, s), 1.36 (6H, d, J=6.6), 1.20 (3H, t, J=7.8) ESI-MS(m/z):479[(M+H)$^+$], 477 [(M−H)$^−$].

The structures of the compounds of Production Examples 1-A through 16-A are shown below.

Compound of Production Example 1-A

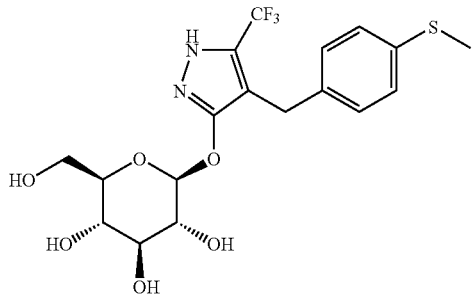

Compound of Production Example 2-A

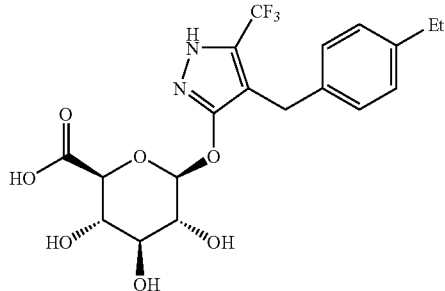

Compound of Production Example 3-A

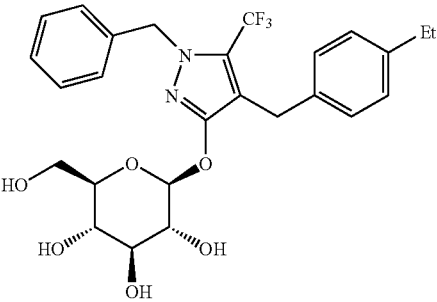

-continued
Compound of Production Example 4-A
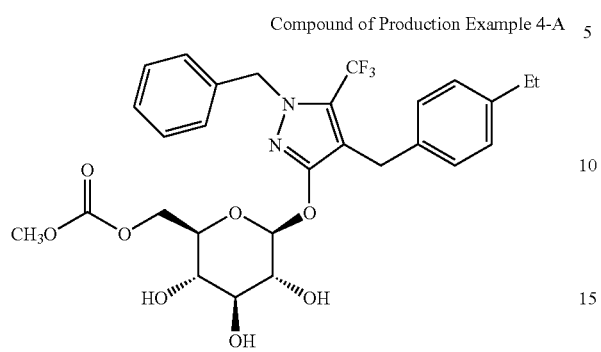
Compound of Production Example 5-A
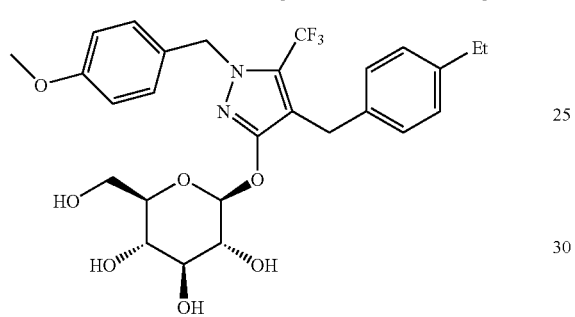
Compound of Production Example 6-A
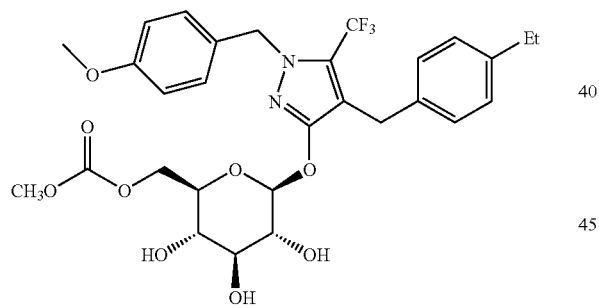
Compound of Production Example 7-A
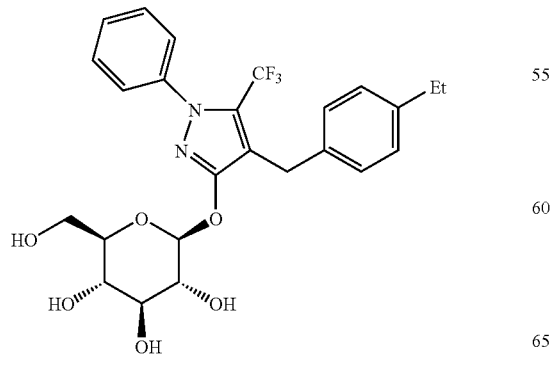
-continued
Compound of Production Example 8-A
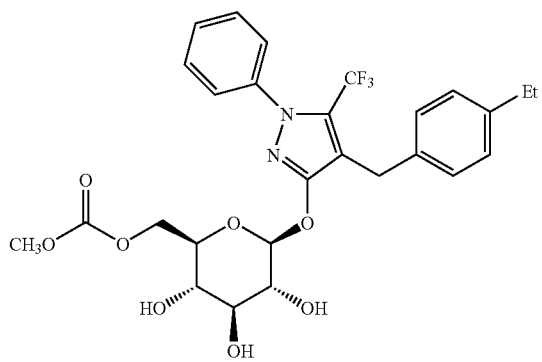
Compound of Production Example 9-A
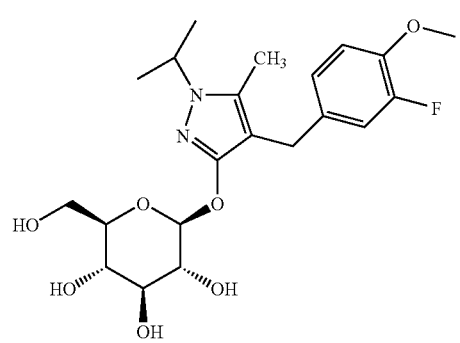
Compound of Production Example 10-A
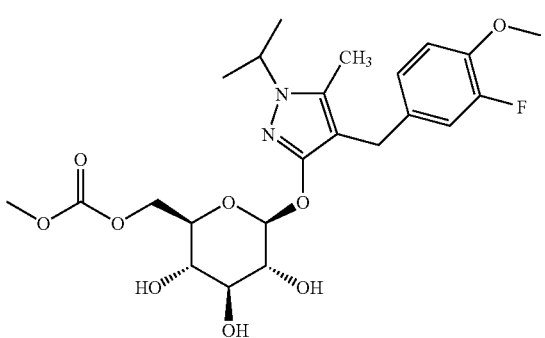
Compound of Production Example 11-A
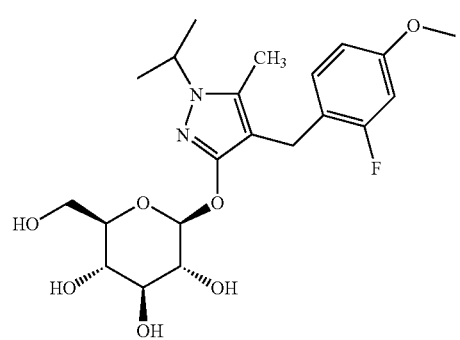

Compound of Production Example 12-A

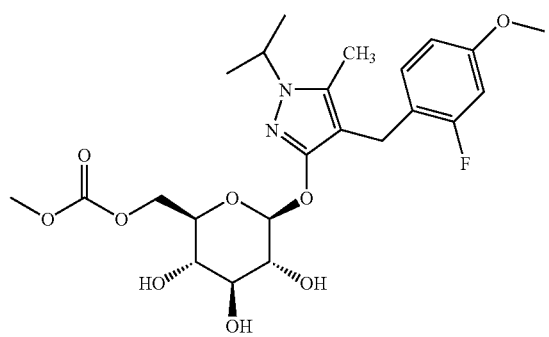

Compound of Production Example 13-A

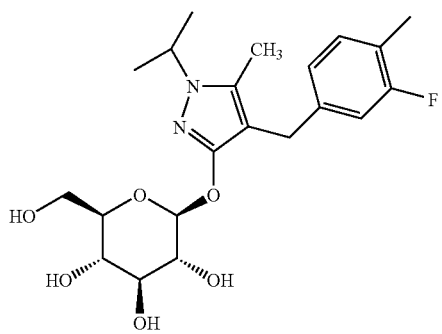

Compound of Production Example 14-A

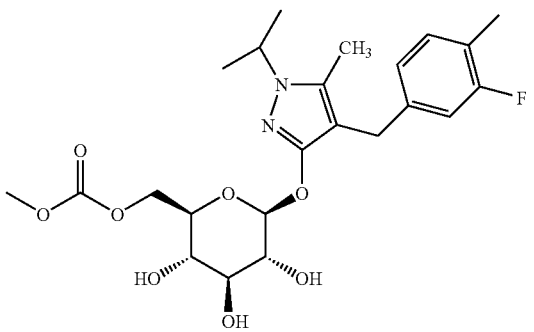

Compound of Production Example 15-A

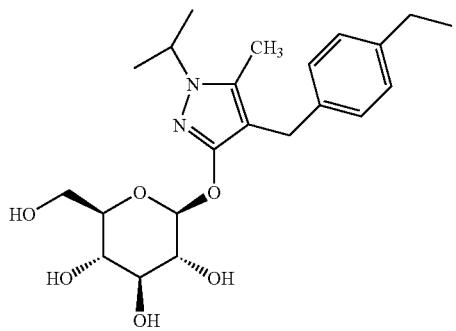

Compound of Production Example 16-A

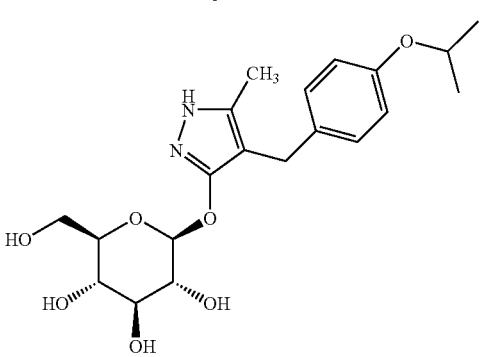

Reference Production Example 1

Example 35 of WO 01/16147

Synthesis of 4-[(4-isopropoxyphenyl)methyl]-5-methyl-1H-pyrazole-3-o-β-D-glucopyranoside Synthesized by the method described in the Production Example 9-A. Yield 253 mg $^1$H-NMR (300 MHz, DMSO-d6) δ: 7.07 (1H, d, J=8.4), 6.75 (1H, d, J=8.4), 5.12-5.20 (2H, m), 5.00 (1H, d, J=3.9), 4.92 (1H, d, J=3.9), 4.42-4.56 (2H, m), 3.58-3.68 (1H, m), 3.51 (2H, s), 3.42-3.54 (1H, m), 3.06-3.24 (4H, m), 2.00 (3H, s), 1.22 (6H, d, J=6.3) ESI-MS(m/z):409[(M+H)$^+$], 407[(M−H)$^-$].

The structure of the compound of the Reference Production Example 1 is shown below.

Compound of Reference Production Example 1

Test Example 1A

Assessment of Inhibitory Action of Glucose Uptake

Test compounds were dissolved in 100 mM mannitol-10 mM HEPES/Tris, pH 7.4 to prepare solutions at various concentrations.

Renal brush border membrane was prepared from a rat kidney, to which a solution of a test compound was added for incubation at 37° C. for 30 minutes. Then, $^{14}$C-D-glucose was added for incubation for one minute. A solution containing 1 mM phlorizin was used to terminate the glucose uptake reaction. The radioactivity $^{14}$C of $^{14}$C-D-glucose incorporated in the renal brush border membrane was counted with a liquid scintillation counter. The glucose uptake independent on sodium was reduced from the glucose uptake in a control group or a test group, to calculate the inhibition intensity. The results are shown in Table 1A.

TABLE 1A

| Test compound | Inhibition intensity (concentration of test compound) |
|---|---|
| Compound of Production Example 1-A | 84% (10 µM) |
| Compound of Production Example 2-A | 30% (100 µM) |

Test Example 2A

Assessment of Excretion Action of Urine Sugar in Rat

Male Wistar rats aged 5 weeks (purchased from Charles River Japan, Inc.) were acclimatized in metabolic cages for one week, for use at this experiment. The test compounds suspended in olive oil were dosed at 5 ml per 1 kg rat body weight.

After the rats were starved for 4 hours, the test compounds were orally given to the rats at 11 am. Immediately after dosing until 24 hours later, urine was collected. The volume of urine was measured. Then, urine sugar concentration was assayed by glucose oxidase method, to calculate the glucose excretion into urine per individual per day. The results are shown in Table 2A.

TABLE 2A

|  | Dose | Excreted urine sugar (mg) |
|---|---|---|
| Compound of Production Example 4-A | 100 mg/kg | 27 |
| Compound of Production Example 6-A | 100 mg/kg | 59 |
| Compound of Production Example 8-A | 100 mg/kg | 4.1 |
| Compound of Production Example 10-A | 100 mg/kg | 734 |
| Compound of Production Example 14-A | 100 mg/kg | 918 |
| Compound of Production Example 16-A | 100 mg/kg | 598 |
|  | 30 mg/kg | 294 |
|  | 10 mg/kg | 263 |
|  | 3 mg/kg | 28 |
| Compound of Reference Production Example 1 | 100 mg/kg | 14 |

As apparently shown above, the resulting pyrazole derivatives showed great inhibitory activities of glucose uptake and excretion actions of urine sugar.

Production Example 1B

Step 1

Synthesis of 3-t-butyldimethylsilyloxy-4-((4-ethylphenyl)methyl)-5-(trifluoromethyl)-1H-pyrazole 1,2-Dihydro-4-((4-ethylphenyl)methyl)-5-(trifluoromethyl)-3H-pyrazol-3-one (4) (prepared by the method described in J. Med. Chem 1996, 39, 3920-3928) (15.0 g; 55.6 mmol) was dissolved in dimethylformamide (150 ml) and cooled to 0° C. t-Butyldimethylsilyl chloride (9.3 g; 61.1 mmol) was added in portions, and then, imidazole (4.2 g; 61.1 mmol) was added in portions. Then, the resulting mixture was back to ambient temperature, then the mixture was stirred for 3 hours. Water was added to the reaction solution, for extraction twice with ethyl acetate. The organic phase was washed with aqueous saturated sodium chloride, dried over anhydrous sodium sulfate and concentrated, to give the desired compound (21.4 g; 55.6 mmol). (100%)

Step 2

Synthesis of 3-t-butyldimethylsilyloxy-4-((4-ethylphenyl)methyl)-1-(1,3-difluoro-2-propyl)-5-(trifluoromethyl)pyrazole 3-t-Butyldimethylsilyloxy-4-((4-ethylphenyl)methyl)-5-(trifluoromethyl)-1H-pyrazole (2.0 g; 5.2 mmol) was dissolved in tetrahydrofuran (20 ml), followed by addition of triphenylphosphine (1.6 g; 6.25 mmol) and 1,3-difluoro-2-propanol (0.48 ml; 6.25 mmol). The solution was cooled to 0° C. A 40% diethyl azodicarboxylate/toluene solution (2.84 ml; 6.25 mmol) was gradually added while the temperature of the reaction solution was controlled under 10° C. After the reaction solution was back to room temperature for 2 hours, the reaction solution was concentrated. A solvent of ethyl acetate-hexane (1:10) was added to the concentrate solution, then triphenylphosphine was filtered off. The filtrate was concentrated and purified on a silica gel column chromatography (ethyl acetate-hexane=1:4), to give the desired difluoroisopropyl compound (1.95 g; 4.22 mmol). (81%)

$^1$H-NMR (300 MHz, DMSO-d6) δ: 0.22 (6H, s), 0.91 (9H, s), 1.13 (3H, t, J=7.5), 2.53 (2H, q, J=7.5), 3.70 (2H, s), 4.65 (2H, brs), 4.81 (3H, brs), 7.02 (2H, d, J=8.4), 7.11 (2H, d, J=8.7). ESI-MS(m/z):347[(M-TBS)$^-$]

Step 3

Synthesis of 1,2-dihydro-4-((4-ethylphenyl)methyl)-1-(1,3-difluoro-2-propyl)-5-(trifluoromethyl)-3H-pyrazol-3-one 3-t-Butyldimethylsilyloxy-4-((4-ethylphenyl)methyl)-1-(1,3-difluoro-2-propyl)-5-(trifluoromethyl)pyrazole (1.95 g; 4.22 mmol) was dissolved in tetrahydrofuran (30 ml) and cooled to 0° C. A 1 M tetrabutylammonium fluoride-tetrahydrofuran solution (6.33 ml; 6.33 mmol) was gradually added, then the mixture was stirred at room temperature for 30 minutes. The reaction solution was concentrated, and the residue was purified on a silica gel column chromatography (ethyl acetate-hexane=1:4) to give the desired compound (684 mg; 1.96 mmol). (46%)

$^1$H-NMR (300 MHz, DMSO-d6) δ: 1.18 (3H, t, J=7.5), 2.58 (2H, q, J=7.5), 3.74 (2H, s), 4.70 (2H, s), 4.86 (3H, brs), 7.08 (2H, d, J=7.8), 7.15 (2H, d, J=8.4), 10.75 (1H, brs). ESI-MS (m/z):347[(M−H)$^-$]

Step 4

Synthesis of 4'-[(4'-ethylphenyl)methyl]-1'-(1,3'-difluoro-2'-propyl)-5'-(trifluoromethyl)-1H-pyrazole-3'-o-(2,3,4,6-o-tetraacetyl)-β-D-glucopyranoside 1,2-Dihydro-4-((4-ethylphenyl)methyl)-1-(1,3-difluoro-2-propyl)-5-(trifluoromethyl)-3H-pyrazol-3-one (684 mg; 1.96 mmol) was dissolved in chloroform (10 ml), followed by addition of potassium carbonate (2.2 g; 15.7 mmol) and benzyltributylammonium chloride (153 mg; 0.49 mmol). The mixture was stirred at room temperature, further, 2,3,4,6-tetraacetyl-α-D-glucopyranosyl bromide (1.2 g; 2.94 mmol) was added. The reaction solution was stirred overnight at room temperature. The reaction solution was neutralized with aqueous 1N hydrochloric acid, to which aqueous saturated sodium chloride was added, then the mixture was extracted three times with dichloromethane. The organic phase was dried, concentrated, and purified on a silica gel column chromatography (ethyl acetate-hexane=1:2) to give the desired compound (2.51 g; 3.7 mmol). (Mixture with acetobromoglucose)

¹H-NMR (300 MHz, DMSO-d6) δ: 1.13 (3H, t, J=7.5), 1.89 (3H, s), 1.96 (3H, s), 1.97 (3H, s), 2.00 (3H, s), 2.53 (2H, q, J=7.5), 3.69 (2H, s), 3.98-4.04 (1H, m), 4.11-4.19 (3H, m), 4.69 (1H, t, J=5.7), 4.84 (1H, t, J=6.6), 4.96-5.11 (3H, m), 5.46 (1H, t, J=9.6), 5.85 (1H, d, J=8.1), 6.98 (2H, d, J=8.1), 7.09 (2H, d, J=8.1), ESI-MS(m/z): 679[(M+H)⁺]

Step 5

Synthesis of 4-[(4-ethylphenyl)methyl]-1-(1,3-difluoro-2-propyl)-5-(trifluoromethyl)-1H-pyrazole-3-o-β-D-glucopyranoside 4'-[(4'-Ethylphenyl)methyl]-1'-(1',3'-difluoro-2'-propyl)-5'-(trifluoromethyl)-1H-pyrazole-3'-o-(2,3,4,6-o-tetraacetyl)-β-D-glucopyranoside (1.33 g; 1.96 mmol) was dissolved in tetrahydrofuran (2 ml) and methanol (2 ml), followed by addition of 1N lithium hydroxide. Then the mixture was stirred at room temperature. 30 minutes later, the resulting mixture was neutralized with aqueous 1N hydrochloric acid, followed by addition of aqueous saturated sodium chloride. After extraction with ethyl acetate, the resulting ethyl acetate layer was dried over anhydrous sodium sulfate. After concentration, the residue was purified on a silica gel column (methanol-dichloromethane=1:10, to give the desired compound (1.52 g; 2.98 mmol).

¹H-NMR (300 MHz, DMSO-d6) δ: 1.14 (3H, t, J=7.5), 2.54 (2H, q, J=7.5), 3.19-3.25 (4H, m), 3.47 (1H, m), 3.61-3.66 (1H, m), 3.77 (2H, s), 4.47 (1H, t, J=6.0), 4.66 (1H, t, J=4.8), 4.82 (1H, t, J=4.8), 4.83-4.97 (1H, m), 4.97 (1H, d, J=3.0), 5.08 (1H, d, J=4.2), 5.23 (1H, d, J=7.5), 5.36 (1H, d, J=4.8), 7.09 (4H, s), ESI-MS(m/z): 509[(M–H)⁻]

Production Example 2B

Synthesis of 4'-[(4'-ethylphenyl)methyl]-1'-(1',3'-difluoro-2'-propyl)-5'-(trifluoromethyl)-1H-pyrazole-3'-o-(6-o-methoxycarbonyl-β-D-glucopyranoside)

4-[(4-Ethylphenyl)methyl]-1-(1,3-difluoro-2-propyl)-5-(trifluoromethyl)-1H-pyrazole-3-o-β-D-glucopyranoside (700 mg; 1.37 mmol) was dissolved in 2,4,6-collidine (10 ml), and cooled to –10° C. Methyl chlorocarbonate (0.13 ml; 1.64 mmol) was added to the resulting mixture, and the mixture was at –10° C. overnight. The mixture was neutralized with 2N hydrochloric acid, followed by addition of aqueous saturated sodium chloride and the mixture was extracted twice with ethyl acetate. The organic layer was washed sequentially with 1N hydrochloric acid, aqueous saturated sodium carbonate, and aqueous sodium chloride, and then dried and concentrated. The residue was purified on a silica gel column chromatography (5% MeOH—CH₂Cl₂) to give the desired compound (526 mg). (68%)

¹H-NMR (300 MHz, DMSO-d6) δ: 1.14 (3H, t, J=7.5), 2.53 (2H, q, J=7.5), 3.15-3.30 (4H, m), 3.46-3.51 (1H, m), 3.75 (2H, s), 4.12 (1H, d, J=11.7), 4.32 (1H, d, J=11.7), 4.64-4.68 (2H, m), 4.80-4.83 (2H, m), 4.91 (1H, m), 5.21 (1H, d, J=4.2), 5.22 (1H, d, J=7.8), 5.31 (1H, d, J=5.7), 5.46 (1H, d, J=4.8), 7.08 (4H, s). ESI-MS(m/z): 569 [ (M+H)⁺], 567 [(M–H)⁻].

The structures of the compounds of Production Examples 1B and 2B are shown below.

Compound of Production Example 1B

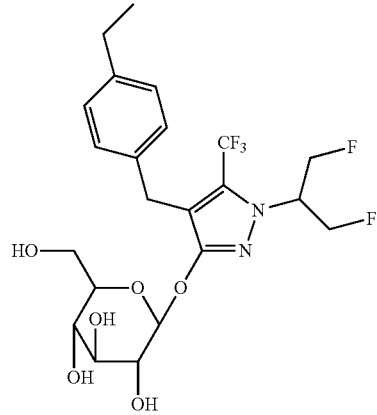

Compound of Production Example 2B

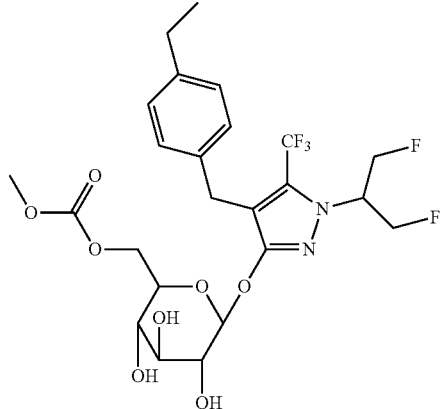

Test Example 1B

Assessment of Excretion Action of Urine Sugar in Rat

Male Wistar rats aged 5 weeks (purchased from Charles River Japan, Inc.) were acclimatized in metabolic cages for one week, for use at this experiment. The test compounds suspended in olive oil were prepared into solutions to a dose of 5 ml per 1 kg rat body weight. After the rats were starved for 4 hours, the test compounds were orally given at 10, 30 and 100 mg/kg to the rats at 11 am. Immediately after dosing until 24 hours later, urine was collected. The volume of urine was measured. Then, urine glucose concentration was assayed by glucose oxidase method, to calculate the glucose excretion into urine per individual per day. As a positive control, 3-(5-benzo[b]furanyl)-2'-(6-o-methoxycarbonyl-β-D-glucopyranosyloxy)-6'-hydroxy-4'-methylpropiophenone [under a different name of 3-(benzo[b]furan-5-yl)-2',6'-dihydroxy-4'-methylpropiophenone 2'-o-(6-o-methoxycarbonyl-β-D-glucopyranoside)] was used. The results are shown in Table 1B.

TABLE 1B

Excreted Urine Sugar Amount in Oral Administration in Rat (24 hours)

| Test compound | Dose (mg/kg) | Excreted urine sugar (mg) |
| --- | --- | --- |
| Compound of Production Example 2B | 10 | 136 |
| | 30 | 272 |
| | 100 | 524 |
| Positive control* | 10 | 2 |
| | 30 | 78 |
| | 100 | 274 |

*Compound name: 3-(5-benzo[b]furanyl)-2'-(6-o-methoxycarbonyl-β-D-glucopyranosyloxy)-6'-hydroxy-4'-methylpropiophenone [under a different name of 3-(benzo[b]furan-5-yl)-2', 6'-dihydroxy-4'-methylpropiophenone 2'-o-(6-o-methoxycarbonyl-β-D-glucopyranoside)]

As apparently shown above, the resulting pyrazole-o-glycoside derivatives when given orally at low doses showed great actions on the excretion of urine sugar.

INDUSTRIAL APPLICABILITY

The prophylactic and therapeutic agent of diabetes mellitus in accordance with the invention can produce a therapeutic effect of diabetes mellitus, as never has been obtained by the hypoglycemic agents of the relates art, specifically a hypoglycemic pattern as never been obtained by the use of the hypoglycemic agents of the related art and a greater antidiabetic action after repeated administration than those obtained by the administration of anti-diabetic agents of the related art. Therefore, the invention is very useful for the prophylaxis and therapeutic treatment of diseases diagnosed on the basis of blood glucose level.

This application is based on Japanese Patent Application 2002-127691 filed in Japan, of which all the contents are encompassed within this specification.

The invention claimed is:

1. A therapeutic agent of diabetes mellitus, comprising a combination of an inhibitor of renal glucose reabsorption and a hypoglycemic agent, wherein said hypoglycemic agent is at least one selected from the group consisting of glibenclamide, nateglinide, and metformin, and said inhibitor of renal glucose reabsorption is at least one selected from the group consisting of:

a pyrazole derivative of formulae (1) and/or (2) or a pharmaceutically acceptable salt thereof:

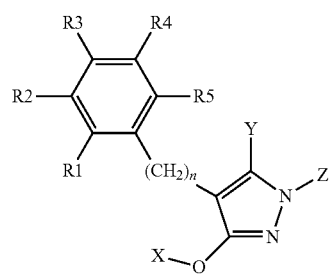

(1)

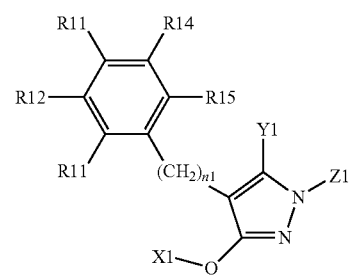

(2)

wherein

X represents β-D-glucopyranosyl group wherein one or plural hydroxyl groups may be acylated;

Y represents a lower alkyl group, a fluoro-lower alkyl group or a perfluoro-lower alkyl group;

Z represents a cyclic alkyl group optionally substituted with a methyl group, an ethyl group, a methoxy group, an ethoxy group, a fluorine atom, a chlorine atom, or a bromine atom, a cyclic unsaturated alkyl group optionally substituted with a methyl group, an ethyl group, a methoxy group, an ethoxy group, a fluorine atom, a chlorine atom or a bromine atom, a lower alkyl group with unsaturated bond, a lower alkyl group with a cyclic alkyl group optionally substituted with a methyl group, an ethyl group, a methoxy group, an ethoxy group, a fluorine atom, chlorine atom or a bromine atom, or a lower alkyl group with a cyclic unsaturated alkyl group optionally substituted with a methyl group, an ethyl group, a methoxy group, an ethoxy group, a fluorine atom, chlorine atom or a bromine atom;

R1 through R5 may be the same or different and represent hydrogen atom, a lower alkyl group, a fluoro-lower alkyl group, a perfluoro-lower alkyl group, a lower alkoxy group, a fluoro-lower alkoxy group, a perfluoro-lower alkoxy group, a lower alkylthio group, a fluoro-lower alkylthio group, a perfluoro-lower alkylthio group, a lower alkylamino group, a halogeno group, a lower alkanoyl group, an alkenyl group, a cyclic alkenyl group, an alkynyl group, an aralkyl group optionally substituted with a lower alkoxy group, a lower alkyl group, a halogeno group or a halogeno-lower alkyl group, a phenyl group optionally substituted with a lower alkoxy group, a lower alkyl group, a halogeno group or a halogeno-lower alkyl group, or a lower alkoxy-carbonyl group; and n represents an integer of 0 to 3;

a pyrazole derivative of formulae (1A) and/or (2A) or a pharmaceutically acceptable salt thereof:

(1A)

-continued (2A)

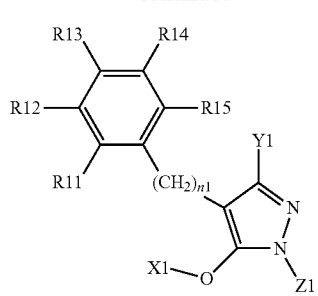

wherein
X1 represents β-D-glucopyranosyl group, wherein one or plural hydroxyl groups may be acylated, or β-D-glucuronyl group, wherein one or plural hydroxyl groups may be acylated and carboxyl group may be esterified;
Y1 represents a lower alkyl group or a perfluoro-lower alkyl group;
Z1 represents hydrogen atom, a lower alkyl group, a perfluoro-lower alkyl group, an aralkyl group optionally substituted with a lower alkoxy group, a lower alkyl group, a halogeno group or a halogeno-lower alkyl group, or a phenyl group optionally substituted with a lower alkoxy group, a lower alkyl group, a halogeno group or a halogeno-lower alkyl group;
R11 through R15 may be the same or different and represent hydrogen atom, a lower alkyl group, a perfluoro-lower alkyl group, a lower alkoxy group, a perfluoro-lower alkoxy group, a lower alkylthio group, a perfluoro-lower alkylthio group, a lower alkylamino group, a halogeno group, a lower alkanoyl group, a lower alkenyl group or a lower alkynyl group; and
n1 represents an integer of 0 to 3;
at least one selected from a pyrazole-o-glycoside derivative of formula (5) or a pharmaceutically acceptable salt thereof:

(5)

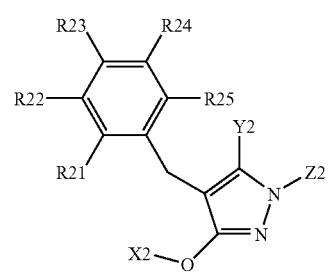

wherein
X2 represents β-D-glucopyranosyl group, wherein one or plural hydroxyl groups may be acylated;
Y2 represents hydrogen, a lower alkyl group, a fluoro-lower alkyl group or a perfluoro-lower alkyl group;
Z2 represents a halo-lower alkyl group;
R21 through R25 may be the same or different and represent hydrogen atom, a halogeno group, a lower alkyl group, a halo-lower alkyl group, a perfluoro-lower alkyl group, a lower alkoxy group, a perfluoro-lower alkoxy group, a lower alkylthio group, a perfluoro-lower alkylthio group, a lower alkylamino group, a lower alkanoyl group, a lower alkenyl group, a lower alkynyl group or an aralkyl group optionally substituted with a lower alkoxy group, a lower alkyl group, a halogeno group or a halogeno-lower alkyl group; and at least one selected from a glucopyranosyloxypyrazole derivative of formula (8) or a pharmaceutically acceptable salt thereof:

(8)

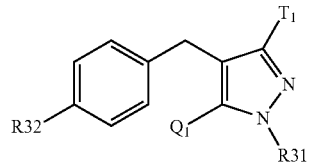

wherein
R31 is hydrogen atom or a lower alkyl group;
either one of $Q_1$ and $T_1$ is a group of the formula (9):

(9)

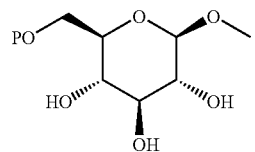

wherein P represents hydrogen atom, a lower acyl group, a lower alkoxy-lower acyl group, a lower alkoxy-carbonyl-lower acyl group, a lower alkoxy-carbonyl group or a lower alkoxy-lower alkoxy-carbonyl group, and the other is a lower alkyl group or a halo-lower alkyl group;
R32 is hydrogen atom, a lower alkyl group, a lower alkoxy group, a lower alkylthio group, a halo-lower alkyl group or a halogen atom.

2. A therapeutic agent of diabetes mellitus according to claim 1, where the hypoglycemic agent is glibenclamide.

3. A therapeutic agent of diabetes mellitus according to claim 1, where the hypoglycemic agent is metformin.

4. A therapeutic agent of diabetes mellitus according to claim 1, where the hypoglycemic agent is nateglinide.

5. A therapeutic agent of diabetes mellitus according to claim 1, where the inhibitor of renal glucose reabsorption is at least one pyrazole derivative of formulae (1) and/or (2) or a pharmaceutically acceptable salt thereof:

(1)

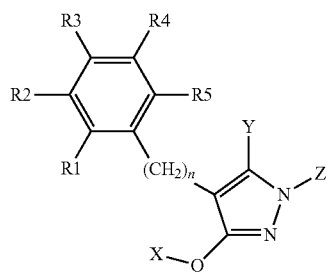

(2)

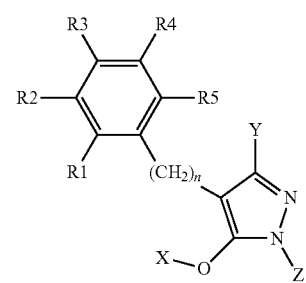

wherein
- X represents β-D-glucopyranosyl group wherein one or plural hydroxyl groups may be acylated;
- Y represents a lower alkyl group, a fluoro-lower alkyl group or a perfluoro-lower alkyl group;
- Z represents a cyclic alkyl group optionally substituted with a methyl group, an ethyl group, a methoxy group, an ethoxy group, a fluorine atom, a chlorine atom, or a bromine atom, a cyclic unsaturated alkyl group optionally substituted with a methyl group, an ethyl group, a methoxy group, an ethoxy group, a fluorine atom, a chlorine atom or a bromine atom, a lower alkyl group with unsaturated bond, a lower alkyl group with a cyclic alkyl group optionally substituted with a methyl group, an ethyl group, a methoxy group, an ethoxy group, a fluorine atom, chlorine atom or a bromine atom, or a lower alkyl group with a cyclic unsaturated alkyl group optionally substituted with a methyl group, an ethyl group, a methoxy group, an ethoxy group, a fluorine atom, chlorine atom or a bromine atom;
- R1 through R5 may be the same or different and represent hydrogen atom, a lower alkyl group, a fluoro-lower alkyl group, a perfluoro-lower alkyl group, a lower alkoxy group, a fluoro-lower alkoxy group, a perfluoro-lower alkoxy group, a lower alkylthio group, a fluoro-lower alkylthio group, a perfluoro-lower alkylthio group, a lower alkylamino group, a halogeno group, a lower alkanoyl group, an alkenyl group, a cyclic alkenyl group, an alkynyl group, aralkyl group optionally substituted with a lower alkoxy group, a lower alkyl group, a halogeno group or a halogeno-lower alkyl group, a phenyl group optionally substituted with a lower alkoxy group, a lower alkyl group, a halogeno group or a halogeno-lower alkyl group, or a lower alkoxy-carbonyl group; and
- n represents an integer of 0 to 3.

6. A therapeutic agent of diabetes mellitus according to claim 5, where the inhibitor of renal glucose reabsorption is at least one pyrazole derivative where Z is a cyclic alkyl group optionally substituted with a methyl group, an ethyl group, a methoxy group, an ethoxy group, a fluorine atom, a chlorine atom, or a bromine atom in formulae (1) and (2) or a pharmaceutically acceptable salt thereof.

7. A therapeutic agent of diabetes mellitus according to claim 5, where the inhibitor of renal glucose reabsorption is at least one pyrazole derivative where Y is trifluoromethyl group in formulae (1) and (2) or a pharmaceutically acceptable salt thereof.

8. A therapeutic agent of diabetes mellitus according to claim 5, where the inhibitor of renal glucose reabsorption is at least one pyrazole derivative where Y is trifluoromethyl group and n is 1 in formulae (1) and (2) or a pharmaceutically acceptable salt thereof.

9. A therapeutic agent of diabetes mellitus according to claim 5, where the inhibitor of renal glucose reabsorption is at least one pyrazole derivative where Y is trifluoromethyl group; n is 1; and X is β-D-glucopyranosyl group, wherein one or plural hydroxyl groups may be acylated with a group or groups selected from alkanoyl groups with 2 to 20 carbon atoms, lower alkoxy-carbonyl groups and benzoyl group, in formulae (1) and (2) or a pharmaceutically acceptable salt thereof.

10. A therapeutic agent of diabetes mellitus according to claim 5, where the inhibitor of renal glucose reabsorption is at least one pyrazole derivative represented by formulae (3), (3a), (4) and/or (4a) or a pharmaceutically acceptable salt thereof:

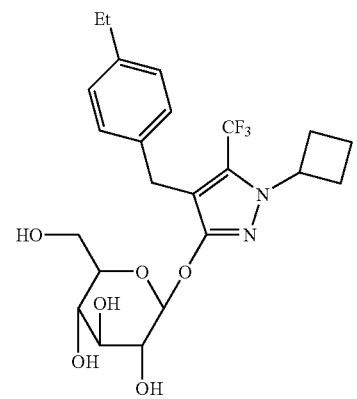

(3)

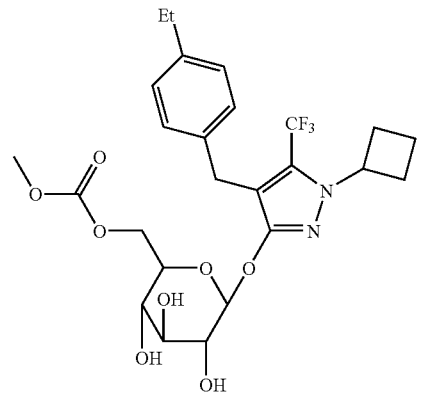

(3a)

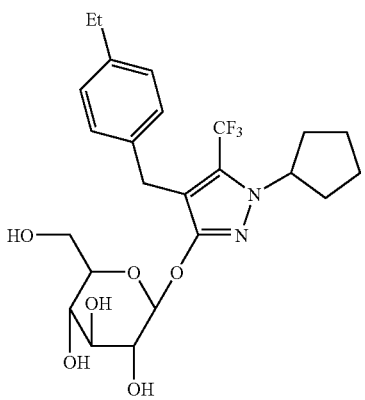

(4)

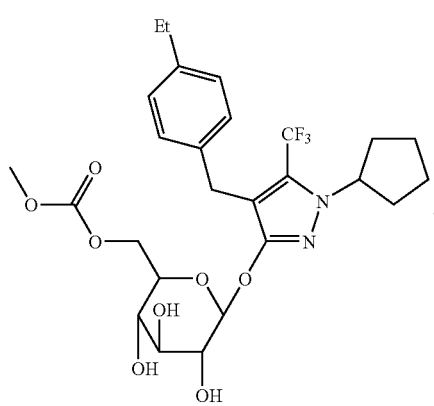

(4a)

11. A therapeutic agent of diabetes mellitus according to claim 1, where the inhibitor of renal glucose reabsorption is at least one pyrazole derivative of formulae (1A) and/or (2A) or a pharmaceutically acceptable salt thereof:

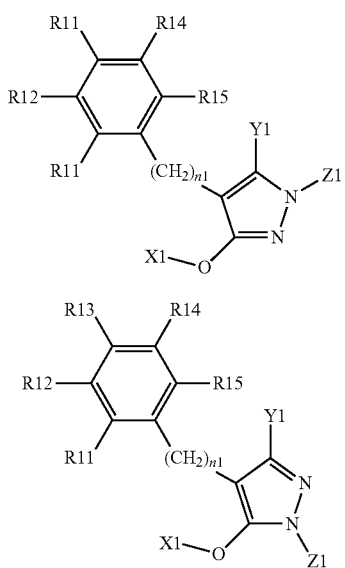

(1A)

(2A)

wherein
- X1 represents β-D-glucopyranosyl group, wherein one or plural hydroxyl groups may be acylated, or β-D-glucuronyl group, wherein one or plural hydroxyl groups may be acylated and carboxyl group may be esterified;
- Y1 represents a lower alkyl group or a perfluoro-lower alkyl group;
- Z1 represents hydrogen atom, a lower alkyl group, a perfluoro-lower alkyl group, an aralkyl group optionally substituted with a lower alkoxy group, a lower alkyl group, a halogeno group or a halogeno-lower alkyl group, or a phenyl group optionally substituted with a lower alkoxy group, a lower alkyl group, a halogeno group or a halogeno-lower alkyl group;
- R11 through R15 may be the same or different and represent hydrogen atom, a lower alkyl group, a perfluoro-lower alkyl group, a lower alkoxy group, a perfluoro-lower alkoxy group, a lower alkylthio group, a perfluoro-lower alkylthio group, a lower alkylamino group, a halogeno group, a lower alkanoyl group, a lower alkenyl group or a lower alkynyl group; and
- n1 represents an integer of 0 to 3.

12. A therapeutic agent of diabetes mellitus according to claim 11, where the inhibitor of renal glucose reabsorption is at least one pyrazole derivative where at least one of R11 through R15 is a lower alkyl group, a perfluoro-lower alkyl group, a lower alkoxy group, a perfluoro-lower alkoxy group, a lower alkylthio group, a perfluoro-lower alkylthio group, a lower alkylamino group, a halogeno group, a lower alkanoyl group, a lower alkenyl group or a lower alkynyl group in formulae (1A) and (2A) or a pharmaceutically acceptable salt thereof.

13. A therapeutic agent of diabetes mellitus according to claim 11, where the inhibitor of renal glucose reabsorption is at least one pyrazole derivative where at least one of R11, R12, R14 and R15 is a halogeno group in formulae (1A) and (2A) or a pharmaceutically acceptable salt thereof.

14. A therapeutic agent of diabetes mellitus according to claim 11, where the inhibitor of renal glucose reabsorption is at least one pyrazole derivative where Y1 is trifluoromethyl group in formulae (1A) and (2A) or a pharmaceutically acceptable salt thereof.

15. A therapeutic agent of diabetes mellitus according to claim 11, where the inhibitor of renal glucose reabsorption is at least one pyrazole derivative where Y1 is trifluoromethyl group and n1 is 1 in formulae (1A) and (2A) or a pharmaceutically acceptable salt thereof.

16. A therapeutic agent of diabetes mellitus according to claim 11, where the inhibitor of renal glucose reabsorption is at least one pyrazole derivative where Y1 is trifluoromethyl group; n1 is 1; and X1 is β-D-glucopyranosyl group (where one or plural hydroxyl groups may be acylated with a group or groups selected from alkanoyl groups with 2 to 20 carbon atoms, lower alkoxy-carbonyl groups and benzoyl group) in formulae (1A) and (2A) or a pharmaceutically acceptable salt thereof.

17. A therapeutic agent of diabetes mellitus according to claim 11, where the inhibitor of renal glucose reabsorption is at least one pyrazole derivative where Y1 is trifluoromethyl group; n1 is 1; and X1 is β-D-glucuronyl group (where one or plural hydroxyl groups may be acylated with a group or groups selected from alkanoyl groups with 2 to 20 carbon atoms, lower alkoxy-carbonyl groups and benzoyl group and where carboxyl group may be esterified with a lower alkyl group) in formulae (1A) and (2A) or a pharmaceutically acceptable salt thereof.

18. A therapeutic agent of diabetes mellitus according to claim 11, where the inhibitor of renal glucose reabsorption is at least one pyrazole derivative represented by formulae (3A), (4A), (10-A), (12-A), (14-A) and/or (16-A) or a pharmaceutically acceptable salt thereof:

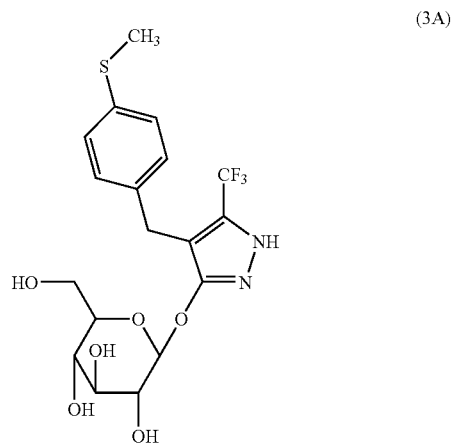

(3A)

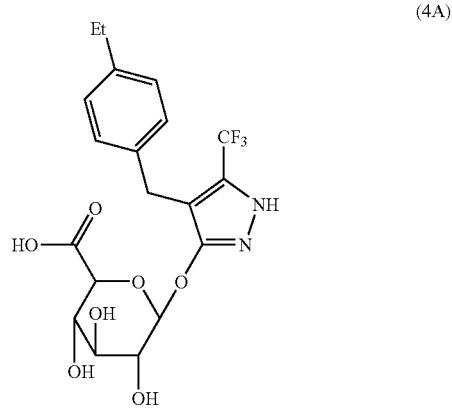

(4A)

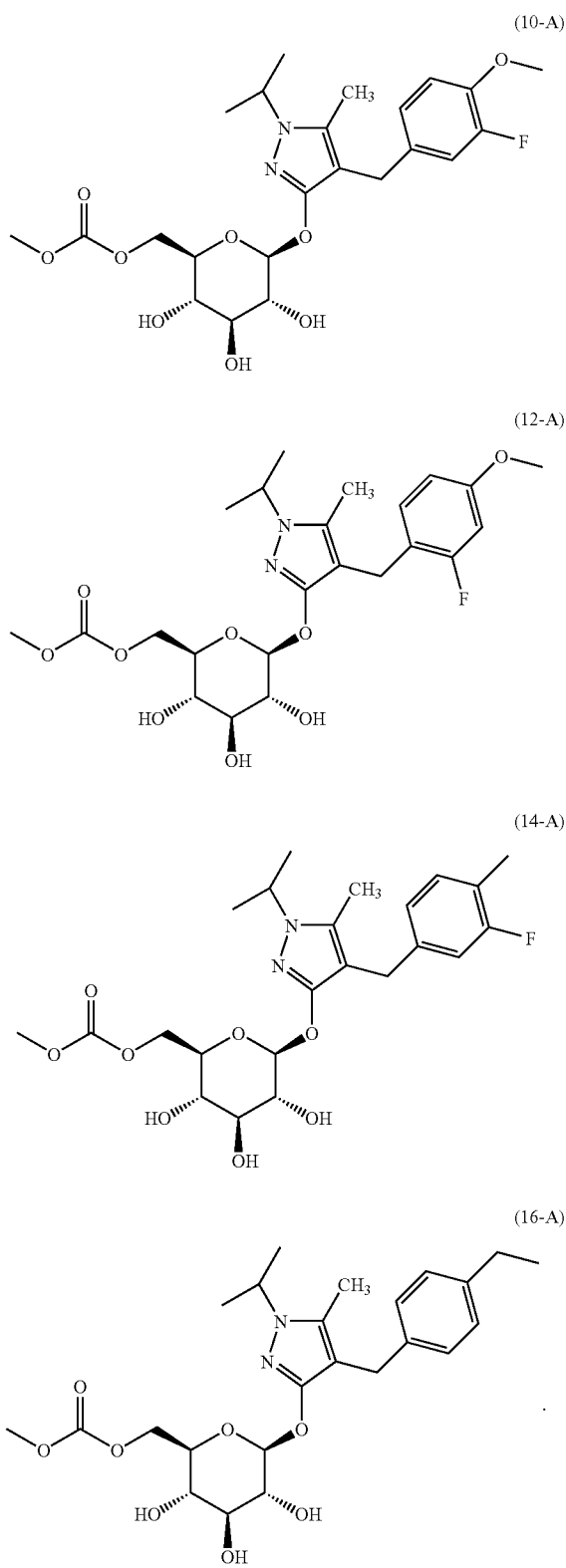

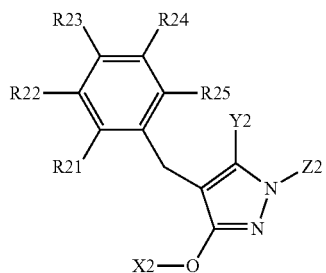

(5)

wherein
X2 represents β-D-glucopyranosyl group, wherein one or plural hydroxyl groups may be acylated;
Y2 represents hydrogen, a lower alkyl group, a fluoro-lower alkyl group or a perfluoro-lower alkyl group;
Z2 represents a halo-lower alkyl group;
R21 through R25 may be the same or different and represent hydrogen atom, a halogeno group, a lower alkyl group, a halo-lower alkyl group, a perfluoro-lower alkyl group, a lower alkoxy group, a perfluoro-lower alkoxy group, a lower alkylthio group, a perfluoro-lower alkylthio group, a lower alkylamino group, a lower alkanoyl group, a lower alkenyl group, a lower alkynyl group or an aralkyl group optionally substituted with a lower alkoxy group, a lower alkyl group, a halogeno group or a halogeno-lower alkyl group.

20. A therapeutic agent of diabetes mellitus according to claim 19, where the inhibitor of renal glucose reabsorption is at least one pyrazole-o-glycoside derivative where Z2 is a halo-lower alkyl group; Y2 is trifluoromethyl group; and X2 is β-D-glucopyranosyl group, wherein one or plural hydroxyl groups may be acylated with a group or groups selected from alkanoyl groups with 2 to 20 carbon atoms, lower alkoxy-carbonyl groups and benzoyl group, in the formula (5) or a pharmaceutically acceptable salt thereof.

21. A therapeutic agent of diabetes mellitus according to claim 19, where the inhibitor of renal glucose reabsorption is at least one pyrazole-o-glycoside derivative where Z2 is a fluoro-lower alkyl group; Y2 is trifluoromethyl group; and X2 is β-D-glucopyranosyl group, wherein one or plural hydroxyl groups may be acylated with a group or groups selected from alkanoyl groups with 2 to 20 carbon atoms, lower alkoxy-carbonyl groups and benzoyl group, in the formula (5) or a pharmaceutically acceptable salt thereof.

22. A therapeutic agent of diabetes mellitus according to claim 19, where the inhibitor of renal glucose reabsorption is at least one pyrazole-o-glycoside derivative where Z2 is a halo-lower alkyl group; Y2 is methyl group; and X2 is β-D-glucopyranosyl group, wherein one or plural hydroxyl groups may be acylated with a group or groups selected from alkanoyl groups with 2 to 20 carbon atoms, lower alkoxy-carbonyl groups and benzoyl group, in the formula (5) or a pharmaceutically acceptable salt thereof.

23. A therapeutic agent of diabetes mellitus according to claim 19, where the inhibitor of renal glucose reabsorption is at least one pyrazole-o-glycoside derivative where Z2 is a fluoro-lower alkyl group; Y2 is methyl group; and X2 is β-D-glucopyranosyl group, wherein one or plural hydroxyl groups may be acylated with a group or groups selected from alkanoyl groups with 2 to 20 carbon atoms, lower alkoxy-carbonyl groups and benzoyl group, in the formula (5) or a pharmaceutically acceptable salt thereof.

19. A therapeutic agent of diabetes mellitus according to claim 1, where the inhibitor of renal glucose reabsorption is at least one pyrazole-o-glycoside derivative of formula (5) or a pharmaceutically acceptable salt thereof:

24. A therapeutic agent of diabetes mellitus according to claim 19, where the inhibitor of renal glucose reabsorption is at least one compound of formulae (6) and/or (7) or a pharmaceutically acceptable salt thereof:

(6)

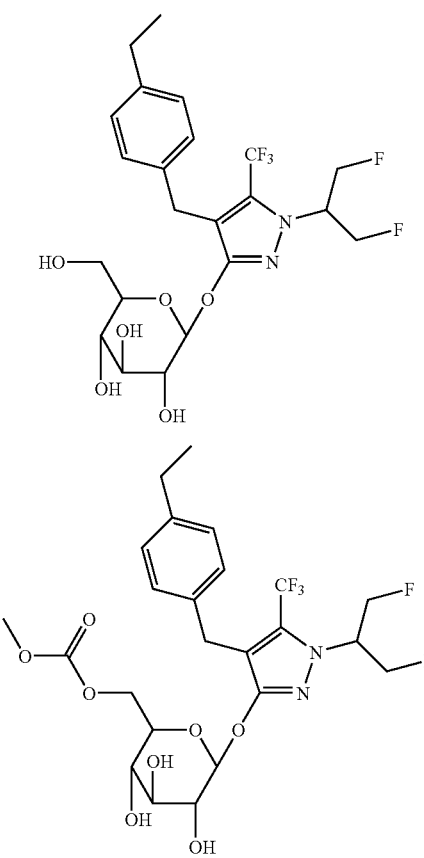

(7)

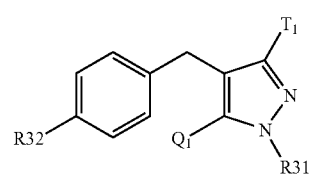

25. A therapeutic agent of diabetes mellitus according to claim 1, where the inhibitor of renal glucose reabsorption is at least one glucopyranosyloxypyrazole derivative of formula (8) or a pharmaceutically acceptable salt thereof:

(8)

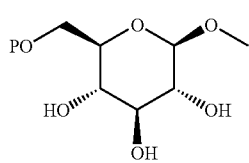

wherein
R31 is hydrogen atom or a lower alkyl group;
either one of $Q_1$ and $T_1$ is a group of formula (9):

(9)

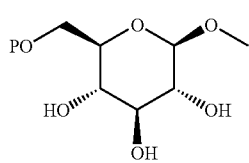

wherein P represents hydrogen atom, a lower acyl group, a lower alkoxy-lower acyl group, a lower alkoxy-carbonyl-lower acyl group, a lower alkoxy-carbonyl group or a lower alkoxy-lower alkoxy-carbonyl group, and the other is a lower alkyl group or a halo-lower alkyl group;
R32 is hydrogen atom, a lower alkyl group, a lower alkoxy group, a lower alkylthio group, a halo-lower alkyl group or a halogen atom.

26. A therapeutic agent of diabetes mellitus according to claim 1, where the inhibitor of renal glucose reabsorption is at least one pyrazole derivative of (3), (3a), (4a), (7), (10-A), (12-A), (14-A) and/or (16-A) or a pharmaceutically acceptable salt thereof:

(3)

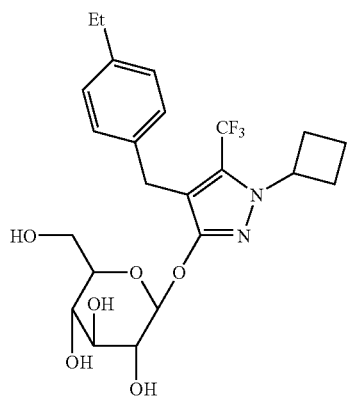

(3a)

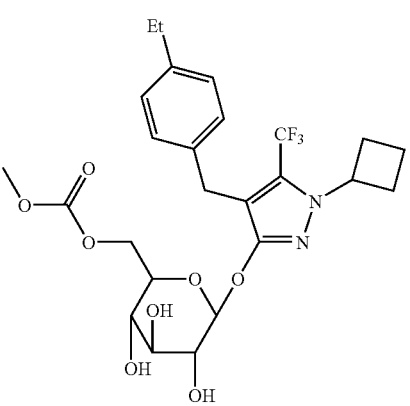

(4a)

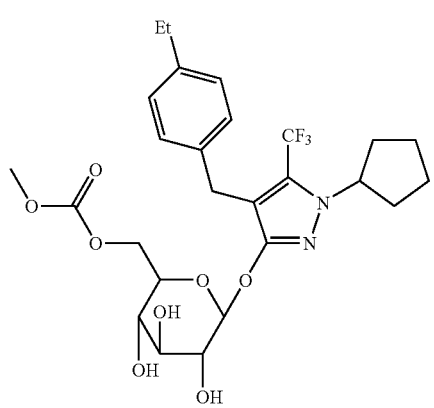

(7)

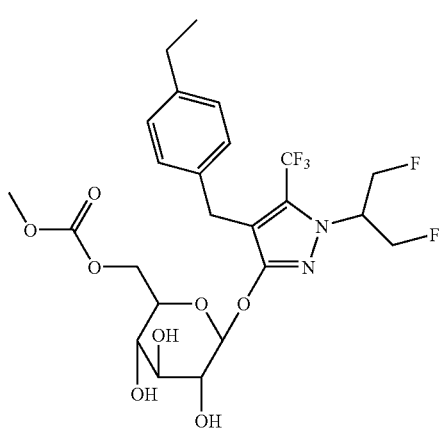

-continued

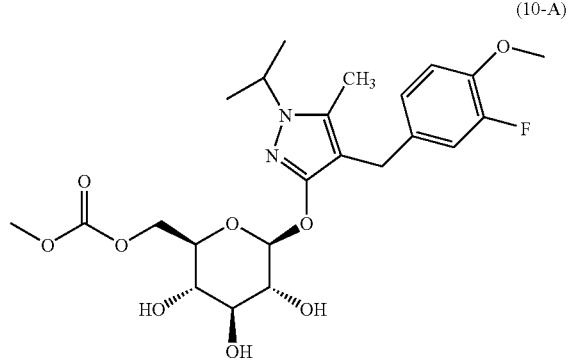
(10-A)

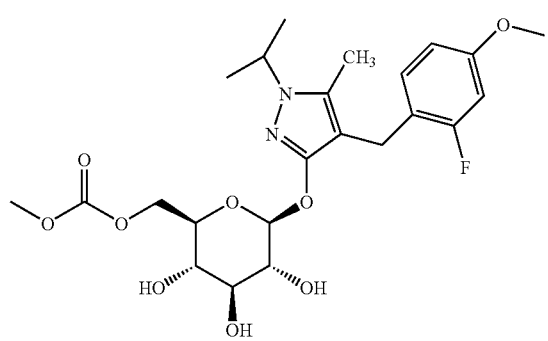
(12-A)

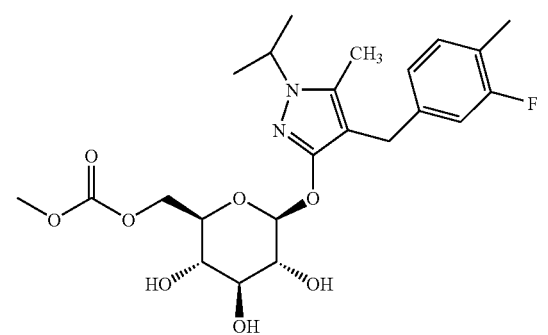
(14-A)

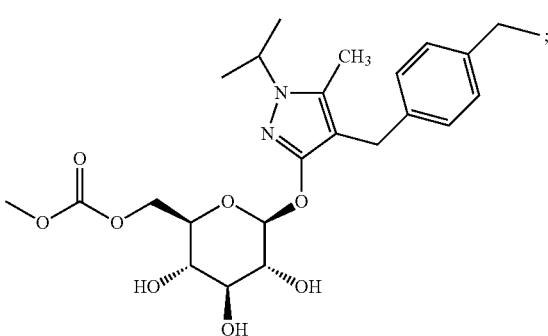
(16-A)

and where the hypoglycemic agent is at least one of glibenclamide and metformin.

27. A therapeutic agent of diabetes mellitus according to claim 11, wherein the inhibitor of renal glucose reabsorption is at least one pyrazole derivative selected from the group consisting of the compound of formula (9-A), the compound of formula (11-A), and the compound of formula (13-A), or a pharmaceutically acceptable salt thereof:

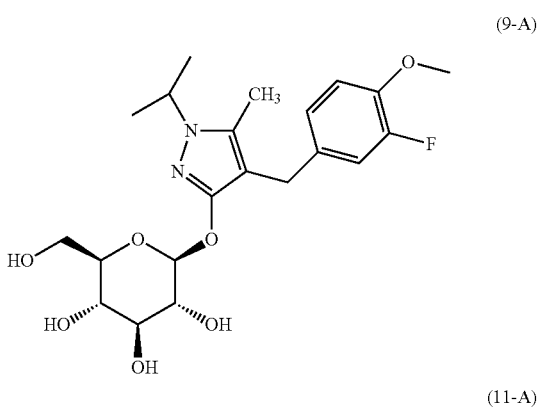
(9-A)

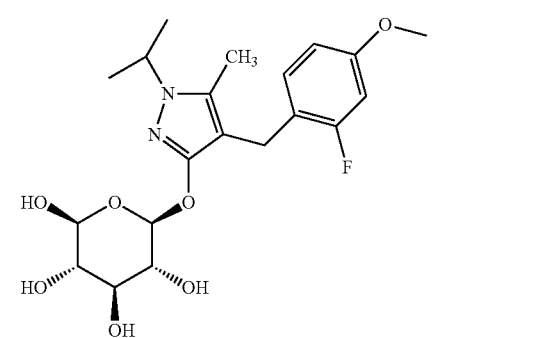
(11-A)

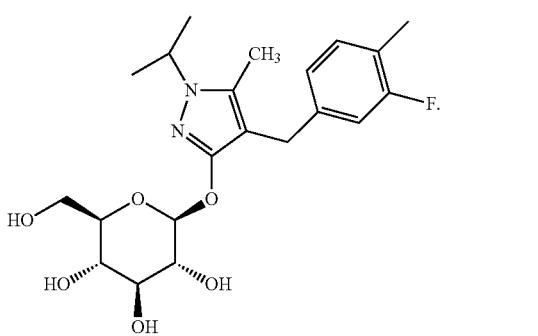
(13-A)

* * * * *

UNITED STATES PATENT AND TRADEMARK OFFICE
CERTIFICATE OF CORRECTION

PATENT NO. : 7,956,041 B2
APPLICATION NO. : 10/972743
DATED : June 7, 2011
INVENTOR(S) : Katsumi Maezono et al.

Page 1 of 1

It is certified that error appears in the above-identified patent and that said Letters Patent is hereby corrected as shown below:

Column 108, lines 25-39, Figure (11-A),

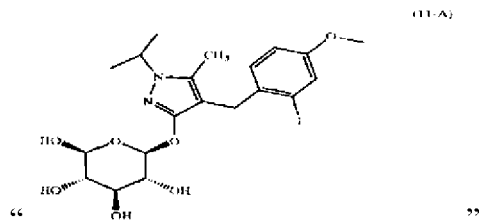

should read

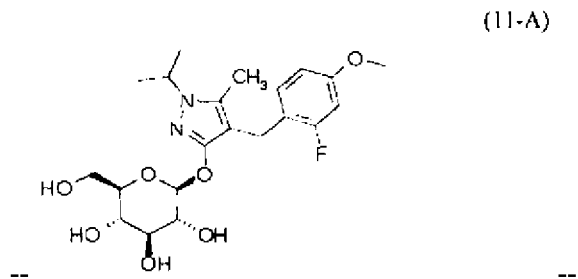

Signed and Sealed this
Thirteenth Day of December, 2011

David J. Kappos
*Director of the United States Patent and Trademark Office*